United States Patent
Lajiness et al.

(10) Patent No.: US 12,365,692 B2
(45) Date of Patent: Jul. 22, 2025

(54) 6-HYDROXY-8-OXATRICYCLO[3.2.1.02,4]OCTANE-2-CARBOXAMIDE DERIVATIVES FOR INDUCING CHONDROGENESIS FOR TREATING JOINT DAMAGE

(71) Applicant: NOVARTIS AG, Basel (CH)

(72) Inventors: James Paul Lajiness, San Diego, CA (US); Andrew Valiere, Descanso, CA (US)

(73) Assignee: NOVARTIS AG, Basel (CH)

(*) Notice: Subject to any disclaimer, the term of this patent is extended or adjusted under 35 U.S.C. 154(b) by 904 days.

(21) Appl. No.: 17/299,236

(22) PCT Filed: Dec. 4, 2019

(86) PCT No.: PCT/IB2019/060456
§ 371 (c)(1),
(2) Date: Jun. 2, 2021

(87) PCT Pub. No.: WO2020/115684
PCT Pub. Date: Jun. 11, 2020

(65) Prior Publication Data
US 2022/0033412 A1 Feb. 3, 2022

Related U.S. Application Data

(60) Provisional application No. 62/776,271, filed on Dec. 6, 2018.

(51) Int. Cl.

| | |
|---|---|
| *A61P 19/02* | (2006.01) |
| *A61K 31/343* | (2006.01) |
| *A61K 31/4155* | (2006.01) |
| *A61K 31/443* | (2006.01) |
| *A61K 31/444* | (2006.01) |
| *A61K 31/5377* | (2006.01) |
| *A61K 45/06* | (2006.01) |
| *A61P 19/04* | (2006.01) |
| *A61P 19/08* | (2006.01) |
| *A61P 19/10* | (2006.01) |
| *C07D 493/08* | (2006.01) |

(52) U.S. Cl.
CPC ........ *C07D 493/08* (2013.01); *A61K 31/4155* (2013.01); *A61K 31/443* (2013.01); *A61K 31/444* (2013.01); *A61K 31/5377* (2013.01); *A61K 45/06* (2013.01)

(58) Field of Classification Search
CPC ..... C07D 493/08; A61K 31/343; A61P 19/02; A61P 19/04; A61P 19/08; A61P 19/10
See application file for complete search history.

(56) References Cited

U.S. PATENT DOCUMENTS

2017/0112843 A1    4/2017  Schultz

FOREIGN PATENT DOCUMENTS

| WO | 2011008773 A2 | 1/2011 | |
| WO | WO-2015175487 A1 * | 11/2015 | ............. A61K 31/34 |
| WO | 2018/225009 A1 | 12/2018 | |
| WO | 2020115683 A1 | 6/2020 | |

OTHER PUBLICATIONS

Hu et al. (Development. Jan. 15, 2017; 144(2): 221-234. doi:10.1242/dev.130807. PMCID: PMC5394763. PMID: 28096214). (Year: 2017).*

Karimian et al. ("Genetic regulation of the growth plate." Front Endocrinol (Lausanne). Jan. 9, 2012;2:113. doi: 10.3389/fendo.2011.00113. PMID: 22654844; PMCID: PMC3356134). (Year: 2012).*

* cited by examiner

*Primary Examiner* — Amanda L. Aguirre
*Assistant Examiner* — Chris E Simmons
(74) *Attorney, Agent, or Firm* — Emily T. Wu

(57) ABSTRACT

The present invention provides 6-hydroxy-8-oxatricyclo [3.2.1.02,4]octane-2-carboxamide derivatives of Formula (1) wherein the variables are as defined herein. The present invention further provides pharmaceutical compositions comprising such compounds. The compounds are used for inducing chondrogenesis, in methods of treating or preventing joint damage, resulting from joint injury or arthritis, and for inducing hyaline cartilage production. The present description discloses the preparation of exemplary compounds as well as pharmacological data thereof (examples 1 to 82; tables 1 and 2). An exemplary compound is e.g. rac-(1R,2R,4S,5R,6S)-4-(2-fluoropyridin-4-yl)-6-hydroxy-N-(4-(trifluoromethyl)pyridin-2-yl)-8-oxatricyclo[3.2.1.02,4]octane-2-carboxamide (example 1).

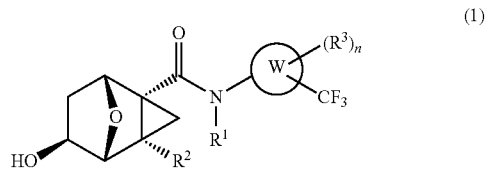

(1)

24 Claims, No Drawings

6-HYDROXY-8-OXATRICYCLO[3.2.1.0²,⁴] OCTANE-2-CARBOXAMIDE DERIVATIVES FOR INDUCING CHONDROGENESIS FOR TREATING JOINT DAMAGE

CROSS-REFERENCE TO RELATED APPLICATIONS

This application is a 371 U.S. national phase application of international application number PCT/IB2019/060456 filed 4 Dec. 2019, which claims the benefit of U.S. provisional application Ser. No. 62/776,271 filed 6 Dec. 2018; each of which is incorporated by reference herein in its entirety.

FIELD OF THE INVENTION

The present invention relates to compositions and methods for treating or preventing joint damage resulting from joint injury and arthritis, or for cartilage repair.

BACKGROUND OF THE INVENTION

Osteoarthritis (OA) represents the most common musculoskeletal disorder. Approximately 40 million Americans are currently affected and this number is predicted to increase to 60 million within the next twenty years as a result of the aging population and an increase in life expectancy, making it the fourth leading cause of disability. OA is characterized by a slow degenerative breakdown of the joint including both the articular cartilage (containing the cells and matrix which produce lubrication and cushioning for the joint) and the subchondral bone underlying the articular cartilage. OA can be considered a consequence of various etiologic factors. For example, it can be caused by abnormal biomechanical stress or genetic or acquired abnormalities of articular cartilage or bone. Current OA therapies include pain relief with oral NSAIDs or selective cyclooxygenase 2 (COX-2) inhibitors, intra-articular (IA) injection with agents such as corticosteroids and hyaluronan, and surgical approaches.

Joint damage, e.g., acute joint injury, such as a meniscal or ligament tear, or an intra-articular fracture can also lead to arthritis, e.g., posttraumatic arthritis. Because articular cartilage has a limited ability to repair, even small undetectable damage can often get worse overtime and lead to OA. Current treatments for joint injury can include surgery and other invasive procedures focused on regeneration of damaged joints as well as treatment with agents to reduce pain and inflammation.

Mesenchymal stem cells (MSCs) are present in adult articular cartilage and upon isolation can be programmed in vitro to undergo differentiation to chondrocytes and other mesenchymal cell lineages, and may be used for cartilage regeneration. In part, the process is regulated by growth factors (TGFβs, BMPs), serum conditions and cell-cell contact.

WO2011/008773 describes peptide compositions and use of those compositions for treating or preventing arthritis and joint injury and for inducing differentiation of mesenchymal cells into chondrocytes. Additionally, WO2012/129562 describes small molecule compounds, compositions and use of those compositions for amelioration of arthritis and joint injury and for inducing differentiation of mesenchymal cells into chondrocytes.

Though surgical techniques, and regenerative technology have made some progress in restoration of cartilage, slowing degeneration, and improved repair of joint damage, a continued need exists for improvement of compositions and methods for effective cartilage regeneration, treatment of joint damage and amelioration or prevention of OA.

SUMMARY OF THE INVENTION

The present invention relates to compositions and methods for treating or preventing joint damage resulting from joint injury and arthritis, or for cartilage repair.

In one aspect, the invention provides a compound of Formula (1):

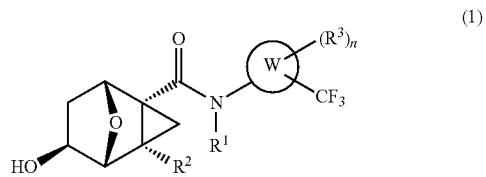

or an enantiomer, an enantiomeric mixture thereof or a pharmaceutically acceptable salt thereof; wherein
W is phenyl or pyridyl;
$R^1$ is hydrogen or $C_{1-6}$alkyl;
$R^2$ is phenyl or a 5-6 membered heteroaryl having 1-2 heteroatoms selected from N, O and S; wherein $R^2$ is unsubstituted or substituted by 1-2 substituents independently selected from halo, $C_{1-6}$ alkyl, $C_{1-6}$ haloalkyl or $C_{1-6}$alkoxy;
$R^3$ is independently selected from halo, cyano, $C_{1-6}$alkyl, $C_{1-6}$haloalkyl, $C_{1-6}$alkoxy, $C_{3-6}$ cycloalkyl and 5-6 membered heterocyclyl; or $R^3$ is hydrogen when n is 0; and
n is 0-2.

In another aspect, the invention provides a pharmaceutical composition comprising a therapeutically effective amount of a compound of Formula (1) or sub-formulae thereof, or an enantiomer, an enantiomeric mixture thereof or a pharmaceutically acceptable salt thereof; and one or more pharmaceutically acceptable carriers.

In yet another aspect, the invention provides a combination, in particular a pharmaceutical combination, comprising a therapeutically effective amount of a compound of Formula (1) or sub-formulae thereof, or an enantiomer, an enantiomeric mixture thereof or a pharmaceutically acceptable salt thereof; and one or more therapeutically active agent(s).

The compounds of the invention, alone or in combination with one or more therapeutically active agent(s), can be used for treating, ameliorating or preventing acute joint damage or injury, such as arthritis (osteoarthritis, traumatic arthritis, systemic rheumatoid arthritis) or degenerative disc disease. Furthermore, the compounds of the invention, alone or in combination with one or more therapeutically active agent(s), can be used for inducing hyaline cartilage production.

DETAILED DESCRIPTION OF THE INVENTION

The present invention provides novel compounds that stimulate hyaline cartilage production in injured joints.

In one aspect, the present invention provides novel compounds and compositions for repairing cartilage. Also provided are compositions and methods to treat, prevent or ameliorate arthritis or joint injury by administering a compound or composition of the invention into a joint, a cartilage tissue or a cartilage proximal tissue, or systemically. Further, the invention provides compositions and methods for inducing hyaline cartilage production.

Definitions

For purposes of interpreting this specification, the following definitions will apply and whenever appropriate, terms used in the singular will also include the plural and vice versa.

As used herein, the term "$C_{1-5}$alkoxy" refers to a radical of the formula —$OR_a$ where $R_a$ is a $C_{1-5}$alkyl radical as generally defined above. Examples of $C_{1-6}$alkoxy include, but are not limited to, methoxy, ethoxy, propoxy, iso-propoxy, butoxy, isobutoxy, pentoxy, and hexoxy. The alkyl portion of the alkoxy may be optionally substituted, and the substituents include those described for the alkyl group below.

As used herein, the term "$C_{1-6}$ alkyl" refers to a straight or branched hydrocarbon chain radical consisting solely of carbon and hydrogen atoms, containing no unsaturation, having from one to six carbon atoms, and which is attached to the rest of the molecule by a single bond. Examples of $C_{1-6}$alkyl include, but are not limited to, methyl, ethyl, n-propyl, 1-methylethyl (iso-propyl), n-butyl, n-pentyl and 1,1-dimethylethyl (t-butyl).

"Amino", as used herein, refers to the radical —$NH_2$. Unless otherwise indicated, the compounds of the invention containing amino moieties may include protected derivatives thereof. Suitable protecting groups for amino moieties include acetyl, tert-butoxycarbonyl, benzyloxycarbonyl, and the like.

"Heterocyclyl" or "heterocyclic", as used herein, refer to a stable 5- or 6-membered non-aromatic monocyclic ring radical which comprises 1, 2, or 3, heteroatoms individually selected from nitrogen, oxygen and sulfur. The heterocyclyl radical may be bonded via a carbon atom or heteroatom. Examples of heterocyclyl include, but are not limited to, pyrrolinyl, pyrrolidyl, tetrahydrofuryl, tetrahydrothienyl, piperidyl, piperazinyl, tetrahydropyranyl or morpholinyl.

As used herein, the term "heteroaryl" refers to a 5- or 6-membered aromatic monocyclic ring radical which comprises 1, 2, 3 or 4 heteroatoms individually selected from nitrogen, oxygen and sulfur. The heteroaryl radical may be bonded via a carbon atom or heteroatom. Examples of heteroaryl include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl.

"$IC_{50}$", as used herein, refers to the molar concentration of an inhibitor or modulator that produces 50% inhibition.

"Halo" or "halogen", as used herein, refers to fluoro, chloro, bromo, and iodo.

"Halo-substituted $C_{1-6}$alkyl", as used herein, refers to a $C_{1-6}$alkyl radical as defined above, substituted by one or more halo radicals as defined above. Examples of halo-substituted $C_{1-6}$ alkyl include, but are not limited to, trifluoromethyl, difluoromethyl, fluoromethyl, trichloromethyl, 2,2,2-trifluoroethyl, 1,3-dibromopropan-2-yl, 3-bromo-2-fluoropropyl and 1,4,4-trifluorobutan-2-yl.

"Protected derivatives", as used herein, refers to derivatives of inhibitors in which a reactive site or sites are blocked with protecting groups. Protected derivatives are useful in the preparation of inhibitors or in themselves may be active as inhibitors. Examples of protected group includes, but are not limited to, acetyl, tetrahydropyran, methoxymethyl ether, β-methoxyethoxymethyl ether, ρ-methoxybenzyl, methylthiomethyl ether, pivaloyl, silyl ether, carbobenzyloxy, benzyl, tert-butoxy carbonyl, ρ-methoxyphenyl, 9-fluorenylmethyloxycarbonyl, acetals, ketals, acylals, dithianes, methylesters, benzyl esters, tert-butyl esters, and silyl esters. A comprehensive list of suitable protecting groups can be found in T. W. Greene, *Protecting Groups in Organic Synthesis*, 3rd edition, John Wiley & Sons, Inc. 1999.

As used herein, the term "chondrocytes" refers to differentiated cartilage cells. Chondrocytes produce and maintain the cartilaginous matrix which is composed of collagen and proteoglycans. Chondrocytes are derived from the differentiation of chondrogenic progenitor cells (CPCs). Differentiation is the process a specialized cell type is formed from a less specialized cell type, for example, a chondrocyte from a chondrogenic progenitor cell (CPC).

As used herein, the term "chondrocyte differentiation agent" refers to an agent that induces chondrogenic progenitor cells to differentiate into mature chondrocyte, which then synthesize the cartilage extra-cellular matrix (ECM).

As used herein, the term "subject" refers to mammals, primates (e.g., humans, male or female), dogs, rabbits, guinea pigs, pigs, rats and mice. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing" or "prevention" of any disease or disorder refers to the prophylactic treatment of the disease or disorder; or delaying the onset or progression of the disease or disorder As used herein, a subject is "in need of" a treatment if such subject would benefit biologically, medically or in quality of life from such treatment.

As used herein, the term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject in need thereof, is effective to at least partially alleviate, inhibit, prevent and/or ameliorate joint damage resulting from joint injury and arthritis. In another non-limiting embodiment, the term "a therapeutically effective amount" refers to the amount of the compound of the present invention that, when administered to a cell, or a tissue, or a non-cellular biological material, or a medium, is effective to promote chondrogenesis.

As used herein, "administering" refers to administration to a specific joint.

As used herein, the term "pharmaceutical composition" refers to a compound of the invention, or a pharmaceutically acceptable salt thereof, together with at least one pharmaceutically acceptable carrier, in a form suitable for oral or parenteral administration.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, 22$^{nd}$ Ed. Pharmaceutical Press, 2013, pp. 1049-1070).

As used herein, the term "a," "an," "the" and similar terms used in the context of the present invention (especially in the context of the claims) are to be construed to cover both the singular and plural unless otherwise indicated herein or clearly contradicted by the context.

DESCRIPTION OF PREFERRED EMBODIMENTS

The present invention relates to compositions and methods for treating or preventing joint damage resulting from joint injury and arthritis, or cartilage repair.

Various enumerated embodiments of the invention are described herein. Features specified in each embodiment may be combined with other specified features to provide further embodiments of the present invention.

Embodiment 1. A compound of Formula (1), or an enantiomer, an enantiomeric mixture thereof or a pharmaceutically acceptable salt thereof, as described above.

Embodiment 2. A compound of Formula (1) according to Embodiment 1, or an enantiomer, an enantiomeric mixture thereof or a pharmaceutically acceptable salt thereof; wherein $R^2$ is phenyl, pyrazolyl, pyridyl or pyrimidinyl; each of which is substituted by 1-2 substituents independently selected from halo, $C_{1-6}$ alkyl, $C_{1-6}$ haloalkyl or $C_{1-6}$ alkoxy.

Embodiment 3. A compound of Formula (1) according to Embodiment 1, or an enantiomer, an enantiomeric mixture thereof or a pharmaceutically acceptable salt thereof; wherein $R^2$ is selected from phenyl, pyrazolyl or pyrimidinyl; each of which is substituted by 1-2 substituents independently selected from halo, $C_{1-6}$ alkyl, $C_{1-6}$ haloalkyl or $C_{1-6}$ alkoxy; or $R^2$ is pyridyl substituted by halo, $C_{1-6}$ haloalkyl or $C_{1-6}$ alkoxy.

Embodiment 4. A compound of Formula (1) according to any one of Embodiments 1-3, or an enantiomer, an enantiomeric mixture thereof or a pharmaceutically acceptable salt thereof; wherein

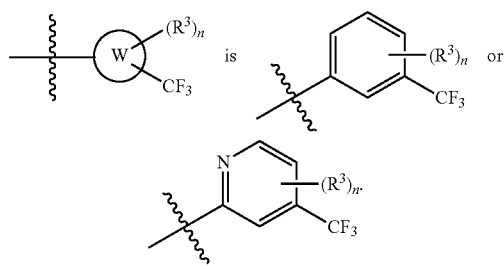

Embodiment 5. A compound of Formula (1) according to any one of Embodiments 1-3, or an enantiomer, an enantiomeric mixture thereof or a pharmaceutically acceptable salt thereof; wherein

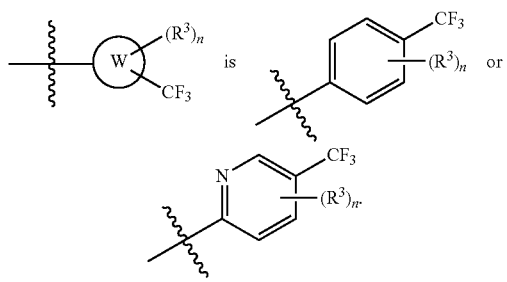

Embodiment 6. A compound of Formula (1) according to any one of Embodiments 1-3, or an enantiomer, an enantiomeric mixture thereof or a pharmaceutically acceptable salt thereof; wherein

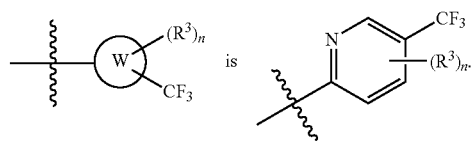

Embodiment 7. A compound according to any one of Embodiments 1-6, wherein said compound is of Formula (2):

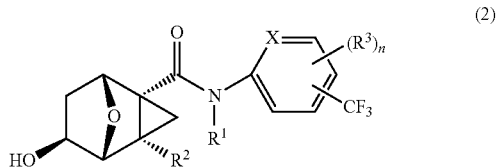

or an enantiomer, an enantiomeric mixture thereof or a pharmaceutically acceptable salt thereof; wherein
X is N, CH or $CR^4$; and
$R^4$ is halo, cyano, $C_{1-6}$alkyl, $C_{1-6}$haloalkyl or $C_{1-6}$ alkoxy.

Embodiment 8A. A compound according to Embodiment 7, wherein said compound is of Formula (2A):

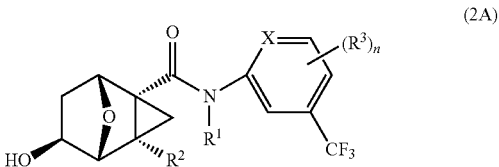

or an enantiomer, an enantiomeric mixture thereof or a pharmaceutically acceptable salt thereof; wherein
X is N, CH or $CR^4$; and
$R^4$ is halo, cyano, $C_{1-6}$alkyl, $C_{1-6}$haloalkyl or $C_{1-6}$alkoxy.

Embodiment 8B. A compound according to Embodiment 7, wherein said compound is of Formula (2B):

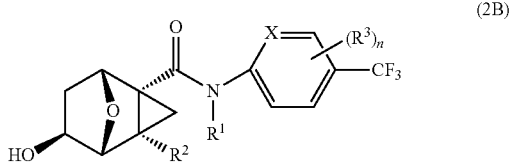

(2B)

or an enantiomer, an enantiomeric mixture thereof or a pharmaceutically acceptable salt thereof; wherein X is N, CH or $CR^4$; and $R^4$ is halo, cyano, $C_{1-6}$alkyl, $C_{1-6}$haloalkyl or $C_{1-6}$alkoxy.

Embodiment 9. A compound according to any one of Embodiments 1-7 and 8A-8B, or an enantiomer, an enantiomeric mixture thereof or a pharmaceutically acceptable salt thereof; wherein $R^3$, if present, is fluoro, chloro, methyl, methoxy, ethoxy, trifluoromethyl, cyano, cyclopropyl or morpholinyl.

Embodiment 10. A compound according to any one of Embodiments 1-7 and 8A-8B, or an enantiomer, an enantiomeric mixture thereof or a pharmaceutically acceptable salt thereof; wherein $R^3$ is hydrogen and n is 0.

Embodiment 11A. A compound according to any one of Embodiments 1-7, 8A-8B and 9-10, or an enantiomer, an enantiomeric mixture thereof or a pharmaceutically acceptable salt thereof; wherein $R^2$ is selected from:

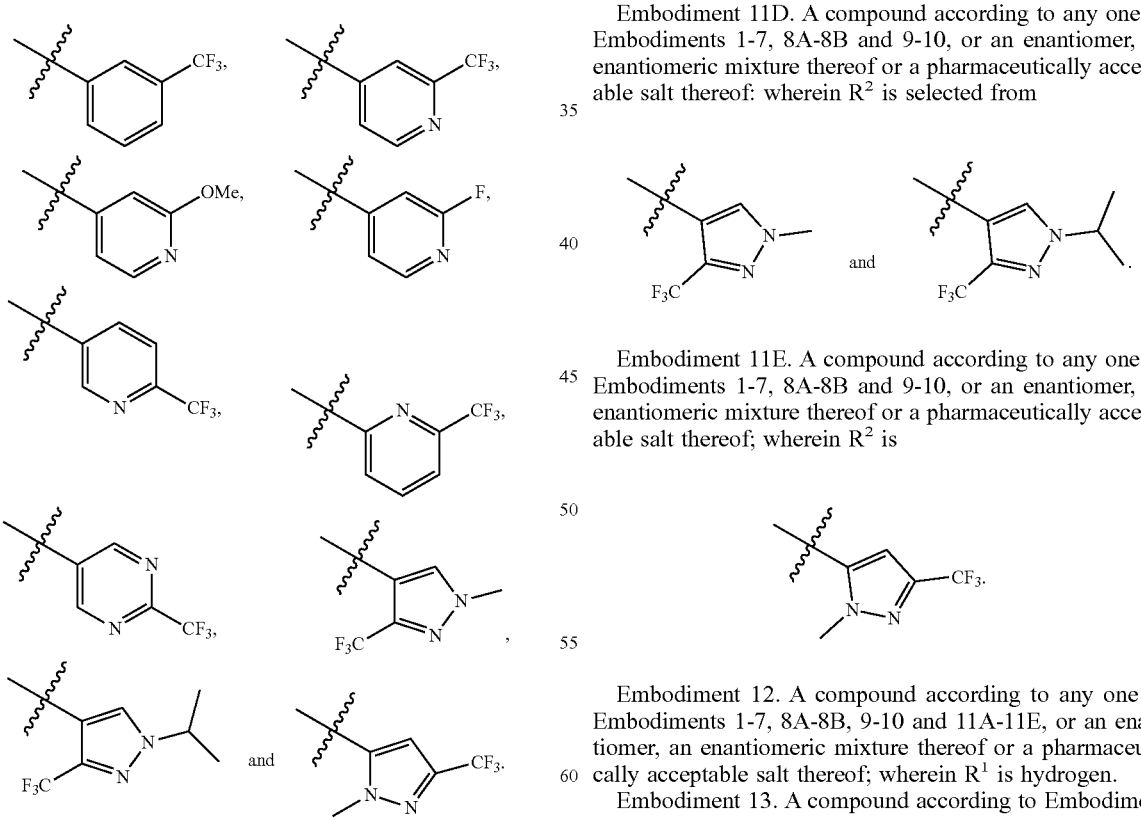

Embodiment 11B. A compound according to any one of Embodiments 1-7, 8A-8B and 9-10, or an enantiomer, an enantiomeric mixture thereof or a pharmaceutically acceptable salt thereof; wherein $R^2$ is

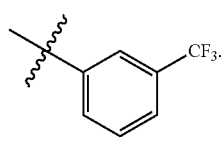

Embodiment 11C. A compound according to any one of Embodiments 1-7, 8A-8B and 9-10, or an enantiomer, an enantiomeric mixture thereof or a pharmaceutically acceptable salt thereof; wherein $R^2$ is selected from:

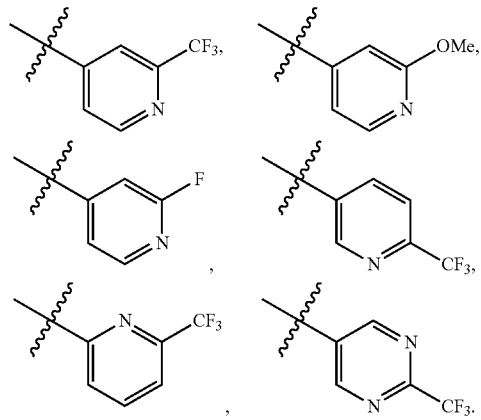

Embodiment 11D. A compound according to any one of Embodiments 1-7, 8A-8B and 9-10, or an enantiomer, an enantiomeric mixture thereof or a pharmaceutically acceptable salt thereof: wherein $R^2$ is selected from

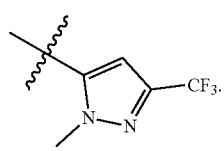 [SMILES: *c1cc(C(F)(F)F)nn1C]

Embodiment 11E. A compound according to any one of Embodiments 1-7, 8A-8B and 9-10, or an enantiomer, an enantiomeric mixture thereof or a pharmaceutically acceptable salt thereof; wherein $R^2$ is Embodiment 12. A compound according to any one of Embodiments 1-7, 8A-8B, 9-10 and 11A-11E, or an enantiomer, an enantiomeric mixture thereof or a pharmaceutically acceptable salt thereof; wherein $R^1$ is hydrogen.

Embodiment 13. A compound according to Embodiment 1, wherein said compound is selected from a compound in Table 2 or Table 3; or an enantiomer, an enantiomeric mixture thereof or a pharmaceutically acceptable salt thereof.

Embodiment 14. A compound according to any one of Embodiments 1-7, 8A-8B, 9-10, 11A-11E and 12-13 or a pharmaceutically acceptable salt thereof, wherein said compound has an enantiomeric excess of at least 50%, at least 75%, at least 85%, or at least 95% of the (1R,2R,3S,4R,5S) enantiomer.

Embodiment 15. A pharmaceutical composition comprising a compound according to any one of Embodiments 1-7, 8A-8B, 9-10, 11A-11E and 12-14 and one or more pharmaceutically acceptable carrier.

Embodiment 16. A combination comprising a compound according to any one of Embodiments 1-7, 8A-8B, 9-10, 11A-11E and 12-14 and one or more therapeutically active agent.

Embodiment 17. A compound according to any one of Embodiments 1-7, 8A-8B, 9-10, 11A-11E and 12-14 and optionally in combination with a second therapeutic agent, for use in treating, ameliorating or preventing arthritis or joint injury in a subject in need thereof, or for cartilage repair.

Embodiment 18. Use of a compound according to any one of Embodiments 1-7, 8A-8B, 9-10, 11A-11E and 12-14 and optionally in combination with a second therapeutic agent, in the manufacture of a medicament for arthritis or joint injury, or for cartilage repair.

Embodiment 19. A method for treating, ameliorating or preventing arthritis or joint injury, or for cartilage repair in a subject in need thereof, comprising administering a therapeutically effective amount of a compound according to any one of Embodiments 1-7, 8A-8B, 9-10, 11A-11E and 12-14 and optionally in combination with a second therapeutic agent; thereby treating, ameliorating or preventing arthritis or joint injury, or repairing cartilage, in said subject.

Embodiment 20. A method according to Embodiment 19, wherein said compound is administered orally.

Embodiment 21. A compound according to Embodiment 17, a use according to Embodiment 18, or a method according to Embodiments 19 or 20, wherein the arthritis is osteoarthritis, trauma arthritis, or autoimmune arthritis; and optionally, wherein the arthritis is osteoarthritis or rheumatoid arthritis.

Embodiment 22. A method of inducing hyaline cartilage production, comprising contacting chondrogenic progenitor cells with a therapeutically effective amount of a compound according to any one of Embodiments 1-7, 8A-8B, 9-10, 11A-11E and 12-14 and optionally in combination with a second therapeutic agent; thereby inducing hyaline cartilage extracellular matrix.

Embodiment 23. A method of inducing differentiation of chondrogenic progenitor cells into mature chondrocytes, comprising contacting chondrogenic progenitor cells with a therapeutically effective amount of a compound according to any one of Embodiments 1-7, 8A-8B, 9-10, 11A-11E and 12-14 and optionally in combination with a second therapeutic agent; thereby inducing differentiation of chondrocyte progenitor cells into mature chondrocytes.

Embodiment 24. A method according to Embodiment 22 or Embodiment 23, wherein said contacting step is performed in vitro or in vivo in a mammal; and when in vivo, the chondrogenic progenitor cells are present in the mammal.

Embodiment 25. A method according to Embodiment 24, wherein said contacting step occurs in an extracellular matrix or biocompatible scaffold.

Embodiment 26. A compound according to Embodiment 17, a use according to Embodiment 18, or an embodiment according to any one of Embodiments 19-25, wherein said second therapeutic agent is a chondrocyte differentiation agent.

Embodiment 27. A compound according to Embodiment 17, a use according to Embodiment 18, or an embodiment according to any one of Embodiments 19-25, wherein said second therapeutic agent is selected from angiopoietin-like 3 protein (ANGPTL3), insulin growth factor (IGF1), SM04690, Janus kinase inhibitor, oral salmon calcitonin, SD-6010, vitamin D3, collagen hydrolyzate, bone morphogenetic protein 7 (BMP7), rusalatide acetate, avocado soy unsaponifiables (ASU), a steroid, a non-steroidal anti-inflammatory agent (NSAID), hyaluronic acid, kartogenin, TPX-100, and a chondrocyte differentiation agent having Formula (I) or sub-formulae thereof as described in WO 2015/175487.

Embodiment 28. The compound according to Embodiment 27, the use according to Embodiment 27, or an embodiment according to Embodiment 27, wherein said second therapeutic agent is a chondrocyte differentiation agent selected from:
(1R,2S,3R,4S)—N-(3,4-dichlorophenyl)-3-(1-methyl-3-(trifluoromethyl)-1H-pyrazol-5-yl)-7-oxabicyclo)[2.2.1]heptane-2-carboxamide;
(1S,2R,3R,4R)—N-(3,4-dichlorophenyl)-3-(pyridin-4-yl)-7-oxabicyclo[2.2.1]heptane-2-carboxamide;
(1 S,2S,3R,4R)-3-(2-aminopyridin-4-yl)-N-(3,4-dichlorophenyl)-7-oxabicyclo[2.2.1]heptane-2-carboxamide;
(1R,2S,3S,4S)—N-(3,4-dichlorophenyl)-3-(pyridin-4-yl)-7-oxabicyclo[2.2.1]heptane-2-carboxamide;
N-(2-chloro-2'-fluoro-[1,1'-biphenyl]-4-yl)-3-(1H-pyrazol-5-yl)-7-oxabicyclo[2.2.1]hept-2-ene-2-carboxamide;
(1R,2R,3S,4S)—N-(3,4-dichlorophenyl)-3-(pyridin-4-yl)-7-oxabicyclo[2.2.1]heptane-2-carboxamide;
(1S,2S,3R,4R)—N-(3,4-dichlorophenyl)-3-(pyridin-4-yl)-7-oxabicyclo[2.2.1]heptane-2-carboxamide;
(1R,2R,3S,4S)-3-(2-aminopyridin-4-yl)-N-(3,4-dichlorophenyl)-7-oxabicyclo[2.2.1]heptane-2-carboxamide;
(1R,2R,4S,5S)—N-(3,4-dichlorophenyl)-4-(pyridin-4-yl)-8-oxatricyclo[3.2.1.02,4]octane-2-carboxamide; and
N-(2,2'-difluoro-[1,1'-biphenyl]-4-yl)-3-(pyrazin-2-yl)-7-oxabicyclo[2.2.1]hept-2-ene-2-carboxamide;
or an enantiomer, enantiomeric mixture of a pharmaceutically acceptable salt thereof.

Unless specified otherwise, the term "compounds of the present invention" refers to compounds of Formula (1) and sub-formulae thereof (e.g., Formula (2)) and enantiomers and salts thereof, as well as rotamers, tautomers, isotopically labeled compounds (including deuterium substitutions), and inherently formed moieties.

Unless otherwise indicated, a compound represented herein as a single enantiomer encompasses the enantiomer of the depicted compound and mixtures of the enantiomers, including racemic mixtures. Any asymmetric atom (e.g., cartoon or the like) of the compound(s) of the present invention can be racemic or enantiomerically enriched, for example the (R)-, (S)- or (R,S)-configuration. Any resulting racemates of final products or intermediates can be resolved into the optical antipodes by known methods, e.g., by chiral chromatography such as high pressure liquid chromatography (HPLC) using a chiral adsorbent.

In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Isotopes that can be incorporated into compounds of the invention include, for example, isotopes of hydrogen.

Further, incorporation of certain isotopes, particularly deuterium (i.e., $^2$H or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of Formula (1) or sub-formulae thereof. The concentration of deuterium, may be defined by the isotopic enrichment factor. The term "isotopic enrichment factor" as used herein means the ratio between the isotopic abundance and the natural abundance of a specified isotope. If a substituent in a compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into compounds of the invention include isotopes of hydrogen, carbon, nitrogen, oxygen, phosphorous, fluorine, and chlorine, such as $^3$H, $^{11}$C, $^{13}$C, $^{14}$C, $^{15}$N, $^{18}$F $^{31}$P, $^{32}$P, $^{35}$S, $^{36}$Cl, $^{123}$I, $^{124}$I, $^{125}$I respectively. Accordingly it should be understood that the invention includes compounds that incorporate one or more of any of the aforementioned isotopes, including for example, radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of Formula (1) or sub-formulae thereof can generally be prepared by conventional techniques known to those skilled in the art or by processes analogous to those described in the accompanying examples using an appropriate isotopically-labeled reagents in place of the non-labeled reagent previously employed.

The compounds of the present invention are either obtained in the free form, as a salt thereof. As used herein, the terms "salt" or "salts" refers to an acid addition or base addition salt of a compound of the invention. "Salts" include in particular "pharmaceutical acceptable salts".

The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable add addition salts can be formed with inorganic acids and organic acids. Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic add, succinic acid, fumaric acid, tartaric acid, citric acid, benzoic acid, mandelic acid, methanesulfonic add, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of the present invention in acetate, ascorbate, adipate, aspartate, benzoate, besylate, bromide/hydrobromide, bicarbonate/carbonate, bisulfate/sulfate, camphorsulfonate, caprate, chloride/hydrochloride, chlorotheophyllinate, citrate, ethanedisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Processes for Making Compounds of the Invention

All methods described herein can be performed in any suitable order, unless otherwise indicated or otherwise clearly contradicted by context.

Compounds of Formula (1) can be prepared as generally illustrated in Scheme 1, wherein $R^1$, $R^2$, $R^3$, W and n are as defined above. In the scheme below, the formula depicted as Formula (1) encompasses the depicted formula, and a mixture of the depicted formula and its corresponding enantiomer, including racemic mixtures.

Scheme 1

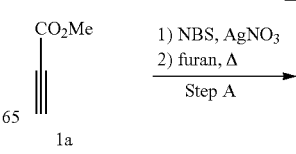

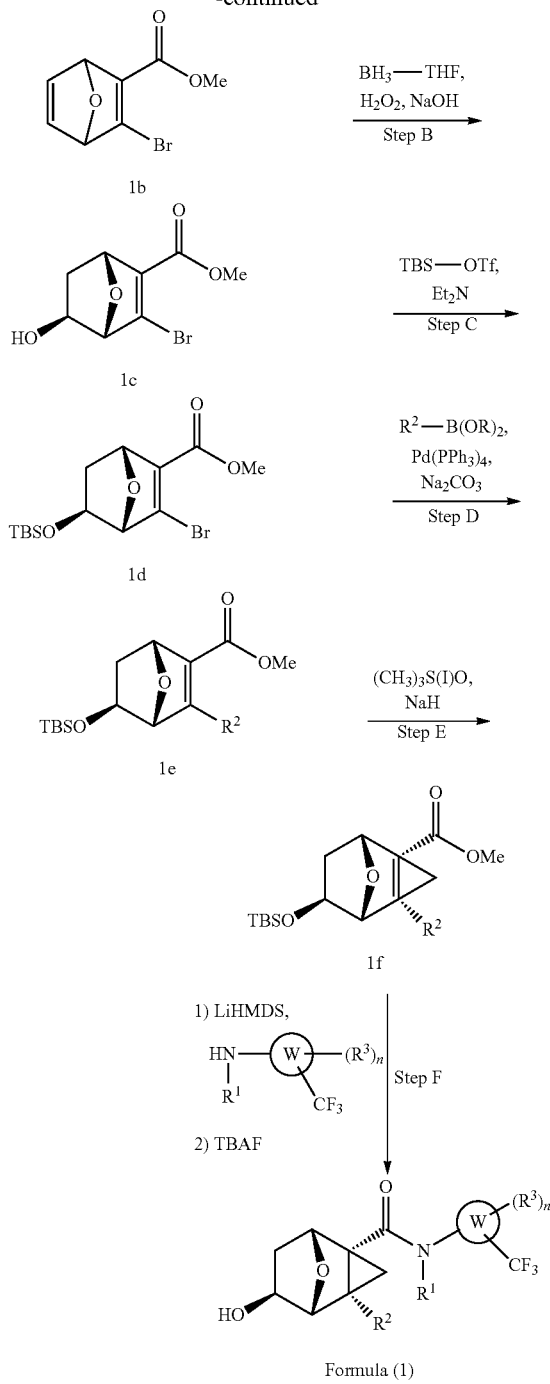

Formula (1)

Intermediate 1b can be prepared from commercially available methyl propiolate, 1a, via bromination and Diels-Alder reaction with furan. Intermediate 1c can be prepared via hydroboration/oxidation of intermediate 1b. Intermediate 1d can be prepared via TBS protection of intermediate 1c. Intermediate 1e can be prepared by Suzuki coupling on intermediate 1d. Cyclopropanation of intermediate 1e afforded intermediate 1f. Amide bond formation using intermediate if, an aniline, and LiHMDS and subsequent deprotection using TBAF afforded compounds of Formula (1).

The invention further includes any variant of the present processes; for example, wherein an intermediate product obtainable at any stage thereof is used as starting material and the remaining steps are carried out: wherein starting materials are formed in situ under the reaction conditions; or wherein the reaction components are used in the form of their salts or optically pure material. Compounds of the invention and intermediates can also be converted into each other according to methods generally known to those skilled in the art.

Pharmacology and Utility

The present invention provides a method of treating, ameliorating or preventing arthritis or joint injury in a subject in need thereof, the method including administering to the subject a therapeutically effective amount of a compound of the invention, wherein the subject has or is at risk of joint damage or arthritis. The invention also provides a method of treating, ameliorating or preventing arthritis or joint injury in a human patient, the method comprising: administering orally the patient a composition comprising an effective amount of a compound of the invention, thereby treating, ameliorating or preventing arthritis or joint injury in the patient. In some embodiments, the patient has arthritis or joint injury. In some embodiments, the individual does not have, but is at risk for, arthritis or joint injury. In some embodiments, the arthritis is osteoarthritis, trauma arthritis, or autoimmune arthritis.

The compounds of the present invention are also useful for inducing hyaline cartilage production, comprising contacting chondrogenic progenitor cells (CPC) with a therapeutically effective amount of a compound of Formula (1) or sub-formulae thereof, optionally in combination with a second therapeutic agent; thereby inducing hyaline cartilage production. In a non-limiting embodiment, hyaline cartilage production is induced by preventing chondrocyte hypertrophy of chondrocytic progenitor cells. In another non-limiting embodiment, hyaline cartilage production is induced by inducing differentiation of chondrogenic progenitor cells into mature chondrocytes, particularly, mature chondrocytes producing hyaline cartilage extracellular matrix.

CPCs can differentiate into different types of cells including, but not limited to, osteoblasts, hyaline chondrocytes and hypertrophic chondrocytes. Differentiation is the process by which a specialized cell type is formed from a less specialized cell type, for example, a chondrocyte from a chondrogenic progenitor. In some embodiments, the method is performed in vitro. In some embodiments, the method is performed in vivo in a mammal and the progenitor cells are present in the mammal.

Inducing chondrocyte differentiation of chondrogenic progenitor can be accomplished using any suitable amount of a compound of the present invention. In some embodiment, the compound of the present invention can be present in an amount form about 0.1 mg to about 10000 mg, e.g., 1.0 mg to 1000 mg, e.g., 10 mg to 500 mg, according to the particular application and potency of the active component. In some embodiments, the compounds of the present invention can be administered orally once daily at a dose of 1 mg/kg to about 300 mg/kg. Treatment duration can vary from a week or less to chronic treatment in severe osteoarthritis.

It is contemplated that compounds, compositions, and methods of the present invention may be used to treat, ameliorate or prevent any type of articular cartilage damage (e.g., joint damage or injury) including, for example, damage arising from a traumatic event or tendon or ligament tear. In some embodiments, the compounds or compositions of the invention are administered to prevent or ameliorate arthritis or joint damage, for example where there is a genetic or family history of arthritis or joint damage or joint injury or prior or during joint surgery. In some embodiments, compounds, compositions and methods are used to treat joint damage. In particular embodiments, the joint damage is traumatic joint injury. In other embodiments, the joint damage is damage arising from age or inactivity. In yet other embodiments, the joint damage is damage arising from an autoimmune disorder. In other embodiments, the joint damage is damage arising from a metabolic disorder (e.g. diabetes). In some embodiments of the invention, compounds, compositions, and methods of the present invention may be used to treat, ameliorate or prevent osteoarthritis. In some embodiments, the compounds, compositions and methods are used to ameliorate or prevent arthritis in a subject at risk of having or acquiring arthritis. In some embodiments, the compounds, compositions and methods are used to ameliorate or prevent joint damage in a subject at risk of having or acquiring joint damage.

In some embodiments, compounds, compositions, and methods of the present invention are useful for stimulating hyaline cartilage production in cartilagenous tissues that have been damaged, e.g., due to traumatic injury or chondropathy. In particular embodiments compounds, compositions, and methods of the present invention are useful for treatment of cartilage damage in joints, e.g., at articulated surfaces, e.g., spine, shoulder, elbow, wrist, joints of the fingers, hip, knee, ankle, and joints of the feet. Examples of diseases or disorders that may benefit from treatment include osteoarthritis, rheumatoid arthritis, other autoimmune diseases, or osteochondritis dessicans. In addition, cartilage damage or disruption occurs as a result of certain genetic or metabolic disorders, cartilage malformation is often seen in forms of dwarfism in humans, and/or cartilage damage or disruption is often a result of reconstructive surgery; thus compounds, compositions, and methods would be useful therapy in these patients, whether alone or in connection with other approaches.

It is further contemplated that compounds, compositions, and methods of the present invention may be used to treat, ameliorate or prevent various cartilaginous disorders and/or associated symptoms or effects of such conditions. Exemplary conditions or disorders for treatment, amelioration and/or prevention with compounds, compositions, and methods of the invention, include, but are not limited to systemic lupus erythematosis, rheumatoid arthritis, juvenile chronic arthritis, osteoarthritis, degenerative disc disease, spondyloarthropathies, Ehlers Danlos syndrome, systemic sclerosis (scleroderma) or tendon disease. Other conditions or disorders that may benefit from treatment with compounds for amelioration of associated effects include idiopathic inflammatory myopathies (dermatomyositis, polymyositis), Sjogren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barr syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease.

It is contemplated that compounds and/or compositions of the present invention can promote expression of collagen in human dermal fibroblast. Collagen is the major structural component of the dermi. Collagen is vital for skin health and has been widely used in dermal treatment of wrinkles and skin aging, and as a healing aid for bum patients. Collagen is produced in fibroblast, and both human and bovine collagen is widely used. The invention therefore provides a method of increasing production of collagen in fibroblast by contacting the fibroblasts with a compound or composition of the invention, thereby increasing the production of collagen in the fibroblast. The contacting may be in vivo by direct injection of the compound in the areas to be treated. The contacting may be in vitro into a population of fibroblasts.

Pharmaceutical Compositions, Dosage and Administration

In another aspect, the present invention provides a pharmaceutical composition comprising a compound of the present invention, or a pharmaceutically acceptable salt thereof, and a pharmaceutically acceptable carrier. In a further embodiment, the composition comprises at BO least two pharmaceutically acceptable carriers, such as those described herein. The pharmaceutical composition can be formulated for particular routes of administration such as oral administration, parenteral administration (e.g. by injection, infusion, transdermal or topical administration), and rectal administration. Topical administration may also pertain to inhalation or intranasal application. The pharmaceutical compositions of the present invention can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:
  a) diluents, e.g., lactose, dextrose, sucrose, mannitol, sorbitol, cellulose and/or glycine;
  b) lubricants, e.g., silica, talcum, stearic acid, its magnesium or calcium salt and/or polyethyleneglycol; for tablets also
  c) binders, e.g., magnesium aluminum silicate, starch paste, gelatin, tragacanth, methylcellulose, sodium carboxymethylcellulose and/or polyvinylpyrrolidone; if desired
  d) disintegrants, e.g., starches, agar, alginic acid or its sodium salt, or effervescent mixtures; and
  e) absorbents, colorants, flavors and sweeteners.

In general, compounds of the invention will be administered in therapeutically effective amounts via any of the usual and acceptable modes known in the art, either singly or in combination with one or more therapeutic agents. In some embodiments, compounds and compositions of the present invention are applied by direct injection into the synovial fluid of a joint, systemic administration (oral or intravenously) or directly into a cartilage defect, either alone or complexed with a suitable carrier for extended release of the compound. In some embodiments, compounds or compositions are administered in a biocompatible matrix or scaffold.

Compounds, compositions, and methods of the present invention can also be used in conjunction with a surgical procedure at an affected joint. Administration of a compounds or composition of the invention may occur prior to, during or in conjunction with, and/or after a surgical procedure. For example, compounds, compositions and methods of the invention can be used to expand chondrocyte populations in culture for autologous or allogenic chondrocyte implantation (ACI). Chondrocytes can be optionally implanted with concurrent treatment consisting of administration of compounds and compositions of the present invention. In these procedures, for example, chondrocytes can be harvested arthroscopically from an uninjured minor load-bearing area of a damaged joint, and can be cultured in vitro, optionally in the presence of compounds and compositions of the present invention and/or other growth factors to increase the number of cells prior to transplantation. Expanded cultures are then optionally admixed with compounds and compositions of the present invention and/or placed in the joint space or directly into the defect. In certain embodiments, expanded cultures (optionally with compounds of the present invention) are placed in the joint space suspended in a matrix or membrane.

In other embodiments, compounds and compositions of the present invention can be used in combination with one or more periosteal or perichondrial grafts that contain cartilage forming cells and/or help to hold the transplanted chondrocytes or chondrocyte precursor cells in place. In some embodiments, compounds and compositions of the present invention are used to repair cartilage damage in conjunction with other procedures, including but not limited to lavage of a joint, stimulation of bone marrow, abrasion arthroplasty, subchondral drilling, or microfracture of proximal subchondral bone. Optionally, following administration of compounds and compositions of the present invention and growth of cartilage, additional surgical treatment may be beneficial to suitably contour newly formed cartilage surface(s).

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutics By active or enhances the therapeutic activity when administered to a patient in combination with a compound of the invention.

In one embodiment, the invention provides a pharmaceutical composition comprising a compound of Formula (1) or sub-formulae thereof, and a second therapeutic agent(s). The second agent may be one or more additional chondrocyte differentiation agents. Examples of chondrocyte differentiation agent include but are not limited to angiopoietin-like 3 protein (ANGPTL3), insulin growth factor (IGF1), SM04690 (Wnt inhibitor), Janus kinase inhibitors (such as ruxolitinib, tofacitinib, baricitinib), oral salmon calcitonin, SD-6010 (iNOS inhibitor), vitamin D3 (cholecalciferol), collagen hydrolyzate, bone morphogenetic protein 7 (BMP7), rusalatide acetate, avocado soy unsaponifiables (ASU), a steroid, a non-steroidal anti-inflammatory agent (NSAID), or hyaluronic acid, kartogenin, TPX-100, and a chondrocyte differentiation agent having Formula (I) or sub-formulae thereof as described in WO 2015/175487. The compound Formula (1) or sub-formulae thereof and the other therapeutic agent can be provided together in the same pharmaceutical composition, or in separate form, e.g. in the form of a kit, for simultaneous, separate or sequential use in therapy. In one embodiment, the therapy is the treatment of joint damage resulting from joint injury or arthritis.

Optionally, the pharmaceutical composition may comprise a pharmaceutically acceptable carrier, as described above. The pharmaceutical composition or combination of the present invention can be in unit dosage of about 1-1000 mg of active ingredients) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution.

In one embodiment, the invention provides a kit comprising two or more separate pharmaceutical compositions, at least one of which contains a compound of Formula (1) or sub-formulae thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

EXAMPLES

Temperatures are given in degrees Celsius. The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Unless otherwise specified, starting materials are generally available from commercial sources, such as but not limited to, TCI Fine Chemical (Japan), Aurora Fine Chemicals LLC (San Diego, CA), FCH Group (Ukraine), Aldrich Chemicals Co. (Milwaukee, Wis.), Acros Organics (Fairlawn, N.J.), Maybridge Chemical Company, Ltd. (Cornwall, England), Matrix Scientific (USA), Enamine Ltd (Ukraine), Combi-Blocks, Inc. (San Diego, CA), Oakwood Products, Inc. (USA), Apollo Scientific, Ltd. (UK).

The Examples herein merely illuminate the invention and does not limit the scope of the invention otherwise claimed. Further, the compounds of the present invention can be produced by organic synthesis methods known to one of ordinary skill in the art as shown in the following examples. Where desired, conventional protecting groups are used to protect reactive functional groups in accordance with standard practice, for example, see T. W. Greene and P. G. M. Wilts in "Protecting Groups in Organic Synthesis", John Wiley and Sons, 1991.

Abbreviations

Abbreviations as used herein, are defined as follows: "1×" for once, "2×" for twice, "3×" for thrice. "° C." for degrees Celsius, "aq" for aqueous, "FCC" for flash column chromatography, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" or "hrs" for hour or hours, "RT" for room temperature, "ON" for overnight, "atm" for atmosphere, "psi" for pounds per square inch, "conc." for concentrate, "sat" or "sat'd" for saturated, "MW" for molecular weight, "mw" or "µwave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LCMS" or "LC-MS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, "ee" for "enantiomeric excess" and "α", "β", "R", "r", "S", "s", "E", and "Z" are stereochemical designations familiar to one skilled in the art.

The following abbreviations used herein below have the corresponding meanings:

Δ heat
AcOH acetic acid
AgNO$_3$ silver nitrate
app apparent
ATP adenosine 5'-triphosphate
BINAP racemic 2,2'-bis(diphenylphosphino)-1,1-binaphthyl
BOC tertiary butyl carboxy
BSA bovine serum albumin
CDCl$_3$ chloroform-d
CO$_2$ carbon dioxide
dd doublet of doublets
DCM dichloromethane
DMEM Dulbecco Modified Eagle Medium
DMSO dimethylsulfoxide
EDTA ethylenediamine tetraacetic acid
ESI electrospray ionization
EtOAc ethyl acetate
EtOH ethanol
FBS fetal bovine serum
K$_2$CO$_3$ potassium carbonate
LiHMDS lithium bis(trimethylsilyl)amide
Me$_3$Al trimethylaluminum
MeOH methanol
MgSO$_4$ magnesium sulfate
MHz megahertz
m/z mass to charge ratio
NaHCO$_3$ sodium bicarbonate
Na$_2$SO$_4$ sodium sulfate
NBS N-bromosuccinimide
NH$_4$Cl ammonium chloride
PBS phosphate-buffered saline
PE petroleum ether
ppm parts per million
rac racemic
Rt retention time
SFC Supercritical Fluid Chromatography
TBAF tetrabutylammonium fluoride
TFA trifluoroacetic acid
THF tetrahydrofuran
Tris.HCl aminotris(hydroxymethyl)methane hydrochloride
UV ultraviolet The following Examples have been prepared, isolated, and characterized using the methods disclosed herein. The following examples demonstrate a partial scope of the disclosure and are not meant to be limiting of the scope of the disclosure.

Unless specified otherwise, starting materials are generally available from non-excluding commercial sources such as but not limited to TCI Fine Chemical (Japan), Aurora Fine Chemicals BO LLC (San Diego, CA), FCH Group (Ukraine), Aldrich Chemicals Co. (Milwaukee, Wis.), Acres Organics (Fairiawn, N.J.), Maybridge Chemical Company, Ltd. (Cornwall, England), Matrix Scientific (USA), Enamine Ltd (Ukraine), Combi-Blocks, Inc. (San Diego, CA). Oakwood Products, Inc. (USA), Apollo Scientific, Ltd. (UK).

LCMS Methods Employed in Characterization of Examples

Analytical LC/MS was carried out on Agilent systems using ChemStation software and on Waters Acquity UPLC instruments. The Agilent system consists of:
Agilent G1312 Binary Pump
Agilent G1367 Well Plate Autosampler
Agilent G1316 Thermostated Column Compartment
Agilent G1315 Diode Array Detector
Agilent 6140/6150 Mass Spectrometer
SOFTA Evaporative Light Scattering Detector Typical method conditions are as follows:
Flow rate: 0.9 mL/min
Column: 1.8 μm 2.1×50 mm Waters Acquity HSS T3 C18 column
Mobile Phase A: Water+0.05% TFA
Mobile Phase B: Acetonitrile+0.035% TFA
Run Time: 2.25 minutes
Method A: The system runs a gradient from 10% B to 90% B in 1.35 minutes. A 0.6 minute wash at 100% B follows the gradient. The remaining duration of the method returns the system to initial conditions. Unless otherwise stated the examples provided are characterized using method A.

The system Waters system consists of:
Acquity Binary Gradient Manager with Degasser
Acquity FTN Sample Manager
Acquity Column Manager set at 50° C.
Acquity Photodiode Array Detector (PDA)
Acquity Evaporative Light Scattering Detector (ELSD)
Acquity QDa Mass Detector Typical method conditions are as follows:
Flow rate: 1.0 mL/min
Column: 1.8 μm 2.1×30 mm Waters Acquity HSS T3 C18
Mobile Phase A: Water+0.1% formic acid
Mobile Phase B: Acetonitrile+0.1% formic add
Run Time: 2.5 minutes
Method B: The system runs a gradient from 5% B to 100% B in 1.9 minutes. A 0.4 minute wash at 100% B follows the gradient. The remaining duration of the method returns the system to initial conditions.
Method C: The system runs a gradient from 5% B to 100% B in 0.7 minutes. A 0.3 minute wash at 100% B follows the gradient. The remaining duration of the method returns the system to initial conditions.

NMR Methods Employed in Characterization of Examples

Proton spectra are recorded on a Bruker AVANCE II400 MHz with 5 mm QNP Cryoprobe or a Bruker AVANCE III 500 MHz with 5 mm QNP probe unless otherwise noted. Chemical shifts are reported in ppm relative to dimethyl sulfoxide (δ 2.50), chloroform (δ 7.26), methanol (δ 3.34), dichloromethane (δ 5.32), acetone (δ 2.05), or acetonitrile (δ 1.94). A small amount of the dry sample (2-5 mg) is dissolved in an appropriate deuterated solvent (0.6 mL).

ISCO Methods Employed in Purification of Examples

ISCO flash chromatography is performed on Teledyne COMBIFLASH® system with prepacked silica RediSep® column.

Chiral Preparative HPLC Methods Employed in Purification of Examples

SFC chiral screening is carried out on a Thar Instruments Prep Investigator system coupled to a Waters ZQ mass spectrometer. The Thar Prep Investigator system consists of:
Leap HTC PAL autosampler
Thar Fluid Delivery Module (0 to 10 mL/min)
Thar SFC 10 position column oven
Waters 2996 PDA
Jasco CD-2095 Chiral Detector
Thar Automated Back Pressure Regulator All of the Thar components are part of the SuperPure Discovery Series line. The system flows at 2 mL/min (4 mL/min for the WhelkO-1 column) and is kept at 30 degrees C. The system back pressure is set to 125 bar. Each sample is screened through a battery of eleven 3 μm columns:
3 μm 4.6×50 mm ChiralPak AD
3 μm 4.6×50 mm ChiralPak OD
3 μm 4.6×50 mm Chiralcel OJ
3 μm 4.6×50 mm ChiralPak IA
3 μm 4.6×50 mm ChiralPak IB
3 μm 4.6×50 mm ChiralPak IC
3 μm 4.6×50 mm ChiralPak IF
3 μm 4.6×50 mm ChiralPak IG
3 μm 4.6×250 mm Whelk 0-1
3 μm 4.6×50 mm ChiralPak AS
3 μm 4.6×50 mm Lux-Cellulose-2

The system runs a gradient from 5% co-solvent to 50% co-solvent in 5 minutes followed by a 0.5 minute hold at 50% co-solvent, a switch back to 5% co-solvent and a 0.25 minute hold at initial conditions. In between each gradient there is a 4 minute equilibration method that flows 5% co-solvent through the next column to be screened. The typical solvents screened are MeOH, MeOH+20 mM $NH_3$, MeOH+0.5% DEA, IPA, and IPA+20 mM $NH_3$.

Once separation is detected using one of the gradient methods an isocratic method can be developed and, if necessary, scaled up for purification on the Thar Prep80 system.

INTERMEDIATES

Intermediate 1b: Methyl 3-bromo-7-oxabicyclo [2.2.1]hepta-2,5-diene-2-carboxylate

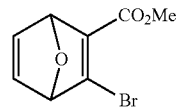

1b

Step A: To a stirring solution of methyl propiolate (1a, 200 g, 2.38 mol, 198 mL) in acetone (2.50 L) was added $AgNO_3$ (36.4 g, 214 mmol, 36.0 mL). After 5 min. NBS (445 g, 2.50 mol) was added portionwise, and the reaction mixture was stirred at 25° C. for 12 h. The reaction mixture was filtered, the filtrate was concentrated, and the residue was triturated with 10% EtOAc/PE (1500 mL), and the filtrate was concentrated again. The residue was purified by column chromatography (0-5% EtOAc/PE) to give methyl 3-bromopropiolate as a yellow oil which was used for the next step directly.

A solution of methyl 3-bromopropiolate (200 g, 1.23 mol) and furan (419 g, 6.15 mol, 445 mL) in toluene (2.50 L) was degassed by passing nitrogen gas through the reaction vessel for 2 min at 0° C., then the reaction mixture was warmed to 90° C. for 72 hour to give a black solution. The reaction mixture was concentrated and the residue was purified by flash column chromatography (2-5% EtOAc/PE) to give methyl 3-bromo-7-oxabicyclo[2.2.1]hepta-2,5-diene-2-carboxylate. Four batches were purified separately and combined to afford methyl 3-bromo-7-oxabicyclo[2.2.1]hepta-2,5-diene-2-carboxylate (1b) as a yellow oil. $^1$H NMR (400 MHz, $CDCl_3$) δ 7.25-7.17 (m, 2H), 5.70 (t, J=1.6 Hz, 1H), 5.33 (t, J=1.7 Hz, 1H), 3.82-3.75 (m, 3H).

Intermediate 1c: Methyl (1R,4S,5S)-3-bromo-5-hydroxy-7-oxabicyclo[2.2.1]hept-2-ene-2-carboxylate

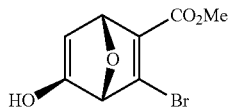

Step B: A solution of methyl 3-bromo-7-oxabicyclo[2.2.1]hepta-2,5-diene-2-carboxylate (1b, 130 g, 563 mmol, 1.00 eq) in THF (800 mL) was treated with BH$_3$-THF (1 M, 563 mL, 563 mmol) and was stirred at 0° C. for 2 hr. A solution of phosphate buffer, pH=7 (1000 mL) was added dropwise, followed by a mixture of H$_2$O$_2$ (270 mL, 2.81 mol, 30% v/v) and NaOH (2 M, 338 mL, 676 mmol) was added slowly and the mixture was stirred at 0° C. for 2 hr. The reaction mixture was extracted with ethyl acetate (500 mL 3×), and the combined organic layers were washed with sat. aq. NaHSO$_3$ solution (500 mL 2×), brine (500 mL), dried (Na$_2$SO$_4$) and concentrated. The residue was purified by column chromatography (2-50% EtOAc/PE) to give the desired product. Two batches were combined and carefully repurified by FCC to afford 1c as a 3:1 mixture of alcohol regioisomers favoring the 5-hydroxy product as a yellow solid. The product was recrystallized from EtOAc/heptanes to afford intermediate 1c as a 12:1 mixture of alcohol regioisomers as a white solid. $^1$H NMR (400 MHz, CDCl$_3$) δ 5.25-5.02 (m, 1H), 4.94-4.74 (m, 1H), 4.23-4.14 (m, 1H), 3.80-3.78 (m, 3H), 2.14-2.01 (m, 1H), 1.91-1.81 (m, 1H), 1.69-1.60 (m, 1H).

Intermediate 1d: Methyl (1R,4S,5S)-3-bromo-5-((tert-butyldimethylsilyl)oxy)-7-oxabicyclo[2.2.1]hept-2-ene-2-carboxylate

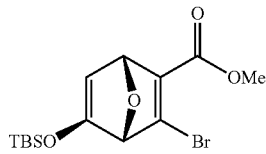

Step C: A solution of intermediate 1c (29.8 g, 120 mmol) and triethylamine (50.1 ml, 359 mmol) in anhydrous THF (265 ml) at −78° C. was treated dropwise with tert-butyldimethylsilyl trifluoromethanesulfonate (33.0 ml, 144 mmol). The reaction mixture was stirred at this temperature for 20 min, then the reaction mixture was slowly allowed to warm up to room temperature and was stirred for 1 h. The reaction mixture was diluted with Et$_2$O, washed with 1.0 M HCl and brine, dried (Na$_2$SO$_4$), filtered, and concentrated to afford a colorless oil. The residue was recrystallized from EtOH and water and was dried under vacuum to afford intermediate 1d. $^1$H NMR (400 MHz, CDCl$_3$) δ 5.08 (dd, J=4.4, 1.3 Hz, 1H), 4.54 (d, J=1.3 Hz, 1H), 4.04 (dd, J=6.6, 2.3 Hz, 1H), 3.66 (s, 3H), 1.88 (dd, J=12.0, 6.6 Hz, 1H), 1.54 (ddd, J=12.0, 4.4, 2.3 Hz, 1H), 0.79 (s, 9H), −0.01 (d, J=4.2 Hz, 6H).

EXAMPLES

Example 1: rac-(1R,2R,4S,5R,6S)-4-(2-fluoropyridin-4-yl)-6-hydroxy-N-(4-(trifluoromethyl)pyridin-2-yl)-8-oxatricyclo[3.2.1.02,4]octane-2-carboxamide

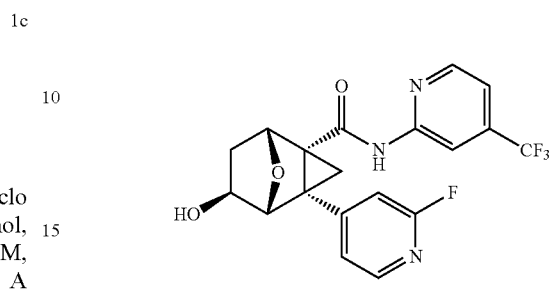

Title compound was prepared from methyl (1R,4S,5S)-3-bromo-5-((tert-butyldimethylsilyl)oxy)-7-oxabicyclo[2.2.1]hept-2-ene-2-carboxylate (Intermediate 1d) using Steps D-F as in Scheme 1.

Step D: A solution of methyl (1R,4S,5S)-3-bromo-5-((tert-butyldimethylsilyl)oxy)-7-oxabicyclo[2.2.1]hept-2-ene-2-carboxylate (1d, 4 g, 11.0 mmol), (2-fluoropyridin-4-yl)boronic acid (1.71 g, 12.1 mmol), Na$_2$CO$_3$ (8.26 ml, 16.5 mmol), and palladium-tetrakis(triphenylphosphine) (0.636 g, 0.550 mmol) in 1,4-dioxane (55 ml) was purged with nitrogen and was warmed at reflux for 2 h. The reaction mixture was cooled to RT, diluted with EtOAc, washed with water and brine, dried (Na$_2$SO$_4$), filtered, and concentrated. The resulting residue was purified by FCC (0-60% EtOAc/heptanes) to afford methyl (1R,4R,5S)-5-((tert-butyldimethylsilyl)oxy)-3-(2-fluoropyridin-4-yl)-7-oxabicyclo[2.2.1]hept-2-ene-2-carboxylate. LC-MS: Rt=1.84 min; MS m/z [M+H]$^+$ 380.3.

Step E: A solution of trimethylsulfoxonium iodide (1390 mg, 6.31 mmol) in DMSO (21 mL) was treated with NaH (252 mg, 6.31 mmol) and was stirred at room temperature for 30 min. Methyl(1R,4R,5S)-5-((tert-butyldimethylsilyl)oxy)-3-(2-fluoropyridin-4-yl)-7-oxabicyclo[2.2.1]hept-2-ene-2-carboxylate (798 mg, 2.10 mmol) in DMSO (21 mL) was added dropwise and the resulting mixture was warmed at 50° C. for 5 min. The reaction mixture was diluted with EtOAc, washed with water 3× and brine, dried (Na$_2$SO$_4$), filtered, and concentrated. The resulting residue was purified by FCC (0-100% EtOAc/heptanes) to afford methyl (1R,2R,4S,5R,6S)-6-((tert-butyldimethylsilyl)oxy)-4-(2-fluoropyridin-4-yl)-8-oxatricyclo[3.2.1.02,4]octane-2-carboxylate. Method B: LC-MS: Rt=0.78 min; MS m/z [M+H]$^+$ 394.2.

Step F: A solution of methyl (1R,2R,4S,5R,6S)-6-((tert-butyldimethylsilyl)oxy)-4-(2-fluoropyridin-4-yl)-8-oxatricyclo[3.2.1.02,4]octane-2-carboxylate (15 mg, 0.038 mmol) and 4-(trifluoromethyl)pyridin-2-amine (6.8 mg, 0.042 mmol) in THF (0.4 mL) at RT was treated with 1 M LiHMDS in THF (76 µl, 0.076 mmol) and was stirred at RT for 14 h, 1 M TBAF in THF (95 µl, 0.095 mmol) was added and the reaction was warmed at 60° C. for 2 h. The reaction mixture was cooled to RT and was loaded onto a column and was purified directly by FCC (0-100% EtOAc/heptanes) to afford rac-(1R,2R,4S,5R,6S)-4-(2-fluoropyridin-4-yl)-6-hydroxy-N-(4-(trifluoromethyl)pyridin-2-yl)-8-oxatricyclo[3.2.1.02,4]octane-2-carboxamide. LC-MS: Rt=1.29 min; MS m/z [M+H]$^+$ 410.2. $^1$H NMR (400 MHz, Acetonitrile-d$_3$) δ 8.81 (s, 1H), 8.54-8.48 (m, 1H), 8.37-8.33 (m, 1H), 8.12-8.06 (m, 1H), 7.40-7.35 (m, 1H), 7.13-7.07 (m, 1H), 6.95-6.91 (m, 1H), 4.74 (d, J=4.9 Hz, 1H), 4.39 (s, 1H), 4.31-4.25 (m, 1H), 3.11-3.00 (m, 1H), 2.84-2.76 (m, 1H), 1.95-1.92 (m, 1H), 1.62-1.56 (m, 1H), 1.39-1.35 (m, 1H).

Example 2-82 described infra were synthesized according to the protocol described for Example 1 using methyl (1R,4S,5S)-3-bromo-5-(((tert-butyldimethylsilyl)oxy)-7-oxabicyclo[2.2.1]hept-2-ene-2-carboxylate (Intermediate 1d) and various boronic acids/esters in Step D and various anilines in Step F.

Example 2: rac-i 1R,2R,4S,5R,6S)—N-(3-fluoro-4-(trifluoromethyl)phenyl)-4-(2-fluoropyridin-4-yl)-6-hydroxy-8-oxatricyclo[3.2.1.02,4]octane-2-carboxamide

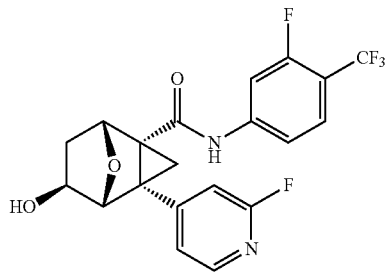 [SMILES: O=C(Nc1ccc(C(F)(F)F)c(F)c1)[C@]12C[C@@]1(c1ccnc(F)c1)[C@H]1O[C@@H]2C[C@@H]1O]

LC-MS: Rt=1.42 min; MS m/z [M+H]+ 427.2. 1H NMR (400 MHz, Acetonitrile-d3) δ 8.63 (s, 1H), 8.10-8.07 (m, 1H), 7.75-7.69 (m, 1H), 7.64-7.58 (m, 1H), 7.43-7.39 (m, 1H), 7.09-7.06 (m, 1H), 6.91-6.89 (m, 1H), 4.70 (d, J=4.8 Hz, 1H), 4.39 (s, 1H), 4.28-4.22 (m, 1H), 3.07-3.03 (m, 1H), 2.85-2.79 (m, 1H), 1.93-1.91 (m, 3H), 1.61-1.54 (m, 1H), 1.36-1.32 (m, 1H).

Example 3: rac-(1R,2R,4S,5R,6S)—N-(3-chloro-4-(trifluoromethyl)phenyl)-4-(2-fluoropyridin-4-yl)-6-hydroxy-8-oxatricyclo[3.2.1.02,4]octane-2-carboxamide

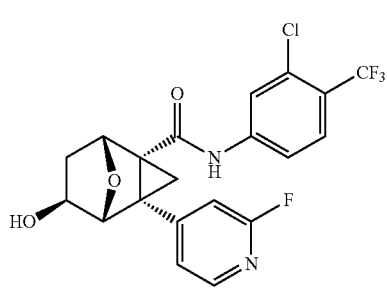 [SMILES: O=C(Nc1ccc(C(F)(F)F)c(Cl)c1)[C@]12C[C@@]1(c1ccnc(F)c1)[C@H]1O[C@@H]2C[C@@H]1O]

LC-MS: Rt=1.48 min; MS m/z [M+H]+ 443.1. 1H NMR (400 MHz, Acetonitrile-d3) δ 8.58 (s, 1H), 8.11-8.08 (m, 1H), 7.93-7.89 (m, 1H), 7.73-7.68 (m, 1H), 7.63-7.58 (m, 1H), 7.10-7.07 (m, 1H), 6.93-6.89 (m, 1H), 4.70 (d, J=4.8 Hz, 1H), 4.38 (s, 1H), 4.28-4.22 (m, 1H), 3.07-3.03 (m, 1H), 2.85-2.79 (m, 1H), 1.93-1.91 (m, 1H), 1.61-1.55 (m, 1H), 1.36-1.32 (m, 1H).

Example 4: rac-(1R,2R,4S,5R,6S)—N-(6-chloro-4-(trifluoromethyl)pyridin-2-yl)-4-(2-fluoropyridin-4-yl)-6-hydroxy-8-oxatricyclo[3.2.1.02,4]octane-2-carboxamide

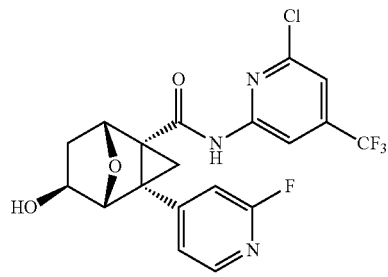 [SMILES: O=C(Nc1cc(C(F)(F)F)cc(Cl)n1)[C@]12C[C@@]1(c1ccnc(F)c1)[C@H]1O[C@@H]2C[C@@H]1O]

LC-MS: Rt=1.46 min; MS m/z [M+H]+ 444.2. 1H NMR (400 MHz, Acetonitrile-d3) δ 8.93 (s, 1H), 8.31-8.28 (m, 1H), 8.11-8.08 (m, 1H), 7.46-7.44 (m, 1H), 7.10-7.07 (m, 1H), 6.93-6.90 (m, 1H), 4.74 (d, J=4.8 Hz, 1H), 4.38 (s, 1H), 4.29-4.24 (m, 1H), 3.08-3.05 (m, 1H), 2.80-2.73 (m, 1H), 1.97-1.95 (m, 1H), 1.62-1.56 (m, 1H), 1.39-1.36 (m, 1H).

Example 5: rac-/1R,2R,4S,5R,6S)—N-(5-chloro-4-(trifluoromethyl)pyridin-2-yl)-4-(2-fluoropyridin-4-yl)-6-hydroxy-8-oxatricyclo[3.2.1.02,4]octane-2-carboxamide

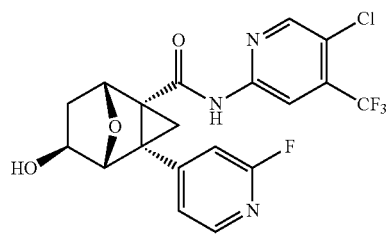 [SMILES: O=C(Nc1cc(C(F)(F)F)c(Cl)cn1)[C@]12C[C@@]1(c1ccnc(F)c1)[C@H]1O[C@@H]2C[C@@H]1O]

LC-MS: Rt=1.42 min; MS m/z [M+H]+ 444.2. 1H NMR (400 MHz, Acetonitrile-d3) δ 8.90 (s, 1H), 8.52-8.45 (m, 2H), 8.11-8.07 (m, 1H), 7.10-7.07 (m, 1H), 6.94-6.90 (m, 1H), 4.74 (d, J=4.9 Hz, 1H), 4.39 (s, 1H), 4.29-4.24 (m, 1H), 3.10-3.02 (m, 1H), 2.81-2.74 (m, 1H), 1.97-1.92 (m, 1H), 1.62-1.55 (m, 1H), 1.39-1.36 (m, 1H).

Example 6: rac-(1R,2R,4S,5R,6S)—N-(6-cyclopropyl-4-(trifluoromethyl)pyridin-2-yl)-4-(2-fluoropyridin-4-yl)-6-hydroxy-8-oxatricyclo[3.2.1.02,4]octane-2-carboxamide

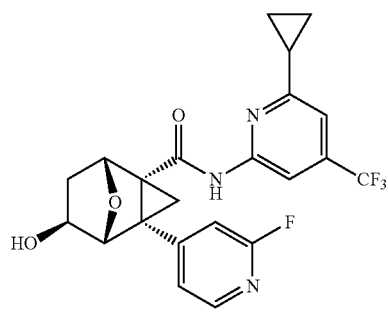 [SMILES: O=C(Nc1cc(C(F)(F)F)cc(C2CC2)n1)[C@]12C[C@@]1(c1ccnc(F)c1)[C@H]1O[C@@H]2C[C@@H]1O]

LC-MS: Rt=1.51 min; MS m/z [M+H]+ 450.2. ¹H NMR (400 MHz, Acetonitrile-d₃) δ 8.61 (s, 1H), 8.11-8.07 (m, 1H), 8.05-8.02 (m, 1H), 7.29-7.25 (m, 1H), 7.12-7.08 (m, 1H), 6.94-6.89 (m, 1H), 4.71 (d, J=4.9 Hz, 1H), 4.37 (s, 1H), 4.29-4.23 (m, 1H), 3.07-3.02 (m, 1H), 2.82-2.75 (m, 1H), 2.12-2.07 (m, 1H), 1.97-1.92 (m, 1H), 1.61-1.55 (m, 1H), 1.35-1.32 (m, 1H), 1.02-0.96 (m, 4H).

Example 7: rac-(1R,2R,4S,5R,6S)-4-(2-fluoropyridin-4-yl)-6-hydroxy-N-(6-methyl-4-(trifluoromethyl)pyridin-2-yl)-8-oxatricyclo[3.2.1.0²,⁴]octane-2-carboxamide

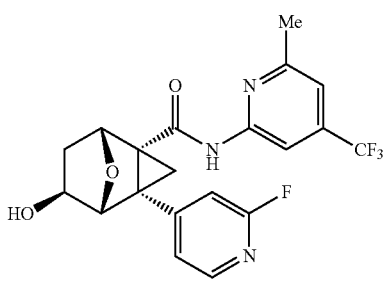 [SMILES: Cc1cc(C(F)(F)F)cc(NC(=O)[C@]23C[C@@]2(c2ccnc(F)c2)[C@H]2O[C@@H]3C[C@@H]2O)n1]

LC-MS: Rt=1.38 min; MS m/z [M+H]+ 424.2. ¹H NMR (400 MHz, Acetonitrile-d₃) δ 8.71 (s, 1H), 8.16-8.12 (m, 1H), 8.11-8.06 (m, 1H), 7.27-7.24 (m, 1H), 7.12-7.08 (m, 1H), 6.94-6.90 (m, 1H), 4.73 (d, J=4.8 Hz, 1H), 4.38 (s, 1H), 4.30-4.24 (m, 1H), 3.09-3.05 (m, 1H), 2.83-2.76 (m, 1H), 2.50 (s, 3H), 1.96-1.92 (m, 8H), 1.63-1.55 (m, 1H), 1.38-1.33 (m, 1H).

Example 8; rac-(1R,2R,4S,5R,6S)—N-(6-ethoxy-4-(trifluoromethyl)pyridin-2-yl)-4-(2-fluoropyridin-4-yl)-6-hydroxy-8-oxatricyclo[3.2.1.0²,⁴]octane-2-carboxamide

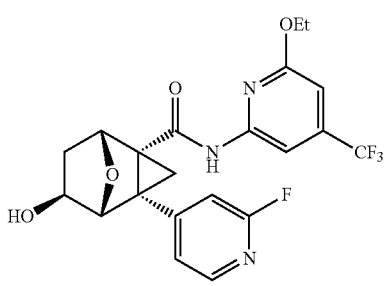

LC-MS: Rt=1.52 min; MS m/z [M+H]+ 454.2. ¹H NMR (400 MHz, Acetonitrile-d₃) δ 8.68 (s, 1H), 8.11-8.07 (m, 1H), 7.88-7.84 (m, 1H), 7.12-7.08 (m, 1H), 6.94-6.91 (m, 1H), 6.76-6.73 (m, 1H), 4.73 (d, J=4.8 Hz, 1H), 4.38 (s, 1H), 4.34 (q, J=7.1 Hz, 2H), 4.29-4.23 (m, 1H), 3.08-3.03 (m, 1H), 2.82-2.75 (m, 1H), 1.95-1.92 (m, 1H), 1.62-1.55 (m, 1H), 1.37-1.33 (m, 4H).

Example 9: rac-(1R,2R,4S,5R,6S)-4-(2-fluoropyridin-4-yl)-6-hydroxy-N-(3-(trifluoromethyl)phenyl)-8-oxatricyclo[3.2.1.0²,⁴]octane-2-carboxamide

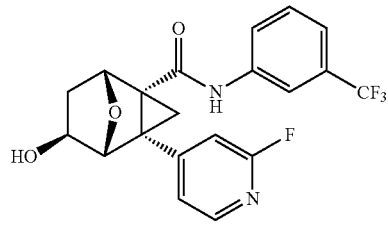 [SMILES: O=C(Nc1cccc(C(F)(F)F)c1)[C@]12C[C@@]1(c1ccnc(F)c1)[C@H]1O[C@@H]2C[C@@H]1O]

Method C: LC-MS: Rt=0.56 min; MS m/z [M+H]+ 409.1. ¹H NMR (400 MHz, DMSO-cfc) δ 10.15 (s, 1H), 8.16-8.09 (m, 1H), 8.04-7.99 (m, 1H), 7.90-7.83 (m, 1H), 7.60-7.51 (m, 1H), 7.46-7.40 (m, 1H), 7.14-7.09 (m, 1H), 7.04-6.99 (m, 1H), 5.03-4.97 (m, 1H), 4.75-4.70 (m, 1H), 4.42 (s, 1H), 4.16-4.08 (m, 1H), 2.76-2.68 (m, 1H), 1.85-1.79 (m, 1H), 1.50-1.43 (m, 2H).

Example 10: rac-(1R,2R,4S,5R,6S)-4-(2-fluoropyridin-4-yl)-6-hydroxy-N-(2-methyl-3-(trifluoromethyl)phenyl)-8-oxatricyclo[3.2.1.0²,⁴]octane-2-carboxamide

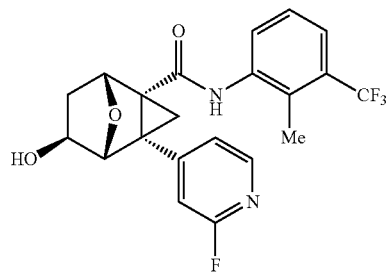 [SMILES: Cc1c(NC(=O)[C@]23C[C@@]2(c2ccnc(F)c2)[C@H]2O[C@@H]3C[C@@H]2O)cccc1C(F)(F)F]

LC-MS: Rt=1.35 min; MS m/z [M+H]+ 423.2. ¹H NMR (400 MHz, Acetonitrile-d₃) δ 8.14-8.11 (m, 1H), 7.95 (s, 1H), 7.60-7.52 (m, 2H), 7.39-7.33 (m, 1H), 7.19-7.15 (m, 1H), 6.99-6.96 (m, 1H), 4.72 (d, J=4.9 Hz, 1H), 4.36 (s, 1H), 4.32-4.26 (m, 1H), 3.04-3.00 (m, 1H), 2.93-2.84 (m, 1H), 2.28 (s, 3H), 1.96-1.91 (m, 1H), 1.65-1.59 (m, 1H), 1.34-1.30 (m, 1H).

Example 11: rac-(1R,2R,4S,5R,6S)-4-(2-fluoropyridin-4-yl)-6-hydroxy-N-(4-methyl-3-(trifluoromethyl)phenyl)-8-oxatricyclo[3.2.1.0²,⁴]octane-2-carboxamide

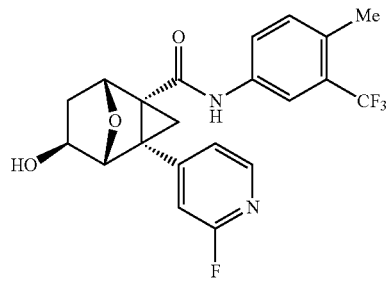 [SMILES: Cc1ccc(NC(=O)[C@]23C[C@@]2(c2ccnc(F)c2)[C@H]2O[C@@H]3C[C@@H]2O)cc1C(F)(F)F]

LC-MS: Rt=1.43 min; MS m/z [M+H]+ 423.2. ¹H NMR (400 MHz, Acetonitrile-d₃) δ 8.37 (s, 1H), 8.10-8.07 (m, 1H), 7.88-7.85 (m, 1H), 7.66-7.61 (m, 1H), 7.34-7.29 (m, 1H), 7.12-7.07 (m, 1H), 6.92-6.89 (m, 1H), 4.68 (d, J=4.8 Hz, 1H), 4.38 (s, 1H), 4.27-4.21 (m, 1H), 3.06-3.01 (m, 1H), 2.91-2.83 (m, 1H), 2.42 (s, 3H), 1.91-1.88 (m, 1H), 1.60-1.54 (m, 1H), 1.33-1.30 (m, 1H).

Example 12: rac-(1R,2R,4S,5R,6S)-4-(2-fluoropyridin-4-yl)-6-hydroxy-N-(3-methyl-5-(trifluoromethyl)phenyl)-8-oxatricyclo[3.2.1.0²,⁴]octane-2-carboxamide

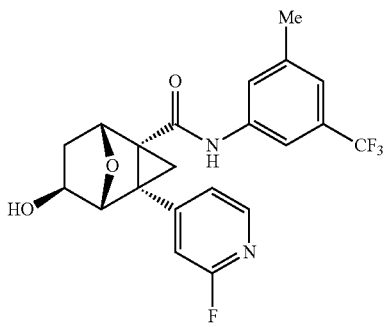

LC-MS: Rt=1.44 min; MS m/z [M+H]+ 423.2. ¹H NMR (400 MHz, Acetonitrile-d₃) δ 8.40 (s, 1H), 8.11-8.06 (m, 1H), 7.76-7.71 (m, 1H), 7.59-7.54 (m, 1H), 7.28-7.23 (m, 1H), 7.12-7.08 (m, 1H), 6.93-6.89 (m, 1H), 4.68 (d, J=4.9 Hz, 1H), 4.38 (s, 1H), 4.28-4.22 (m, 1H), 3.06-3.02 (m, 1H), 2.91-2.82 (m, 1H), 2.38 (s, 3H), 1.92-1.89 (m, 1H), 1.60-1.53 (m, 1H), 1.34-1.31 (m, 1H).

Example 13: rac-(1R,2R,4S,5R,6S)-4-(2-fluoropyridin-4-yl)-6-hydroxy-N-(2-methyl-5-(trifluoromethyl)phenyl)-8-oxatricyclo[3.2.1.0²,⁴]octane-2-carboxamide

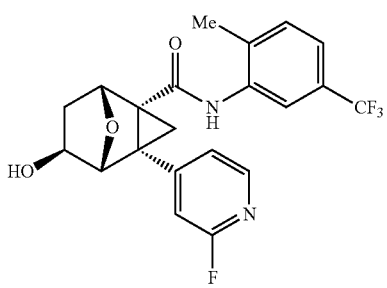 [SMILES: Cc1ccc(C(F)(F)F)cc1NC(=O)[C@]12C[C@@]1(c1ccnc(F)c1)[C@H]1O[C@@H]2C[C@@H]1O]

LC-MS: Rt=1.37 min; MS m/z [M+H]+ 423.2. ¹H NMR (400 MHz, Acetonitrile-d₃) δ 8.14-8.09 (m, 1H), 7.88 (s, 1H), 7.80-7.76 (m, 1H), 7.46-7.39 (m, 2H), 7.19-7.15 (m, 1H), 6.98-6.95 (m, 1H), 4.72 (d, J=4.9 Hz, 1H), 4.36 (s, 1H), 4.32-4.24 (m, 1H), 3.05-3.00 (m, 1H), 2.93-2.85 (m, 1H), 2.25 (s, 3H), 1.93-1.92 (m, 1H), 1.65-1.58 (m, 1H), 1.34-1.31 (m, 1H).

Example 14: rac-(1R,2R,4S,5R,6S)-N-(2-fluoro-3-(trifluoromethyl)phenyl)-4-(2-fluoropyridin-4-yl)-6-hydroxy-8-oxatricyclo[3.2.1.0²,⁴]octane-2-carboxamide

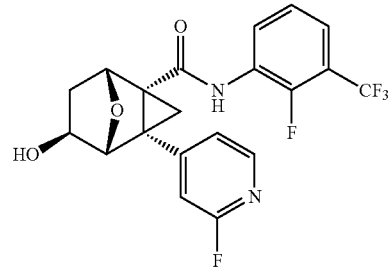 [SMILES: O=C(Nc1cccc(C(F)(F)F)c1F)[C@]12C[C@@]1(c1ccnc(F)c1)[C@H]1O[C@@H]2C[C@@H]1O]

LC-MS: Rt=1.34 min; MS m/z [M+H]+ 427.2. ¹H NMR (400 MHz, Acetonitrile-d₃) δ 8.15-8.07 (m, 2H), 8.04-7.99 (m, 1H), 7.52-7.46 (m, 1H), 7.35-7.28 (m, 1H), 7.16-7.13 (m, 1H), 6.95-6.93 (m, 1H), 4.71 (d, J=4.8 Hz, 1H), 4.38 (s, 1H), 4.29-4.24 (m, 1H), 3.06-3.01 (m, 1H), 2.89-2.80 (m, 1H), 1.95-1.92 (m, 1H), 1.63-1.57 (m, 1H), 1.35-1.33 (m, 1H).

Example 15: rac-(1R,2R,4S,5R,6S)-N-(4-fluoro-3-(trifluoromethyl)phenyl)-4-(2-fluoropyridin-4-yl)-6-hydroxy-8-oxatricyclo[3.2.1.0²,⁴]octane-2-carboxamide

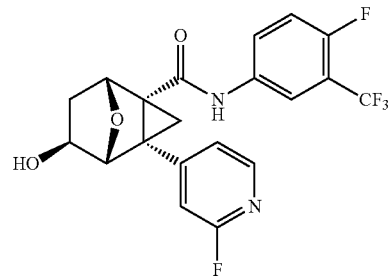 [SMILES: O=C(Nc1ccc(F)c(C(F)(F)F)c1)[C@]12C[C@@]1(c1ccnc(F)c1)[C@H]1O[C@@H]2C[C@@H]1O]

LC-MS: Rt=1.41 min; MS m/z [M+H]+ 427.2. ¹H NMR (400 MHz, Acetonitrile-d₃) δ 8.45 (s, 1H), 8.11-8.07 (m, 1H), 7.95-7.91 (m, 1H), 7.78-7.73 (m, 1H), 7.31-7.24 (m, 1H), 7.12-7.08 (m, 1H), 6.93-6.90 (m, 1H), 4.68 (d, J=4.9 Hz, 1H), 4.37 (s, 1H), 4.27-4.21 (m, 1H), 3.06-3.01 (m, 1H), 2.90-2.82 (m, 1H), 1.92-1.89 (m, 1H), 1.61-1.54 (m, 1H), 1.33-1.31 (m, 1H).

Example 16: rac-(1R,2R,4S,5R,6S)-N-(3-fluoro-5-(trifluoromethyl)phenyl)-4-(2-fluoropyridin-4-yl)-6-hydroxy-8-oxatricyclo[3.2.1.0²,⁴]octane-2-carboxamide

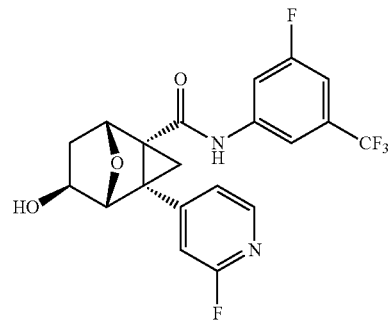 [SMILES: O=C(Nc1cc(F)cc(C(F)(F)F)c1)[C@]12C[C@@]1(c1ccnc(F)c1)[C@H]1O[C@@H]2C[C@@H]1O]

LC-MS: Rt=1.44 min; MS m/z [M+H]+ 427.2. $^1$H NMR (400 MHz, Acetonitrile-d$_3$) δ 8.58 (s, 1H), 8.12-8.07 (m, 1H), 7.75-7.64 (m, 2H), 7.22-7.17 (m, 1H), 7.11-7.07 (m, 1H), 6.94-6.90 (m, 1H), 4.70 (d, J=4.9 Hz, 1H), 4.38 (s, 1H), 4.28-4.22 (m, 1H), 3.07-3.02 (m, 1H), 2.87-2.80 (m, 1H), 1.93-1.91 (m, 1H), 1.61-1.55 (m, 1H), 1.35-1.32 (m, 1H).

Example 17: rac-(1R,2R,4S,5R,6S)—N-(2-fluoro-5-(trifluoromethyl)phenyl)-4-(2-fluoropyridin-4-yl)-6-hydroxy-8-oxatricyclo[3.2.1.02,4]octane-2-carboxamide

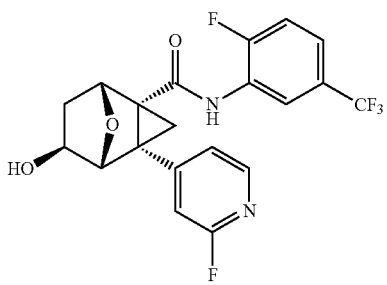 [SMILES: O=C(Nc1cc(C(F)(F)F)ccc1F)[C@]12C[C@@]1(c1ccnc(F)c1)[C@H]1O[C@@H]2C[C@@H]1O]

LC-MS: Rt=1.34 min; MS m/z [M+H]+ 427.2. $^1$H NMR (400 MHz, Acetonitrile-d$_3$) δ 8.21-8.16 (m, 1H), 8.15-8.08 (m, 2H), 7.54-7.49 (m, 1H), 7.38-7.31 (m, 1H), 7.17-7.12 (m, 1H), 6.96-6.92 (m, 1H), 4.71 (d, J=4.8 Hz, 1H), 4.38 (s, 1H), 4.30-4.24 (m, 1H), 3.06-3.02 (m, 1H), 2.88-2.79 (m, 1H), 1.96-1.92 (m, 1H), 1.63-1.56 (m, 1H), 1.36-1.32 (m, 1H).

Example 18: rac-(1R,2R,4S,5R,6S)—N-(4-chloro-3-(trifluoromethyl)phenyl)-4-(2-fluoropyridin-4-yl)-6-hydroxy-8-oxatricyclo[3.2.1.02,4]octane-2-carboxamide

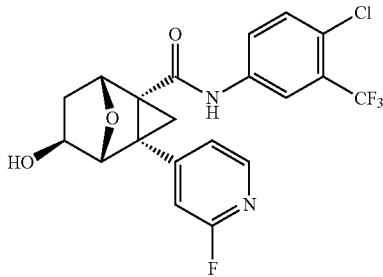 [SMILES: O=C(Nc1ccc(Cl)c(C(F)(F)F)c1)[C@]12C[C@@]1(c1ccnc(F)c1)[C@H]1O[C@@H]2C[C@@H]1O]

LC-MS: Rt=1.45 min; MS m/z [M+H]+ 443.1. $^1$H NMR (400 MHz, Acetonitrile-d$_3$) δ 8.51 (s, 1H), 8.11-8.07 (m, 1H), 8.06-8.03 (m, 1H), 7.78-7.73 (m, 1H), 7.55-7.50 (m, 1H), 7.11-7.06 (m, 1H), 6.93-6.89 (m, 1H), 4.69 (d, J=4.9 Hz, 1H), 4.38 (s, 1H), 4.28-4.21 (m, 1H), 3.06-3.02 (m, 1H), 2.88-2.81 (m, 1H), 1.92-1.90 (m, 1H), 1.61-1.55 (m, 1H), 1.34-1.31 (m, 1H).

Example 19: rac-(1R,2R,4S,5R,6S)—N-(3-chloro-5-(trifluoromethyl)phenyl)-4-(2-fluoropyridin-4-yl)-6-hydroxy-8-oxatricyclo[3.2.1.02,4]octane-2-carboxamide

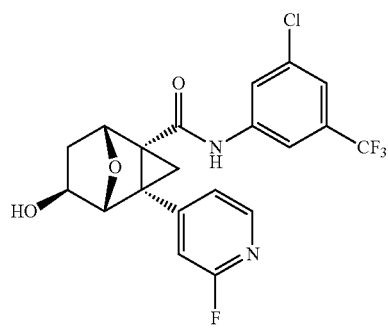

LC-MS: Rt=1.49 min; MS m/z [M+H]+ 443.1. $^1$H NMR (400 MHz, Acetonitrile-d$_3$) δ 8.54 (s, 1H), 8.11-8.08 (m, 1H), 7.89-7.86 (m, 1H), 7.84-7.81 (m, 1H), 7.47-7.44 (m, 1H), 7.11-7.08 (m, 1H), 6.93-6.90 (m, 1H), 4.69 (d, J=4.8 Hz, 1H), 4.38 (s, 1H), 4.27-4.22 (m, 1H), 3.07-3.03 (m, 1H), 2.87-2.80 (m, 1H), 1.93-1.91 (m, 1H), 1.61-1.55 (m, 1H), 1.35-1.32 (m, 1H).

Example 20: rac-(1R,2R,4S,5R,6S)-6-hydroxy-4-(2-methoxypyridin-4-yl)-N-(4-(trifluoromethyl)pyridin-2-yl)-8-oxatricyclo[3.2.1.02,4]octane-2-carboxamide

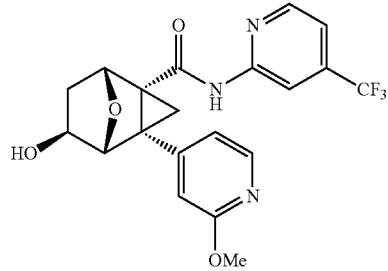 [SMILES: COc1cc([C@@]23C[C@]2(C(=O)Nc2cc(C(F)(F)F)ccn2)[C@H]2C[C@H](O)[C@@H]3O2)ccn1]

Method B: LC-MS: Rt=0.90 min; MS m/z [M+H]+ 422.3. $^1$H NMR (400 MHz, Acetonitrile-d$_3$) δ 8.61 (s, 1H), 8.52-8.46 (m, 1H), 8.37-8.32 (m, 1H), 8.06-8.00 (m, 1H), 7.39-7.33 (m, 1H), 6.80-6.73 (m, 1H), 6.69-6.65 (m, 1H), 4.73-4.68 (m, 1H), 4.33 (s, 1H), 4.32-4.24 (m, 1H). 3.88-3.83 (m, 3H), 3.31-2.99 (m, 1H), 2.87-2.78 (m, 1H), 1.91-1.87 (m, 1H), 1.63-1.53 (m, 1H), 1.36-1.31 (m, 1H).

Example 21: rac-(1R,2R,4S,5R,6S)—N-(6-chloro-4-(trifluoromethyl)pyridin-2-yl)-6-hydroxy-4-(2-methoxypyridin-4-yl)-8-oxatricyclo[3.2.1.02,4]octane-2-carboxamide

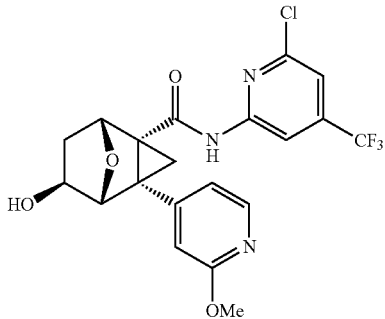

Method B: LC-MS: Rt=1.14 min; MS m/z [M+H]⁺ 456.1.
¹H NMR (400 MHz, Acetonitrile-d₃) δ 8.72 (s, 1H), 8.32-8.27 (m, 1H), 8.05-8.00 (m, 1H), 7.46-7.41 (m, 1H), 6.77-6.71 (m, 1H), 6.68-6.63 (m, 1H), 4.73-4.67 (m, 1H), 4.33 (s, 1H), 4.31-4.23 (m, 1H), 3.88-3.84 (m, 3H), 3.34-2.99 (m, 1H), 2.82-2.75 (m, 1H), 1.91-1.86 (m, 1H), 1.62-1.53 (m, 1H), 1.37-1.32 (m, 1H).

Example 22: rac-(1R,2R,4S,5R,6S)—N-(5-chloro-4-(trifluoromethyl)pyridin-2-yl)-6-hydroxy-4-(2-methoxypyridin-4-yl)-8-oxatricyclo[3.2.1.02,4]octane-2-carboxamide

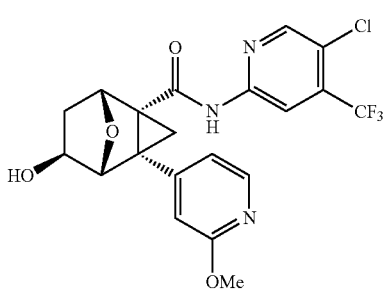 [SMILES: COc1cc([C@@]23C[C@]2(C(=O)Nc2cc(C(F)(F)F)c(Cl)cn2)[C@H]2C[C@H](O)[C@@H]3O2)ccn1]

Method B: LC-MS: Rt=1.05 min; MS m/z [M+H]⁺ 456.1.
¹H NMR (400 MHz, Acetonitrile-d₃) δ 8.70 (s, 1H), 8.50-8.45 (m, 2H), 8.05-7.99 (m, 1H), 6.77-6.71 (m, 1H), 6.68-6.63 (m, 1H), 4.70 (d, J=4.9 Hz, 1H), 4.33 (s, 1H), 4.30-4.24 (m, 1H), 3.86 (s, 3H), 3.07-2.96 (m, 1H), 2.85-2.76 (m, 1H), 1.90-1.87 (m, 1H), 1.62-1.54 (m, 1H), 1.38-1.31 (m, 1H).

Example 23: rac-(1R,2R,4S,5R,6S)—N-(6-cyclopropyl-4-(trifluoromethyl)pyridin-2-yl)-6-hydroxy-4-(2-methoxypyridin-4-yl)-8-oxatricyclo[3.2.1.02,4]octane-2-carboxamide

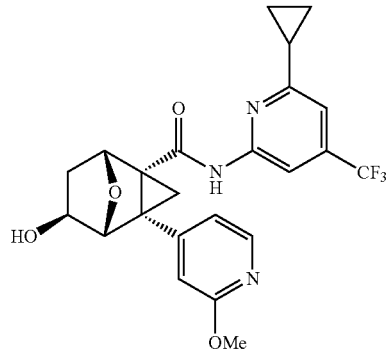 [SMILES: COc1cc([C@@]23C[C@]2(C(=O)Nc2cc(C(F)(F)F)cc(C4CC4)n2)[C@H]2C[C@H](O)[C@@H]3O2)ccn1]

Method B: LC-MS: Rt=1.15 min; MS m/z [M+H]⁺ 462.4.
¹H NMR (400 MHz, Acetonitrile-d₃) δ 8.39 (s, 1H), 8.06-8.00 (m, 2H), 7.26 (s, 1H), 6.79-6.73 (m, 1H), 6.65 (d, J=1.5 Hz, 1H), 4.67 (d, J=4.8 Hz, 1H), 4.32 (s, 1H), 4.30-4.23 (m, 1H), 3.86 (s, 3H), 3.31-2.97 (m, 1H), 2.80 (dd, J=12.9, 7.1 Hz, 1H), 2.12-2.02 (m, 1H), 1.87 (d, J=5.0 Hz, 1H), 1.62-1.52 (m, 1H), 1.30 (d, J=5.1 Hz, 1H), 1.04-0.90 (m, 4H).

Example 24: rac-(1R,2R,4S,5R,6S)-6-hydroxy-4-(2-methoxypyridin-4-yl)-N-(6-methyl-4-(trifluoromethyl)pyridin-2-yl)-8-oxatricyclo[3.2.1.02,4]octane-2-carboxamide

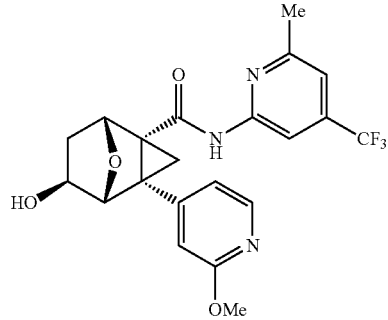 [SMILES: COc1cc([C@@]23C[C@]2(C(=O)Nc2cc(C(F)(F)F)cc(C)n2)[C@H]2C[C@H](O)[C@@H]3O2)ccn1]

Method B: LC-MS; Rt=1.00 min; MS m/z [M+H]⁺ 436.3.
¹H NMR (400 MHz, Acetonitrile-d₃) δ 8.51 (s, 1H), 8.14 (s, 1H), 8.03 (d, J=5.4 Hz, 1H), 7.24 (s, 1H), 6.76 (dd, J=5.4, 1.6 Hz, 1H), 6.68-6.64 (m, 1H), 4.69 (d, J=4.8 Hz, 1H), 4.33 (s, 1H), 4.31-4.23 (m, 1H), 3.85 (s, 3H), 3.31-2.96 (m, 1H), 2.82 (dd, J=12.8, 7.1 Hz, 1H), 2.48 (s, 3H), 1.88 (d, J=5.0 Hz, 1H), 1.62-1.52 (m, 1H), 1.36-1.29 (m, 1H).

Example 25: rac-(1R,2R,4S,5R,6S)—N-(6-ethoxy-4-(trifluoromethyl)pyridin-2-yl)-6-hydroxy-4-(2-methoxypyridin-4-yl)-8-oxatricyclo[3.2.1.0²,⁴]octane-2-carboxamide

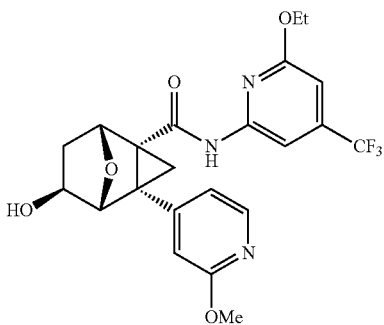 [SMILES: CCOc1cc(C(F)(F)F)cc(NC(=O)[C@]23C[C@@]2(c2ccnc(OC)c2)[C@H]2O[C@@H]3C[C@@H]2O)n1]

Method B; LC-MS: Rt=1.16 min; MS m/z [M+H]⁺ 466.3.
¹H NMR (400 MHz, Acetonitrile-d₃) δ 8.46 (s, 1H), 8.06-8.01 (m, 1H), 7.87-7.83 (m, 1H), 6.79-6.72 (m, 2H), 6.68-6.61 (m, 1H), 4.71-4.66 (m, 1H), 4.36-4.23 (m, 4H), 3.85 (s, 3H), 3.31-2.98 (m, 1H), 2.84-2.76 (m, 1H), 1.92-1.85 (m, 1H), 1.62-1.52 (m, 1H), 1.37-1.29 (m, 4H).

Example 26: rac-(1R,2R,4S,5R,6S)-6-hydroxy-4-(2-methoxypyridin-4-yl)-N-(3-(trifluoromethyl)phenyl)-8-oxatricyclo[3.2.1.0²,⁴]octane-2-carboxamide

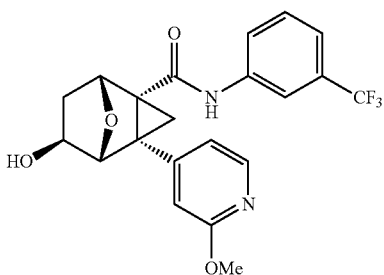 [SMILES: COc1cc([C@@]23C[C@]2(C(=O)Nc2cccc(C(F)(F)F)c2)[C@H]2C[C@H](O)[C@@H]3O2)ccn1]

Method B: LC-MS: Rt=1.04 min; MS m/z [M+H]⁺ 421.2.
¹H NMR (400 MHz, Acetonitrile-d₃) δ 8.33 (s, 1H), 8.06-8.00 (m, 1H), 7.94-7.89 (m, 1H), 7.75-7.67 (m, 1H), 7.55-7.46 (m, 1H), 7.46-7.37 (m, 1H), 6.79-6.73 (m, 1H), 6.67-6.62 (m, 1H), 4.68-4.64 (m, 1H), 4.34 (s, 1H), 4.29-4.21 (m, 1H), 3.85 (s, 3H), 3.31-2.97 (m, 1H), 2.95-2.85 (m, 1H), 1.88-1.82 (m, 1H), 1.60-1.51 (m, 1H), 1.33-1.27 (m, 1H).

Example 27: rac-(1R,2R,4S,5R,6S)-6-hydroxy-4-(2-methoxypyridin-4-yl)-N-(2-methyl-3-(trifluoromethyl)phenyl)-8-oxatricyclo[3.2.1.0²,⁴]octane-2-carboxamide

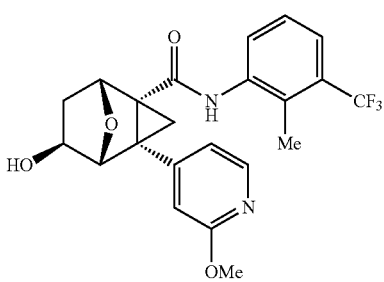 [SMILES: COc1cc([C@@]23C[C@]2(C(=O)Nc2cccc(C(F)(F)F)c2C)[C@H]2C[C@H](O)[C@@H]3O2)ccn1]

Method B: LC-MS; Rt=0.97 min; MS m/z [M+H]⁺ 435.3.
¹H NMR (400 MHz, Acetonitrile-d₃) δ 8.10-8.04 (m, 1H), 7.79 (s, 1H), 7.59-7.51 (m, 2H), 7.39-7.30 (m, 1H), 6.86-6.80 (m, 1H), 6.73-6.68 (m, 1H), 4.71-4.64 (m, 1H), 4.33-4.24 (m, 2H), 3.87 (s, 3H), 3.31-2.95 (m, 1H), 2.94-2.86 (m, 1H), 2.13 (s, 3H), 1.89-1.83 (m, 1H), 1.64-1.55 (m, 1H), 1.30-1.25 (m, 1H).

Example 28: rac-(1R,2R,4S,5R,6S)-6-hydroxy-4-(2-methoxypyridin-4-yl)-N-(4-methyl-3-(trifluoromethyl)phenyl)-8-oxatricyclo[3.2.1.0²,⁴]octane-2-carboxamide

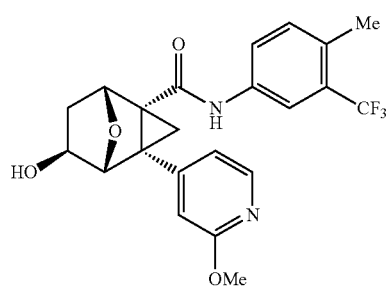 [SMILES: COc1cc([C@@]23C[C@]2(C(=O)Nc2ccc(C)c(C(F)(F)F)c2)[C@H]2C[C@H](O)[C@@H]3O2)ccn1]

Method B: LC-MS: Rt=1.06 min; MS m/z [M+H]⁺ 435.3.
¹H NMR (400 MHz, Acetonitrile-d₃) δ 8.24 (s, 1H), 8.03 (d, J=5.4 Hz, 1H), 7.87-7.82 (m, 1H), 7.64-7.57 (m, 1H), 7.31 (d, J=8.4 Hz, 1H), 6.79-6.72 (m, 1H), 6.66-6.61 (m, 1H), 4.64 (d, J=4.8 Hz, 1H), 4.33 (s, 1H), 4.28-4.20 (m, 1H), 3.85 (s, 3H), 3.31-2.95 (m, 1H), 2.90 (dd, J=12.8, 7.1 Hz, 1H), 2.46-2.39 (m, 3H), 1.84 (d, J=4.9 Hz, 1H), 1.59-1.50 (m, 1H), 1.28 (d, J=4.9 Hz, 1H).

Example 29: rac-(1R,2R,4S,5R,6S)-6-hydroxy-4-(2-methoxypyridin-4-yl)-N-(3-methyl-5-(trifluoromethyl)phenyl)-8-oxatricyclo[3.2.1.0²,⁴]octane-2-carboxamide

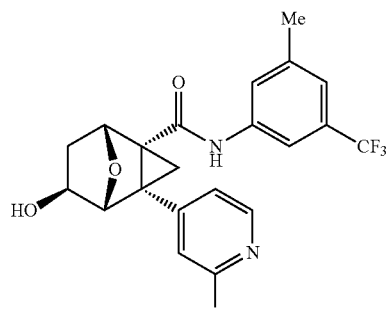

Method B: LC-MS: Rt=1.13 min; MS m/z [M+H]⁺ 435.2.
¹H NMR (400 MHz, Acetonitrile-d₃) δ 8.26 (s, 1H), 8.03 (d, J=5.4 Hz, 1H), 7.70 (s, 1H), 7.54 (s, 1H), 7.25 (s, 1H), 6.76 (dd, J=5.4, 1.5 Hz, 1H), 6.66-6.61 (m, 1H), 4.64 (d, J=4.8 Hz, 1H), 4.34 (s, 1H), 4.29-4.20 (m, 1H), 3.85 (s, 3H), 2.99 (d, J=5.7 Hz, 1H), 2.93-2.85 (m, 1H), 2.38 (s, 3H), 1.84 (d, J=4.9 Hz, 1H), 1.60-1.50 (m, 1H), 1.29 (d, J=5.0 Hz, 1H).

Example 30: rac-(1R,2R,4S,5R,6S)-6-hydroxy-4-(2-methoxypyridin-4-yl)-N-(2-methyl-5-(trifluoromethyl)phenyl)-8-oxatricyclo[3.2.1.02,4]octane-2-carboxamide

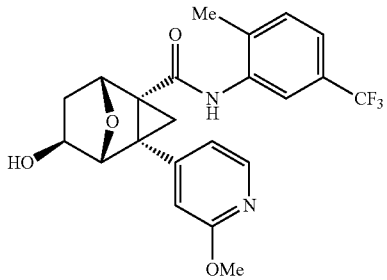 [SMILES: COc1cc([C@@]23C[C@]2(C(=O)Nc2cc(C(F)(F)F)ccc2C)[C@H]2C[C@H](O)[C@@H]3O2)ccn1]

Method B: LC-MS: Rt=0.98 min; MS m/z [M+H]⁺ 435.3. ¹H NMR (400 MHz, Acetonitrile-d₃) δ 8.06 (d, J=5.3 Hz, 1H), 7.78 (s, 1H), 7.69 (s, 1H), 7.45-7.36 (m, 2H), 6.87-6.81 (m, 1H), 6.72-6.65 (m, 1H), 4.68 (d, J=4.8 Hz, 1H), 4.34-4.25 (m, 2H), 3.86 (s, 3H), 3.32-2.95 (m, 1H), 2.91 (dd, J=12.8, 7.1 Hz, 1H), 2.19 (s, 3H), 1.87 (d, J=4.9 Hz, 1H), 1.64-1.54 (m, 1H), 1.28 (d, J=5.0 Hz, 1H).

Example 31: rac-(1R,2R,4S,5R,6S)—N-(2-fluoro-3-(trifluoromethyl)phenyl)-6-hydroxy-4-(2-methoxypyridin-4-yl)-8-oxatricyclo[3.2.1.02,4]octane-2-carboxamide

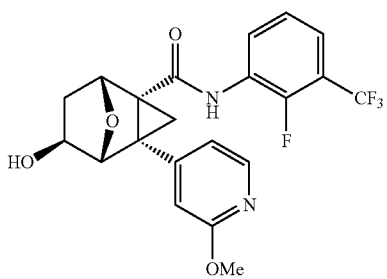 [SMILES: COc1cc([C@@]23C[C@]2(C(=O)Nc2cccc(C(F)(F)F)c2F)[C@H]2C[C@H](O)[C@@H]3O2)ccn1]

Method B: LC-MS: Rt=0.97 min; MS m/z [M+H]⁺ 439.3. ¹H NMR (400 MHz, Acetonitrile-d₃) δ 8.08-7.83 (m, 3H), 7.52-7.43 (m, 1H), 7.37-7.27 (m, 1H), 6.80 (dd, J=5.4, 1.5 Hz, 1H), 6.70-6.66 (m, 1H), 4.67 (d, J=4.9 Hz, 1H), 4.32 (s, 1H), 4.30-4.24 (m, 1H), 3.86 (s, 3H), 3.33-2.96 (m, 1H), 2.88-2.81 (m, 1H), 1.88 (d, J=5.0 Hz, 1H), 1.63-1.53 (m, 1H), 1.29 (d, J=5.0 Hz, 1H).

Example 32: rac-(1R,2R,4S,5R,6S)—N-(4-fluoro-3-(trifluoromethyl)phenyl)-6-hydroxy-4-(2-methoxypyridin-4-yl)-8-oxatricyclo[3.2.1.02,4]octane-2-carboxamide

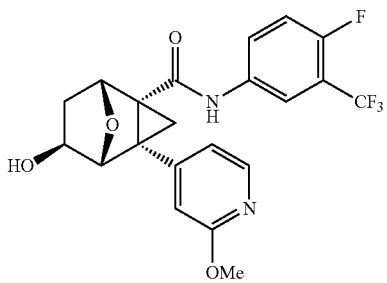 [SMILES: COc1cc([C@@]23C[C@]2(C(=O)Nc2ccc(F)c(C(F)(F)F)c2)[C@H]2C[C@H](O)[C@@H]3O2)ccn1]

Method B: LC-MS: Rt=1.00 min; MS m/z [M+H]⁺ 439.3. ¹H NMR (400 MHz, Acetonitrile-d₃) δ 8.31 (s, 1H), 8.06-8.01 (m, 1H), 7.90 (dd, J=6.5, 2.7 Hz, 1H), 7.76-7.69 (m, 1H), 7.31-7.22 (m, 1H), 6.75 (dd, J=5.4, 1.6 Hz, 1H), 6.67-6.62 (m, 1H), 4.64 (d, J=4.8 Hz, 1H), 4.33 (s, 1H), 4.29-4.20 (m, 1H), 3.85 (s, 3H), 3.31-2.96 (m, 1H), 2.92-2.84 (m, 1H), 1.84 (d, J=4.9 Hz, 1H), 1.60-1.51 (m, 1H), 1.28 (d, J=4.9 Hz, 1H).

Example 33: rac-(1R,2R,4S,5R,6S)—N-(2-fluoro-5-(trifluoromethyl)phenyl)-6-hydroxy-4-(2-methoxypyridin-4-yl)-8-oxatricyclo[3.2.1.02,4]octane-2-carboxamide

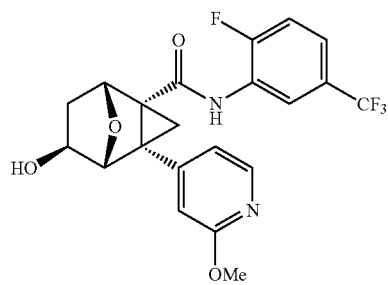 [SMILES: COc1cc([C@@]23C[C@]2(C(=O)Nc2cc(C(F)(F)F)ccc2F)[C@H]2C[C@H](O)[C@@H]3O2)ccn1]

Method B: LC-MS: Rt=1.01 min; MS m/z [M+H]⁺ 439.1. ¹H NMR (400 MHz, Acetonitrile-d₃) δ 8.22-8.14 (m, 1H), 8.08-8.02 (m, 1H), 7.95 (s, 1H), 7.54-7.46 (m, 1H), 7.38-7.28 (m, 1H), 6.80 (dd, J=5.4, 1.5 Hz, 1H), 6.70-6.66 (m, 1H), 4.67 (d, J=4.8 Hz, 1H), 4.33 (s, 1H), 4.31-4.24 (m, 1H), 3.86 (s, 3H), 3.00 (s, 1H), 2.85 (dd, J=12.9, 7.1 Hz, 1H), 1.89 (d, J=5.0 Hz, 1H), 1.63-1.53 (m, 1H), 1.29 (d, J=5.0 Hz, 1H).

Example 34: rac-(1R,2R,4S,5R,6S)-6-hydroxy-N-(4-methoxy-3-(trifluoromethyl)phenyl)-4-(2-methoxypyridin-4-yl)-8-oxatricyclo[3.2.1.02,4]octane-2-carboxamide

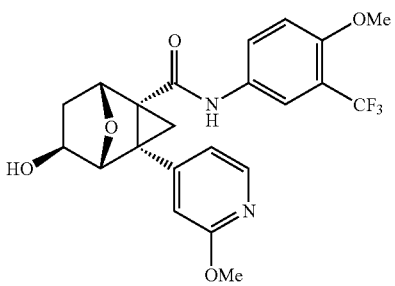 [SMILES: COc1cc([C@@]23C[C@]2(C(=O)Nc2ccc(OC)c(C(F)(F)F)c2)[C@H]2C[C@H](O)[C@@H]3O2)ccn1]

Method B: LC-MS: Rt=1.00 min; MS m/z [M+H]⁺ 451.1. ¹H NMR (400 MHz, Acetonitrile-d₃) δ 8.17-8.12 (m, 1H), 8.05-8.01 (m, 1H), 7.78-7.73 (m, 1H), 7.70-7.63 (m, 1H), 7.15-7.08 (m, 1H), 6.79-6.73 (m, 1H), 6.66-6.61 (m, 1H), 4.65-4.60 (m, 1H), 4.33 (s, 1H), 4.28-4.19 (m, 1H), 3.90-3.83 (m, 6H), 3.30-2.96 (m, 1H), 2.96-2.87 (m, 1H), 1.85-1.79 (m, 1H), 1.59-1.50 (m, 1H), 1.29-1.23 (m, 1H).

Example 35: rac-(1R,2R,4S,5R,6S)-6-hydroxy-N-(3-methoxy-5-(trifluoromethyl)phenyl)-4-(2-methoxypyridin-4-yl)-8-oxatricyclo[3.2.1.02,4]octane-2-carboxamide

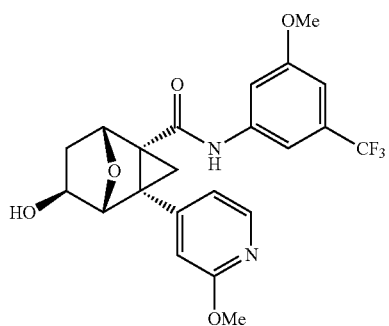 [SMILES: COc1cc(NC(=O)[C@]23C[C@@]2(c2ccnc(OC)c2)[C@H]2O[C@@H]3C[C@@H]2O)cc(C(F)(F)F)c1]

Method B: LC-MS: Rt=1.09 min; MS m/z [M+H]+ 451.1. 1H NMR (400 MHz, Acetonitrile-d3) δ 8.28 (s, 1H), 8.05-8.01 (m, 1H), 7.49-7.45 (m, 1H), 7.37-7.31 (m, 1H), 7.00-6.93 (m, 1H), 6.75 (dd, J=5.4, 1.6 Hz, 1H), 6.66-6.61 (m, 1H), 4.67-4.62 (m, 1H), 4.34 (s, 1H), 4.29-4.20 (m, 1H), 3.87-3.79 (m, 6H), 2.89 (dd, J=12.8, 7.1 Hz, 1H), 2.10 (d, J=2.6 Hz, 1H), 1.85 (d, J=5.0 Hz, 1H), 1.60-1.50 (m, 1H), 1.29 (d, J=5.0 Hz, 1H).

Example 36: rac-(1R,2R,4S,5R,6S)-6-hydroxy-N-(2-methoxy-5-(trifluoromethyl)phenyl)-4-(2-methoxypyridin-4-yl)-8-oxatricyclo[3.2.1.02,4]octane-2-carboxamide

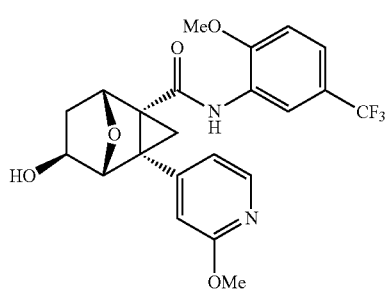 [SMILES: COc1cc([C@@]23C[C@]2(C(=O)Nc2cc(C(F)(F)F)ccc2OC)[C@H]2C[C@H](O)[C@@H]3O2)ccn1]

Method B: LC-MS: Rt=1.09 min; MS m/z [M+H]+ 451.2. 1H NMR (400 MHz, Acetonitrile-d3) δ 8.47-8.41 (m, 1H), 8.10-8.04 (m, 1H), 7.70-7.66 (m, 1H), 7.43-7.35 (m, 1H), 7.10-7.02 (m, 1H), 6.87-6.79 (m, 1H), 6.72-6.66 (m, 1H), 4.70-4.64 (m, 1H), 4.35-4.27 (m, 2H), 3.87 (s, 3H), 3.77 (s, 3H), 3.31-2.94 (m, 1H), 2.86-2.77 (m, 1H), 1.90 (d, J=5.1 Hz, 1H), 1.65-1.56 (m, 1H), 1.27-1.21 (m, 1H).

Example 37: rac-(1R,2R,4S,5R,6S)—N-(3,5-bis(trifluoromethyl)phenyl)-6-hydroxy-4-(2-methoxypyridin-4-yl)-8-oxatricyclo[3.2.1.02,4]octane-2-carboxamide

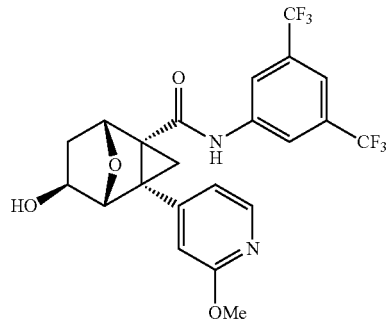 [SMILES: COc1cc([C@@]23C[C@]2(C(=O)Nc2cc(C(F)(F)F)cc(C(F)(F)F)c2)[C@H]2C[C@H](O)[C@@H]3O2)ccn1]

Method B: LC-MS: Rt=1.24 min; MS m/z [M+H]+ 489.1. 1H NMR (400 MHz, Acetonitrile-d3) δ 8.51 (s, 1H), 8.12 (s, 2H), 8.03 (d, J=5.4 Hz, 1H), 7.71 (s, 1H), 6.76 (dd, J=5.4, 1.5 Hz, 1H), 6.68-6.63 (m, 1H), 4.67 (d, J=4.8 Hz, 1H), 4.34 (s, 1H), 4.26 (d, J=7.0 Hz, 1H), 3.85 (s, 3H), 2.88 (dd, J=12.9, 7.1 Hz, 1H), 2.10 (d, J=2.2 Hz, 1H), 1.88 (d, J=5.0 Hz, 1H), 1.62-1.53 (m, 1H), 1.31 (d, J=4.9 Hz, 1H).

Example 38: rac-(1R,2R,4S,5R,6S)—N-(4-cyano-3-(trifluoromethyl)phenyl)-6-hydroxy-4-(2-methoxypyridin-4-yl)-8-oxatricyclo[3.2.1.02,4]octane-2-carboxamide

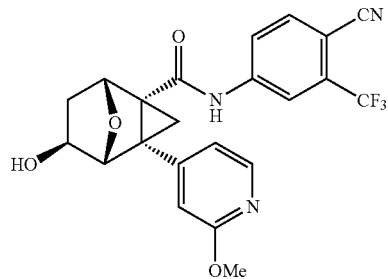 [SMILES: COc1cc([C@@]23C[C@]2(C(=O)Nc2ccc(C#N)c(C(F)(F)F)c2)[C@H]2C[C@H](O)[C@@H]3O2)ccn1]

Method B: LC-MS: Rt=1.02 min; MS m/z [M+H]+ 446.1. 1H NMR (400 MHz, Acetonitrile-d3) δ 8.61 (s, 1H), 8.15-8.10 (m, 1H), 8.03 (d, J=5.4 Hz, 1H), 7.95-7.84 (m, 2H), 6.77-6.70 (m, 1H), 6.66-6.61 (m, 1H), 4.70-4.64 (m, 1H), 4.34 (s, 1H), 4.29-4.21 (m, 1H), 3.85 (s, 3H), 3.31-2.93 (m, 1H), 2.89-2.79 (m, 1H), 1.91-1.85 (m, 1H), 1.62-1.52 (m, 1H), 1.32 (d, J=5.0 Hz, 1H).

Example 39: rac-(1R,2R,4S,5R,6S)—N-(2-cyano-5-(trifluoromethyl)phenyl)-6-hydroxy-4-(2-methoxypyridin-4-yl)-8-oxatricyclo[3.2.1.0²,⁴]octane-2-carboxamide

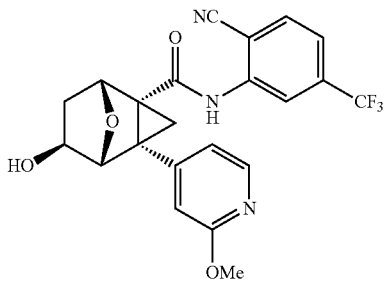 [SMILES: COc1cc([C@@]23C[C@]2(C(=O)Nc2cc(C(F)(F)F)ccc2C#N)[C@H]2C[C@H](O)[C@@H]3O2)ccn1]

Method B: LC-MS: Rt=0.95 min; MS m/z [M+H]⁺ 446.1. ¹H NMR (400 MHz, Acetonitrile-d₃) δ 8.17 (s, 1H), 8.07-8.03 (m, 2H), 7.92-7.87 (m, 1H), 7.64-7.59 (m, 1H), 6.85-6.81 (m, 1H), 6.73-6.69 (m, 1H), 4.73-4.68 (m, 1H), 4.34-4.26 (m, 2H), 3.86 (s, 3H), 3.01-2.97 (m, 1H), 2.93-2.84 (m, 1H), 2.11-2.07 (m, 1H), 1.67-1.59 (m, 1H), 1.33-1.28 (m, 1H).

Examples 39a and 39b (Corresponding to Peak 1 and Peak 2)

(1R,2R,4S,5R,6S)—N-(2-cyano-5-(trifluoromethyl)phenyl)-6-hydroxy-4-(2-methoxypyridin-4-yl)-8-oxatricyclo[3.2.1.0²,⁴]octane-2-carboxamide or (1S,2S,4R,5S,6R)—N-(2-cyano-5-(trifluoromethyl)phenyl)-6-hydroxy-4-(2-methoxypyridin-4-yl)-8-oxatricyclo[3.2.1.0²,⁴]octane-2-carboxamide

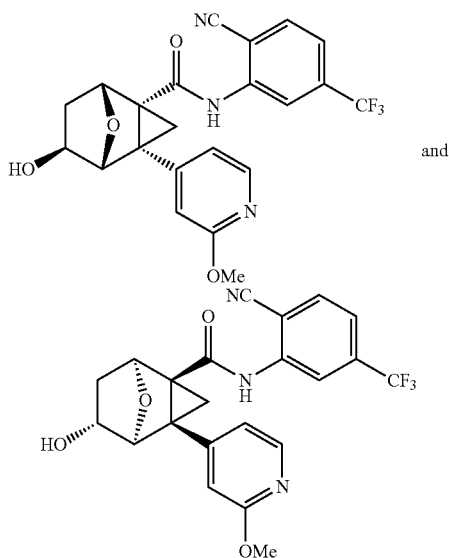

Chiral separation of rac-(1R,2R,4S,5R,6S)—N-(2-cyano-5-(trifluoromethyl)phenyl)-6-hydroxy-4-(2-methoxypyridin-4-yl)-8-oxatricyclo[3.2.1.0²,⁴]octane-2-carboxamide by SFC using the following conditions afforded the compounds listed hereafter.
Column: 21×250 mm Chiralpak IG @ 35° C.
Mobile Phase: 85% CO₂/15% MeOH
Detection: UV @ 214 nm
Flow: 80 mL/min Peak 1: SFC Retention Time=1.20 min. Method B: LC-MS: Rt=1.11 min; MS m/z [M+H]⁺ 464.1. ¹H NMR (400 MHz, Acetonitrile-d₃) δ 8.17 (s, 1H), 8.07-8.02 (m, 2H), 7.92-7.86 (m, 1H), 7.65-7.59 (m, 1H), 6.86-6.81 (m, 1H), 6.74-6.69 (m, 1H), 4.74-4.68 (m, 1H), 4.33-4.26 (m, 2H), 3.86 (s, 3H), 3.01-2.96 (m, 1H), 2.93-2.85 (m, 1H), 2.11-2.07 (m, 1H), 1.67-1.59 (m, 1H), 1.32-1.29 (m, 1H).

Peak 2: SFC Retention Time=1.89 min. Method B: LC-MS: Rt=1.11 min; MS m/z [M+H]⁺ 464.1. ¹H NMR (400 MHz, Acetonitrile-d₃) δ 8.17 (s, 1H), 8.07-8.02 (m, 2H), 7.92-7.87 (m, 1H), 7.65-7.58 (m, 1H), 6.86-6.81 (m, 1H), 6.74-6.70 (m, 1H), 4.73-4.69 (m, 1H), 4.33-4.26 (m, 2H), 3.86 (s, 3H), 3.01-2.96 (m, 1H), 2.92-2.84 (m, 1H), 2.11-2.07 (m, 1H), 1.67-1.60 (m, 1H), 1.33-1.29 (m, 1H).

Example 40: rac-(1R,2R,4S,5R,6S)—N-(3-chloro-4-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide

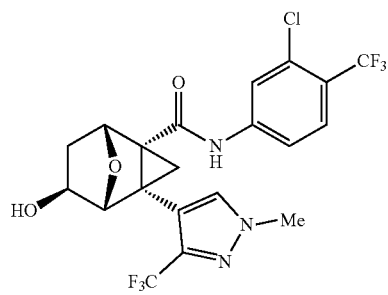 [SMILES: Cn1cc([C@@]23C[C@]2(C(=O)Nc2ccc(C(F)(F)F)c(Cl)c2)[C@H]2C[C@H](O)[C@@H]3O2)c(C(F)(F)F)n1]

LC-MS: Rt=1.59 min; MS m/z [M+H]⁺ 496.2. ¹H NMR (400 MHz, Acetonitrile-d₃) δ 8.14 (s, 1H), 7.94-7.90 (m, 1H), 7.71-7.66 (m, 1H), 7.56-7.51 (m, 1H), 7.48 (s, 1H), 4.65 (d, J=4.8 Hz, 1H), 4.22-4.16 (m, 1H), 4.09 (s, 1H), 3.83 (s, 3H), 2.89-2.79 (m, 2H), 1.80 (d, J=5.0 Hz, 1H), 1.61-1.53 (m, 1H), 1.17 (d, J=5.0 Hz, 1H).

Example 41: rac-(1R,2R,4S,5R,6S)—N-(3-fluoro-4-(trifluoromethyl)phenyl-6-hydroxy-4-(1-methyl-3-(trifluoromethyl)-1H-pyrazol-4-yl)-8-oxatricyclo[3.2.1.0²,⁴]octane-2-carboxamide

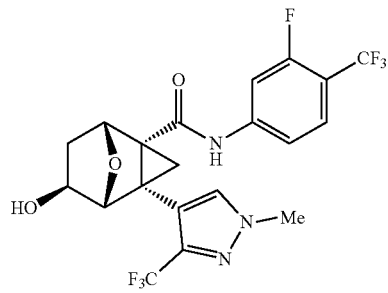

LC-MS; Rt=1.55 min; MS m/z [M+H]⁺ 480.2. ¹H NMR (400 MHz, Acetonitrile-d₃) δ 8.20 (s, 1H), 7.77-7.66 (m, 1H), 7.63-7.55 (m, 1H), 7.48-7.45 (m, 1H), 7.38-7.32 (m, 1H), 4.66 (d, J=4.8 Hz, 1H), 4.22-4.16 (m, 1H), 4.10 (s, 1H), 3.82 (s, 3H), 2.90-2.76 (m, 2H), 1.80 (d, J=5.0 Hz, 1H), 1.61-1.53 (m, 1H), 1.17 (d, J=5.0 Hz, 1H).

Example 42: rac-(1R,2R,4S,5R,6S)-6-hydroxy-4-(1-methyl-3-(trifluoromethyl)-1H-pyrazol-4-yl)-N-(4-(trifluoromethyl)phenyl)-8-oxatricyclo[3.2.1.02,4]octane-2-carboxamide

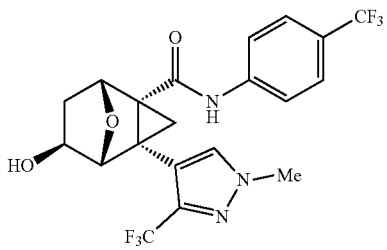

LC-MS: Rt=1.51 min; MS m/z [M+H]$^+$ 462.2. $^1$H NMR (400 MHz, Acetonitrile-d$_3$) δ 8.07 (s, 1H), 7.69 (d, J=8.7 Hz, 2H), 7.61 (d, J=8.6 Hz, 2H), 7.51-7.46 (m, 1H), 4.65 (d, J=4.9 Hz, 1H), 4.22-4.16 (m, 1H), 4.09 (s, 1H), 3.82 (s, 3H), 2.96-2.71 (m, 2H), 1.79 (d, J=4.9 Hz, 1H), 1.60-1.54 (m, 1H), 1.16 (d, J=5.0 Hz, 1H).

Example 43: rac-(1R,2R,4S,5R,6S)-6-hydroxy-4-(1-methyl-3-(trifluoromethyl)-1H-pyrazol-4-yl)-N-(4-(trifluoromethyl)pyridin-2-yl)-8-oxatricyclo[3.2.1.02,4]octane-2-carboxamide

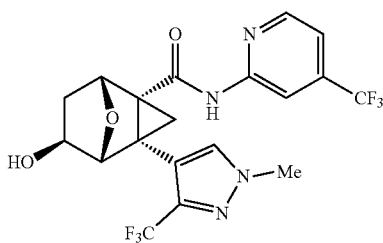 [SMILES: Cn1cc([C@@]23C[C@]2(C(=O)Nc2cc(C(F)(F)F)ccn2)[C@H]2C[C@H](O)[C@@H]3O2)c(C(F)(F)F)n1]

LC-MS: Rt=1.47 min; MS m/z [M+H]$^+$ 463.2. $^1$H NMR (400 MHz, Acetonitrile-d$_3$) δ 8.50-8.46 (m, 1H), 8.38-8.35 (m, 1H), 8.31 (s, 1H), 7.52-7.50 (m, 1H), 7.37-7.33 (m, 1H), 4.69 (d, J=4.8 Hz, 1H), 4.23-4.19 (m, 1H), 4.10 (s, 1H), 3.82 (s, 3H), 2.98-2.74 (m, 2H), 1.84 (d, J=5.1 Hz, 1H), 1.62-1.55 (m, 1H), 1.22 (d, J=5.1 Hz, 1H).

Example 44: rac-(1R,2R,4S,5R,6S)—N-(6-chloro-4-(trifluoromethyl)pyridin-2-yl)-6-hydroxy-4-(1-methyl-3-(trifluoromethyl)-1H-pyrazol-4-yl)-8-oxatricyclo[3.2.1.02,4]octane-2-carboxamide

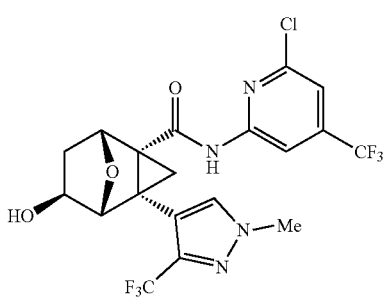

LC-MS: Rt=1.58 min; MS m/z [M+H]$^+$ 497.1. $^1$H NMR (400 MHz, Acetonitrile-d$_3$) δ 8.38 (s, 1H), 8.34-8.29 (m, 1H), 7.50-7.46 (m, 1H), 7.46-7.42 (m, 1H), 4.68 (d, J=4.8 Hz, 1H), 4.22-4.17 (m, 1H), 4.10 (s, 1H), 3.83 (s, 3H), 2.78-2.71 (m, 1H), 2.61-2.42 (m, 1H), 1.84 (d, J=5.1 Hz, 1H), 1.62-1.55 (m, 1H), 1.23 (d, J=5.1 Hz, 1H).

Example 45: rac-(1R,2R,4S,5R,6S)—N-(5-chloro-4-(trifluoromethyl)pyridin-2-yl)-6-hydroxy-4-(1-methyl-3-(trifluoromethyl)-1H-pyrazol-4-yl)-8-oxatricyclo[3.2.1.02,4]octane-2-carboxamide

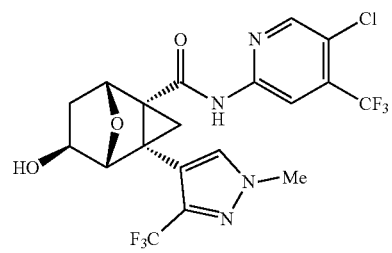

LC-MS: Rt=1.56 min; MS m/z [M+H]$^+$ 497.1. $^1$H NMR (400 MHz, Acetonitrile-d$_3$) δ 8.49 (s, 1H), 8.46 (s, 1H), 8.39 (s, 1H), 7.49-7.46 (m, 1H), 4.69 (d, J=4.8 Hz, 1H), 4.23-4.18 (m, 1H), 4.10 (s, 1H), 3.82 (s, 3H), 3.05-2.81 (m, 1H), 2.81-2.73 (m, 1H), 1.84 (d, J=5.1 Hz, 1H), 1.62-1.56 (m, 1H), 1.22 (d, J=5.1 Hz, 1H).

Example 46: rac-(1R,2R,4S,5R,6S)—N-(6-cyclopropyl-4-(trifluoromethyl)pyridin-2-yl)-6-hydroxy-4-(1-methyl-3-(trifluoromethyl)-1H-pyrazol-4-yl)-8-oxatricyclo[3.2.1.02,4]octane-2-carboxamide

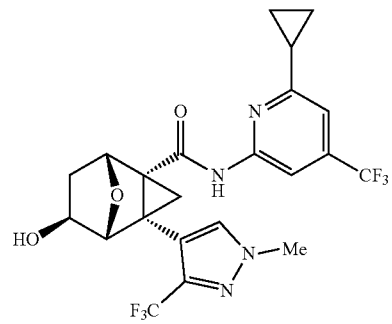 [SMILES: Cn1cc([C@@]23C[C@]2(C(=O)Nc2cc(C(F)(F)F)cc(C4CC4)n2)[C@H]2C[C@H](O)[C@@H]3O2)c(C(F)(F)F)n1]

LC-MS: Rt=1.64 min; MS m/z [M+H]$^+$ 503.2. $^1$H NMR (400 MHz, Acetonitrile-d$_3$) δ 8.16 (s, 1H), 8.08-8.05 (m, 1H), 7.50-7.48 (m, 1H), 7.26-7.24 (m, 1H), 4.66 (d, J=4.8 Hz, 1H), 4.22-4.17 (m, 1H), 4.09 (s, 1H), 3.82 (s, 3H), 3.08-2.79 (m, 1H), 2.79-2.72 (m, 1H), 2.12-2.03 (m, 1H), 1.82 (d, J=5.0 Hz, 1H), 1.61-1.54 (m, 1H), 1.18 (d, J=5.1 Hz, 1H), 1.02-0.89 (m, 4H).

Example 47: rac-(1R,2R,4S,5R,6S)-6-hydroxy-4-(1-methyl-3-(trifluoromethyl)-1H-pyrazol-4-yl)-N-(6-methyl-4-(trifluoromethyl)pyridin-2-yl)-8-oxatricyclo[3.2.1.0²,⁴]octane-2-carboxamide

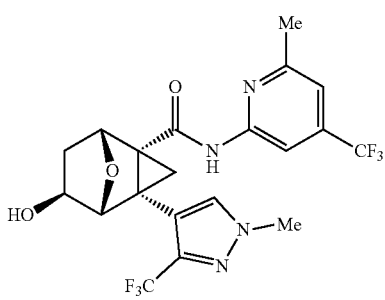

LC-MS: Rt=1.53 min; MS m/z [M+H]⁺ 477.2. ¹H NMR (400 MHz, Acetonitrile-d₃) δ 8.17 (s, 1H), 8.16-8.14 (m, 1H), 7.52-7.50 (m, 1H), 7.24-7.22 (m, 1H), 4.68 (d, J=4.8 Hz, 1H), 4.23-4.18 (m, 1H), 4.10 (s, 1H), 3.82 (s, 3H), 3.10-2.83 (m, 1H), 2.80-2.73 (m, 1H), 2.47 (s, 3H), 1.83 (d, J=5.0 Hz, 1H), 1.61-1.55 (m, 1H), 1.19 (d, J=5.1 Hz, 1H).

Example 48: rac-(1R,2R,4S,5R,6S)—N-(6-ethoxy-4-(trifluoromethyl)pyridin-2-yl)-6-hydroxy-4-(1-methyl-3-(trifluoromethyl)-1H-pyrazol-4-yl)-8-oxatricyclo[3.2.1.0²,⁴]octane-2-carboxamide

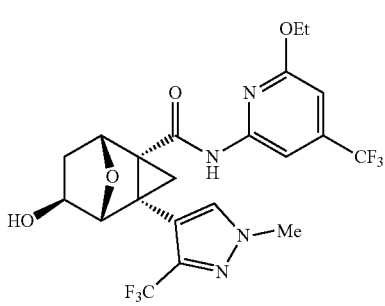

LC-MS: Rt=1.65 min; MS m/z [M+H]⁺ 507.2. ¹H NMR (400 MHz, Acetonitrile-d₃) δ 8.23 (s, 1H), 7.91-7.87 (m, 1H), 7.53-7.49 (m, 1H), 6.75-6.71 (m, 1H), 4.68 (d, J=4.8 Hz, 1H), 4.30 (q, J=7.0 Hz, 2H), 4.23-4.18 (m, 1H), 4.10 (s, 1H), 3.82 (s, 3H), 3.09-2.66 (m, 2H), 1.82 (d, J=5.1 Hz, 1H), 1.61-1.55 (m, 1H), 1.33 (t, J=7.1 Hz, 3H), 1.19 (d, J=5.4 Hz, 1H).

Example 49: rac-(1R,2R,4S,5R,6S)-6-hydroxy-4-(1-methyl-3-(trifluoromethyl)-1H-pyrazol-4-yl)-N-(3-(trifluoromethyl)phenyl)-8-oxatricyclo[3.2.1.0²,⁴]octane-2-carboxamide

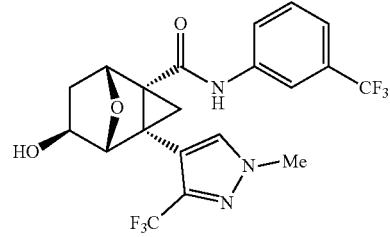 [SMILES: Cn1cc([C@@]23C[C@]2(C(=O)Nc2cccc(C(F)(F)F)c2)[C@H]2C[C@H](O)[C@@H]3O2)c(C(F)(F)F)n1]

LC-MS: Rt=1.50 min; MS m/z [M+H]⁺ 462.2. ¹H NMR (400 MHz, Acetonitrile-d₃) δ 8.05 (s, 1H), 7.93-7.90 (m, 1H), 7.70-7.65 (m, 1H), 7.52-7.46 (m, 2H), 7.43-7.38 (m, 1H), 4.64 (d, J=4.8 Hz, 1H), 4.22-4.16 (m, 1H), 4.09 (s, 1H), 3.82 (s, 3H), 3.22-2.90 (m, 1H), 2.89-2.81 (m, 1H), 1.78 (d, J=5.0 Hz, 1H), 1.60-1.54 (m, 1H), 1.16 (d, J=4.9 Hz, 1H).

Example 50: rac-(1R,2R,4S,5R,6S)-6-hydroxy-4-(1-methyl-3-(trifluoromethyl)-1H-pyrazol-4-yl)-N-(2-methyl-3-(trifluoromethyl)phenyl)-8-oxatricyclo[3.2.1.0²,⁴]octane-2-carboxamide

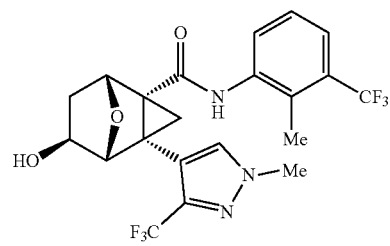 [SMILES: Cc1c(NC(=O)[C@]23C[C@@]2(c2cn(C)nc2C(F)(F)F)[C@H]2O[C@@H]3C[C@@H]2O)cccc1C(F)(F)F]

LC-MS: Rt=1.49 min; MS m/z [M+H]⁺ 476.2. ¹H NMR (400 MHz, Acetonitrile-d₃) δ 7.63 (s, 1H), 7.59-7.54 (m, 1H), 7.54-7.49 (m, 2H), 7.37-7.31 (m, 1H), 4.65 (d, J=4.8 Hz, 1H), 4.25-4.20 (m, 1H), 4.10 (s, 1H), 3.84 (s, 3H), 3.24-2.93 (m, 1H), 2.92-2.84 (m, 1H), 2.19 (s, 3H), 1.81 (d, J=4.9 Hz, 1H), 1.62-1.56 (m, 1H), 1.15 (d, J=4.9 Hz, 1H).

Example 51: rac-d R,2R,4S,5R,6S)-6-hydroxy-4-(1-methyl-3-(trifluoromethyl)-1H-pyrazol-4-yl)-N-(4-methyl-3-(trifluoromethyl)phenyl)-8-oxatricyclo[3.2.1.0²,⁴]octane-2-carboxamide

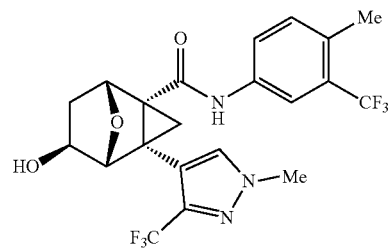

LC-MS: Rt=1.56 min; MS m/z [M+H]⁺ 476.2. ¹H NMR (400 MHz, Acetonitrile-d₃) δ 7.94 (s, 1H), 7.84-7.81 (m, 1H), 7.59-7.55 (m, 1H), 7.49-7.47 (m, 1H), 7.32-7.27 (m, 1H), 4.63 (d, J=4.8 Hz, 1H), 4.20-4.16 (m, 1H), 4.09 (s, 1H), 3.82 (s, 3H), 3.17-2.88 (m, 1H), 2.88-2.81 (m, 1H), 2.42 (s, 3H), 1.77 (d, J=4.9 Hz, 1H), 1.59-1.53 (m, 1H), 1.14 (d, J=4.9 Hz, 1H).

Example 52: rac-(1R,2R,4S,5R,6S)-6-hydroxy-4-(1-methyl-3-(trifluoromethyl)-1H-pyrazol-4-yl)-N-(3-methyl-5-(trifluoromethyl)phenyl)-8-oxatricyclo[3.2.1.02,4]octane-2-carboxamide

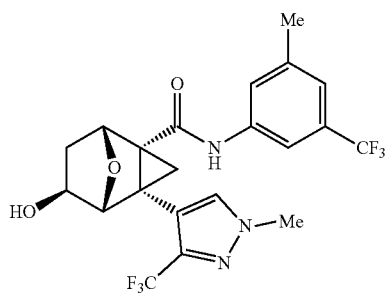

LC-MS: Rt=1.57 min; MS m/z [M+H]⁺ 476.2. ¹H NMR (400 MHz, Acetonitrile-d₃) δ 7.97 (s, 1H), 7.72-7.68 (m, 1H), 7.52-7.47 (m, 2H), 7.26-7.22 (m, 1H), 4.64 (d, J=4.8 Hz, 1H), 4.21-4.17 (m, 1H), 4.09 (s, 1H), 3.83 (s, 3H), 3.26-2.91 (m, 1H), 2.89-2.81 (m, 1H), 2.37 (s, 3H), 1.78 (d, J=4.9 Hz, 1H), 1.59-1.54 (m, 1H), 1.14 (d, J=4.9 Hz, 1H).

Example 53: rac-(1R,2R,4S,5R,6S)-6-hydroxy-4-(1-methyl-3-(trifluoromethyl)-1H-pyrazol-4-yl)-N-(2-methyl-5-(trifluoromethyl)phenyl)-8-oxatricyclo[3.2.1.02,4]octane-2-carboxamide

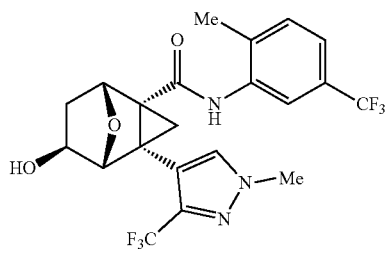 [SMILES: Cc1ccc(C(F)(F)F)cc1NC(=O)[C@]12C[C@@]1(c1cn(C)nc1C(F)(F)F)[C@H]1O[C@@H]2C[C@@H]1O]

LC-MS: Rt=1.52 min; MS m/z [M+H]⁺ 476.2. ¹H NMR (400 MHz, Acetonitrile-d₃) δ 7.79-7.77 (m, 1H), 7.55-7.53 (m, 1H), 7.49 (s, 1H), 7.43-7.36 (m, 2H), 4.66 (d, J=4.8 Hz, 1H), 4.26-4.20 (m, 1H), 4.10 (s, 1H), 3.83 (s, 3H), 3.59-3.11 (m, 1H), 2.90-2.83 (m, 1H), 2.13 (s, 3H), 1.83 (d, J=5.0 Hz, 1H), 1.62-1.56 (m, 1H), 1.16 (d, J=5.0 Hz, 1H).

Example 54: rac-(1R,2R,4S,5R,6S)—N-(2-fluoro-3-(trifluoromethyl)phenyl)-6-hydroxy-4-(1-methyl-3-(trifluoromethyl)-1H-pyrazol-4-yl)-8-oxatricyclo[3.2.1.02,4]octane-2-carboxamide

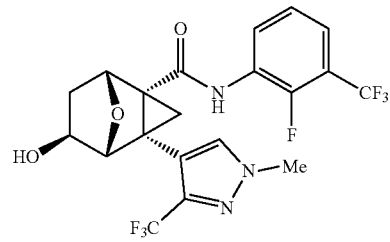 [SMILES: Cn1cc([C@@]23C[C@]2(C(=O)Nc2cccc(C(F)(F)F)c2F)[C@H]2C[C@H](O)[C@@H]3O2)c(C(F)(F)F)n1]

LC-MS: Rt=1.49 min; MS m/z [M+H]⁺ 480.2. ¹H NMR (400 MHz, Acetonitrile-d₃) δ 8.02-7.95 (m, 1H), 7.54 (s, 1H), 7.52-7.50 (m, 1H), 7.50-7.44 (m, 1H), 7.33-7.28 (m, 1H), 4.64 (d, J=4.9 Hz, 1H), 4.23-4.18 (m, 1H), 4.11 (s, 1H), 3.84 (s, 3H), 3.06-2.65 (m, 2H), 1.85 (d, J=5.1 Hz, 1H), 1.62-1.55 (m, 1H), 1.19 (d, J=5.1 Hz, 1H).

Example 55: rac-(1R,2R,4S,5R,6S)—N-(4-fluoro-3-(trifluoromethyl)phenyl)-6-hydroxy-4-n-methyl-3-(trifluoromethyl)-1H-pyrazol-4-yl)-8-oxatricyclo[3.2.1.02,4]octane-2-carboxamide

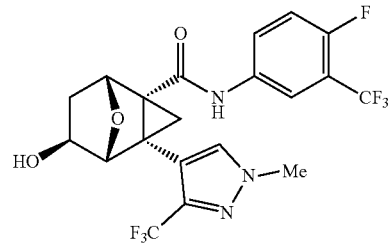 [SMILES: Cn1cc([C@@]23C[C@]2(C(=O)Nc2ccc(F)c(C(F)(F)F)c2)[C@H]2C[C@H](O)[C@@H]3O2)c(C(F)(F)F)n1]

LC-MS: Rt=1.52 min; MS m/z [M+H]⁺ 480.2. ¹H NMR (400 MHz, Acetonitrile-d₃) δ 8.02 (s, 1H), 7.92-7.88 (m, 1H), 7.73-7.67 (m, 1H), 7.49-7.45 (m, 1H), 7.29-7.22 (m, 1H), 4.63 (d, J=4.8 Hz, 1H), 4.21-4.16 (m, 1H), 4.09 (s, 1H), 3.82 (s, 3H), 3.02-2.69 (m, 2H), 1.78 (d, J=4.9 Hz, 1H), 1.60-1.54 (m, 1H), 1.15 (d, J=4.9 Hz, 1H).

Example 56: rac-(1R,2R,4S,5R,6S)—N-(3-fluoro-5-(trifluoromethyl)phenyl)-6-hydroxy-4-(1-methyl-3-(trifluoromethyl)-1H-pyrazol-4-yl)-8-oxatricyclo[3.2.1.02,4]octane-2-carboxamide

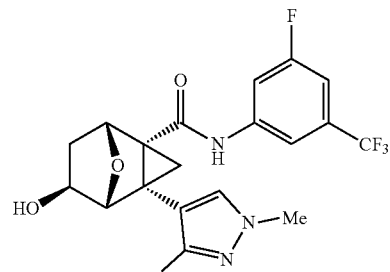

LC-MS: Rt=1.57 min; MS m/z [M+H]+ 480.2. ¹H NMR (400 MHz, Acetonitrile-d₃) δ 8.17 (s, 1H), 7.71-7.66 (m, 1H), 7.66-7.63 (m, 1H), 7.49-7.46 (m, 1H), 7.20-7.15 (m, 1H), 4.65 (d, J=4.8 Hz, 1H), 4.21-4.16 (m, 1H), 4.10 (s, 1H), 3.82 (s, 3H), 3.05-2.69 (m, 2H), 1.80 (d, J=5.0 Hz, 1H), 1.60-1.54 (m, 1H), 1.16 (d, J=4.9 Hz, 1H).

Example 57: rac-/1R,2R,4S,5R,6S)—N-(2-fluoro-5-(trifluoromethyl)phenyl)-6-hydroxy-4-(1-methyl-3-(trifluoromethyl)-1H-pyrazol-4-yl)-8-oxatricyclo[3.2.1.02,4]octane-2-carboxamide

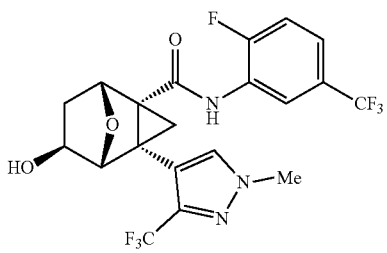 [SMILES: Cn1cc([C@@]23C[C@]2(C(=O)Nc2cc(C(F)(F)F)ccc2F)[C@H]2C[C@H](O)[C@@H]3O2)c(C(F)(F)F)n1]

LC-MS: Rt=1.51 min; MS m/z [M+H]+ 480.2. ¹H NMR (400 MHz, Acetonitrile-d₃) δ 8.18-8.15 (m, 1H), 7.57 (s, 1H), 7.54-7.52 (m, 1H), 7.52-7.47 (m, 1H), 7.35-7.28 (m, 1H), 4.65 (d, J=4.9 Hz, 1H), 4.24-4.18 (m, 1H), 4.11 (s, 1H), 3.86-3.80 (m, 3H), 3.15-2.81 (m, 1H), 2.81-2.73 (m, 1H), 1.85 (d, J=5.2 Hz, 1H), 1.61-1.55 (m, 1H), 1.18 (d, J=5.1 Hz, 1H).

Example 58: rac-(1R,2R,4S,5R,6S)—N-(4-chloro-3-(trifluoromethyl)phenyl)-6-hydroxy-4-(1-methyl-3-(trifluoromethyl)-1H-pyrazol-4-yl)-8-oxatricyclo[3.2.1.02,4]octane-2-carboxamide

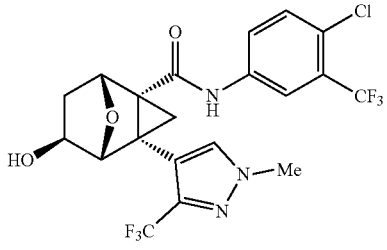

LC-MS; Rt=1.59 min; MS m/z [M+H]+ 496.2. ¹H NMR (400 MHz, Acetonitrile-d₃) δ 8.09 (s, 1H), 8.02-8.00 (m, 1H), 7.73-7.69 (m, 1H), 7.53-7.49 (m, 1H), 7.47-7.45 (m, 1H), 4.64 (d, J=4.8 Hz, 1H), 4.21-4.16 (m, 1H), 4.09 (s, 1H), 3.82 (s, 3H), 2.92-2.65 (m, 2H), 1.79 (d, J=5.0 Hz, 1H), 1.60-1.54 (m, 1H), 1.16 (d, J=5.0 Hz, 1H).

Example 59: rac-(1R,2R,4S,5R,6S)—N-(3-chloro-5-(trifluoromethyl)phenyl)-6-hydroxy-4-n-methyl-3-(trifluoromethyl)-1H-pyrazol-4-yl)-8-oxatricyclo[3.2.1.02,4]octane-2-carboxamide

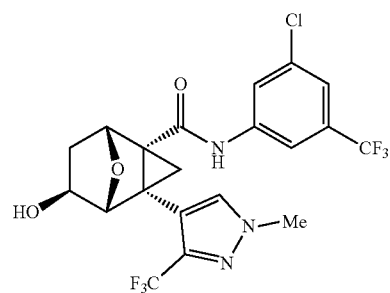 [SMILES: Cn1cc([C@@]23C[C@]2(C(=O)Nc2cc(Cl)cc(C(F)(F)F)c2)[C@H]2C[C@H](O)[C@@H]3O2)c(C(F)(F)F)n1]

LC-MS: Rt=1.62 min; MS m/z [M+H]+ 496.2. ¹H NMR (400 MHz, Acetonitrile-d₃) δ 8.12 (s, 1H), 7.88-7.85 (m, 1H), 7.79-7.77 (m, 1H), 7.49-7.47 (m, 1H), 7.45-7.41 (m, 1H), 4.64 (d, J=4.8 Hz, 1H), 4.21-4.16 (m, 1H), 4.10 (s, 1H), 3.82 (s, 3H), 2.86-2.79 (m, 1H), 2.65-2.24 (m, 1H), 1.80 (d, J=5.0 Hz, 1H), 1.61-1.54 (m, 1H), 1.16 (d, J=4.9 Hz, 1H).

Example 60: rac-(1R,2R,4S,5R,6S)-6-hydroxy-N-(4-methoxy-3-(trifluoromethyl)phenyl)-4-(1-methyl-3-(trifluoromethyl)-1H-pyrazol-4-yl)-8-oxatricyclo[3.2.1.02,4]octane-2-carboxamide

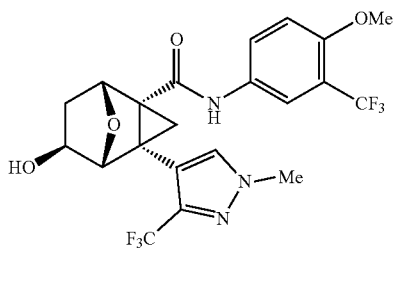 [SMILES: COc1ccc(NC(=O)[C@]23C[C@@]2(c2cn(C)nc2C(F)(F)F)[C@H]2O[C@@H]3C[C@@H]2O)cc1C(F)(F)F]

LC-MS: Rt=1.48 min; MS m/z [M+H]+ 492.2. ¹H NMR (400 MHz, Acetonitrile-d₃) δ 7.86 (s, 1H), 7.75-7.73 (m, 1H), 7.64-7.60 (m, 1H), 7.49-7.47 (m, 1H), 7.12-7.07 (m, 1H), 4.62 (d, J=4.8 Hz, 1H), 4.20-4.15 (m, 1H), 4.09 (s, 1H), 3.87 (s, 3H), 3.82 (s, 3H), 2.91-2.61 (m, 2H), 1.76 (d, J=4.9 Hz, 1H), 1.59-1.53 (m, 1H), 1.12 (d, J=4.9 Hz, 1H).

Example 61: rac-(1R,2R,4S,5R,6S)-6-hydroxy-N-(3-methoxy-5-(trifluoromethyl)phenyl)-4-(1-methyl-3-(trifluoromethyl)-1H-pyrazol-4-yl)-8-oxatricyclo[3.2.1.0²,⁴]octane-2-carboxamide

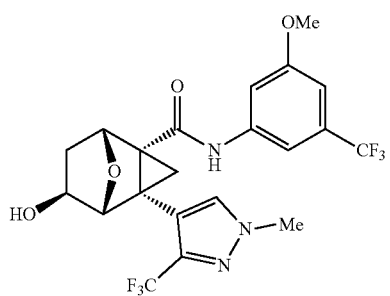

LC-MS: Rt=1.54 min; MS m/z [M+H]$^+$ 492.2. $^1$H NMR (400 MHz, Acetonitrile-d$_3$) δ 8.00 (s, 1H), 7.50-7.46 (m, 2H), 7.35-7.32 (m, 1H), 6.96-6.92 (m, 1H), 4.64 (d, J=4.8 Hz, 1H), 4.21-4.15 (m, 1H), 4.09 (s, 1H), 3.82 (s, 3H), 3.81 (s, 3H), 2.92-2.45 (m, 2H), 1.78 (d, J=4.9 Hz, 1H), 1.60-1.54 (m, 1H), 1.14 (d, J=4.9 Hz, 1H).

Example 62: rac-(1R,2R,4S,5R,6S)-6-hydroxy-N-(2-methoxy-5-(trifluoromethyl)phenyl)-4-(1-methyl-3-(trifluoromethyl)-1H-pyrazol-4-yl)-8-oxatricyclo[3.2.1.0²,⁴]octane-2-carboxamide

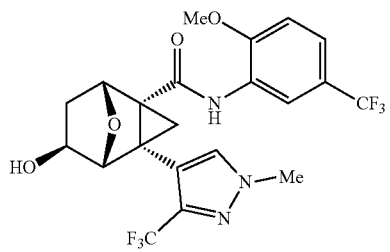 [SMILES: COc1ccc(C(F)(F)F)cc1NC(=O)[C@]12C[C@@]1(c1cn(C)nc1C(F)(F)F)[C@H]1O[C@@H]2C[C@@H]1O]

LC-MS: Rt=1.57 min; MS m/z [M+H]$^+$ 492.2. $^1$H NMR (400 MHz, Acetonitrile-d$_3$) δ 8.50-8.46 (m, 1H), 7.53-7.48 (m, 1H), 7.43 (s, 1H), 7.40-7.35 (m, 1H), 7.08-7.03 (m, 1H), 4.65 (d, J=4.9 Hz, 1H), 4.26-4.22 (m, 1H), 4.10 (s, 1H), 3.82 (s, 3H), 3.77 (s, 3H), 3.36-2.88 (m, 1H), 2.75-2.65 (m, 1H), 1.89 (d, J=5.3 Hz, 1H), 1.64-1.57 (m, 1H), 1.13 (d, J=5.4 Hz, 1H).

Example 63: rac-(1R,2R,4S,5R,6S)—N-(3,5-bis(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide

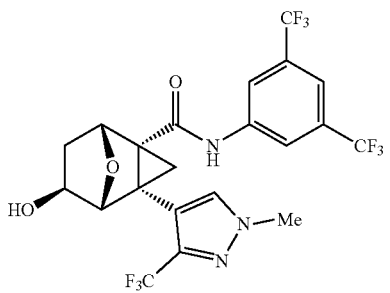

LC-MS: Rt=1.66 min; MS m/z [M+H]$^+$ 530.2. $^1$H NMR (400 MHz, Acetonitrile-d$_3$) δ 8.24 (s, 1H), 8.14-8.10 (m, 2H), 7.72-7.68 (m, 1H), 7.49-7.47 (m, 1H), 4.66 (d, J=4.8 Hz, 1H), 4.22-4.17 (m, 1H), 4.11 (s, 1H), 3.82 (s, 3H), 3.05-2.57 (m, 2H), 1.82 (d, J=5.0 Hz, 1H), 1.62-1.55 (m, 1H), 1.19 (d, J=5.0 Hz, 1H).

Example 64: rac-(1R,2R,4S,5R,6S)-6-hydroxy-4-(1-methyl-3-(trifluoromethyl)-1H-pyrazol-4-yl)-N-(4-morpholino-3-(trifluoromethyl)phenyl)-8-oxatricyclo[3.2.1.0²,⁴]octane-2-carboxamide

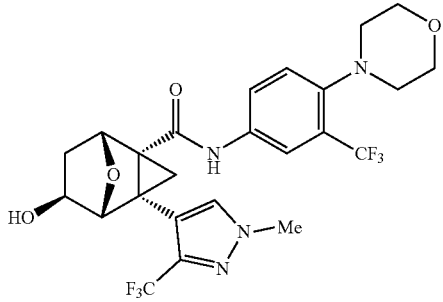 [SMILES: Cn1cc([C@@]23C[C@]2(C(=O)Nc2ccc(N4CCOCC4)c(C(F)(F)F)c2)[C@H]2C[C@H](O)[C@@H]3O2)c(C(F)(F)F)n1]

LC-MS: Rt=1.52 min; MS m/z [M+H]$^+$ 547.2. $^1$H NMR (400 MHz, Acetonitrile-d$_3$) δ 7.96 (s, 1H), 7.83-7.80 (m, 1H), 7.70-7.66 (m, 1H), 7.50-7.47 (m, 1H), 7.46-7.41 (m, 1H), 4.63 (d, J=4.8 Hz, 1H), 4.21-4.15 (m, 1H), 4.09 (s, 1H), 3.82 (s, 3H), 3.75-3.70 (m, 4H), 2.88-2.81 (m, 5H), 2.79-2.39 (m, 1H), 1.77 (d, J=4.8 Hz, 1H), 1.59-1.53 (m, 1H), 1.14 (d, J=4.8 Hz, 1H).

Example 65: rac-(1R,2R,4S,5R,6S)—N-(4-ethoxy-3-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide

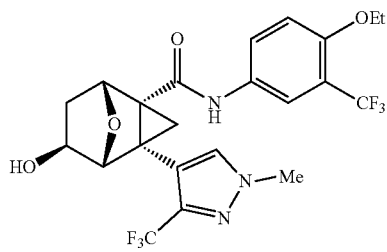 [SMILES: CCOc1ccc(NC(=O)[C@]23C[C@@]2(c2cn(C)nc2C(F)(F)F)[C@H]2O[C@@H]3C[C@@H]2O)cc1C(F)(F)F]

LC-MS: Rt=1.56 min; MS m/z [M+H]⁺ 506.2. ¹H NMR (400 MHz, Acetonitrile-d₃) δ 7.86 (s, 1H), 7.74-7.72 (m, 1H), 7.62-7.58 (m, 1H), 7.49-7.46 (m, 1H), 7.10-7.05 (m, 1H), 4.62 (d, J=4.8 Hz, 1H), 4.19-4.16 (m, 1H), 4.12 (q, J=7.0 Hz, 2H), 4.09 (s, 1H), 3.82 (s, 3H), 3.01-2.49 (m, 2H), 1.76 (d, J=4.9 Hz, 1H), 1.59-1.53 (m, 1H), 1.36 (t, J=7.0 Hz, 3H), 1.12 (d, J=4.9 Hz, 1H).

Example 66: rac-(1R,2R,4S,5R,6S)-6-hydroxy-N-(3-(trifluoromethyl)phenyl)-4-(2-(trifluoromethyl)pyridin-4-yl)-8-oxatricyclo[3.2.1.0²,⁴]octane-2-carboxamide

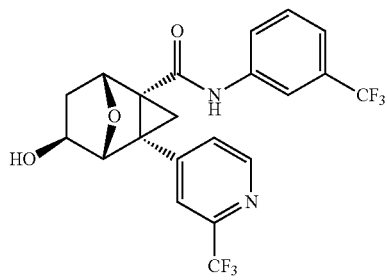 [SMILES: O=C(Nc1cccc(C(F)(F)F)c1)[C@]12C[C@@]1(c1ccnc(C(F)(F)F)c1)[C@H]1O[C@@H]2C[C@@H]1O]

Method C: LC-MS: Rt=0.61 min; MS m/z [M+H]⁺ 459.1. ¹H NMR (400 MHz, DMSO-d₆) δ 10.15 (s, 1H), 8.69-8.64 (m, 1H), 8.01-7.96 (m, 1H), 7.83-7.76 (m, 1H), 7.66-7.61 (m, 1H), 7.59-7.50 (m, 2H), 7.44-7.37 (m, 1H), 5.01 (s, 1H), 4.76-4.72 (m, 1H), 4.48 (s, 1H), 4.12-4.04 (m, 1H), 2.79-2.71 (m, 1H), 1.87-1.83 (m, 1H), 1.53-1.45 (m, 2H).

Example 67: rac-(1R,2R,4S,5R,6S)-6-hydroxy-N,4-bis(3-(trifluoromethyl)phenyl)-8-oxatricyclo[3.2.1.0²,⁴]octane-2-carboxamide

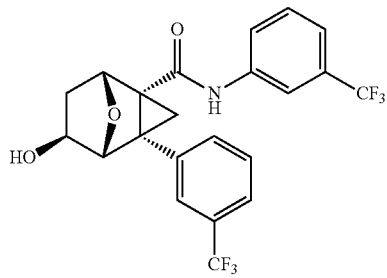 [SMILES: O=C(Nc1cccc(C(F)(F)F)c1)[C@]12C[C@@]1(c1cccc(C(F)(F)F)c1)[C@H]1O[C@@H]2C[C@@H]1O]

Method C: LC-MS: Rt=0.66 min; MS m/z [M+H]⁺ 458.1. ¹H NMR (400 MHz, DMSO-d₆) δ 9.71 (s, 1H), 7.93-7.90 (m, 1H), 7.78-7.74 (m, 1H), 7.64-7.59 (m, 1H), 7.57-7.54 (m, 2H), 7.54-7.50 (m, 2H), 7.43-7.39 (m, 1H), 4.89 (d, J=4.8 Hz, 1H), 4.73 (d, J=4.7 Hz, 1H), 4.32 (s, 1H), 4.14-4.08 (m, 1H), 2.88-2.81 (m, 1H), 1.79 (d, J=4.7 Hz, 1H), 1.56-1.50 (m, 1H), 1.39 (d, J=4.7 Hz, 1H).

Example 68: rac-(1R,2R,4S,5R,6S)—N-(4-cyano-3-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide

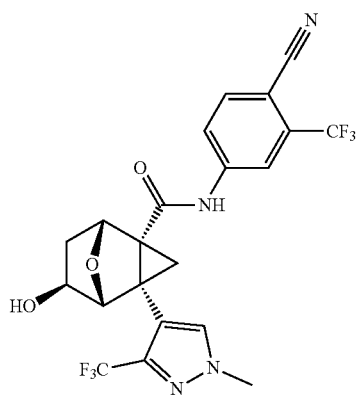 [SMILES: Cn1cc([C@@]23C[C@]2(C(=O)Nc2ccc(C#N)c(C(F)(F)F)c2)[C@H]2C[C@H](O)[C@@H]3O2)c(C(F)(F)F)n1]

Method B: LC-MS: Rt=1.13 min; MS m/z [M+H]⁺ 487.0. ¹H NMR (400 MHz, Chloroform-d) δ 7.99-7.94 (m, 1H), 7.81-7.68 (m, 2H), 7.48-7.37 (m, 2H), 4.70-4.64 (m, 1H), 4.33-4.26 (m, 2H), 3.90 (s, 3H), 3.14-3.05 (m, 1H), 2.05-1.99 (m, 1H), 1.73-1.63 (m, 2H), 1.06-0.99 (m, 1H).

Example 69: rac-(1R,2R,4S,5R,6S)—N-(2-cyano-5-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide

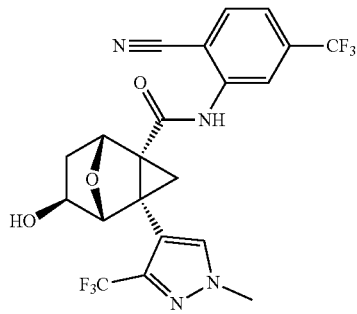 [SMILES: Cn1cc([C@@]23C[C@]2(C(=O)Nc2cc(C(F)(F)F)ccc2C#N)[C@H]2C[C@H](O)[C@@H]3O2)c(C(F)(F)F)n1]

Method B: LC-MS: Rt=1.01 min; MS m/z [M+H]⁺ 487.1. ¹H NMR (400 MHz, Methanol-d₄) δ 7.98-7.92 (m, 1H), 7.90-7.85 (m, 1H), 7.72-7.65 (m, 2H), 4.80-4.75 (m, 1H), 4.32-4.25 (m, 1H), 4.18 (s, 1H), 3.87 (s, 3H), 2.98-2.89 (m, 1H), 2.01 (s, 1H), 1.95-1.89 (m, 1H), 1.76-1.67 (m, 1H).

Example 70: rac-(1R,2R,4S,5R,6S)—N-(4-chloro-3-(trifluoromethyl)phenyl)-6-hydroxy-4-(2-methoxypyridin-4-yl)-8-oxatricyclo[3.2.1.02,4]octane-2-carboxamide

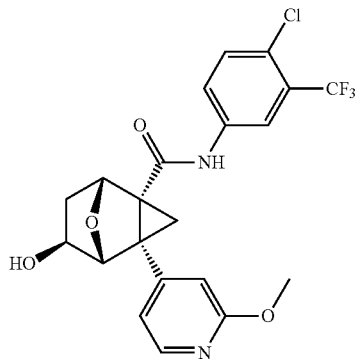 [SMILES: COc1cc([C@@]23C[C@]2(C(=O)Nc2ccc(Cl)c(C(F)(F)F)c2)[C@H]2C[C@H](O)[C@@H]3O2)ccn1]

Method B: LC-MS: Rt=1.16 min; MS m/z [M+H]+ 455.1. 1H NMR (400 MHz, Methanol-d4) δ 7.95-7.87 (m, 2H), 7.73-7.64 (m, 1H), 7.47-7.40 (m, 1H), 6.70-6.64 (m, 1H), 6.59-6.55 (m, 1H), 4.62-4.56 (m, 1H), 4.30 (s, 1H), 4.25-4.18 (m, 1H), 3.77 (s, 3H), 2.90-2.81 (m, 1H), 1.88-1.82 (m, 1H), 1.59-1.49 (m, 1H), 1.30-1.20 (m, 1H).

Example 71: rac-(1R,2R,4S,5R,6S)—N-(3-chloro-5-(trifluoromethyl)phenyl)-6-hydroxy-4-(2-methoxypyridin-4-yl)-8-oxatricyclo[3.2.1.02,4]octane-2-carboxamide

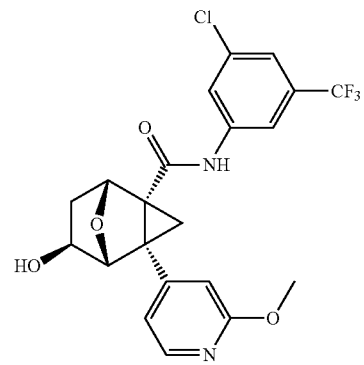 [SMILES: COc1cc([C@@]23C[C@]2(C(=O)Nc2cc(Cl)cc(C(F)(F)F)c2)[C@H]2C[C@H](O)[C@@H]3O2)ccn1]

Method B: LC-MS: Rt=1.19 min; MS m/z [M+H]+ 455.1. 1H NMR (400 MHz, Methanol-d4) δ 7.96-7.90 (m, 1H), 7.86-7.80 (m, 1H), 7.76-7.71 (m, 1H), 7.34-7.29 (m, 1H), 6.71-6.64 (m, 1H), 6.60-6.55 (m, 1H), 4.63-4.57 (m, 1H), 4.30 (s, 1H), 4.25-4.19 (m, 1H), 3.80-3.74 (m, 3H), 2.90-2.81 (m, 1H), 1.88-1.82 (m, 1H), 1.59-1.50 (m, 1H), 1.33-1.22 (m, 1H).

Example 72: rac-(1R,2R,4S,5R,6S)—N-(3-cyano-5-(trifluoromethyl)phenyl)-6-hydroxy-4-(2-methoxypyridin-4-yl)-8-oxatricyclo[3.2.1.02,4]octane-2-carboxamide

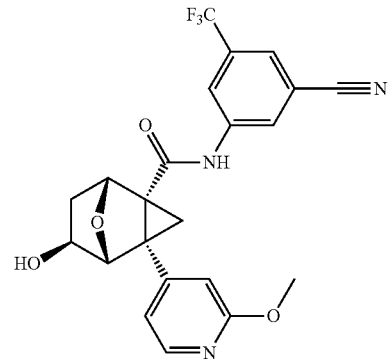 [SMILES: COc1cc([C@@]23C[C@]2(C(=O)Nc2cc(C#N)cc(C(F)(F)F)c2)[C@H]2C[C@H](O)[C@@H]3O2)ccn1]

Method B: LC-MS: Rt=1.04 min; MS m/z [M+H]+ 446.1. 1H NMR (400 MHz, Methanol-d4) δ 8.15-8.05 (m, 2H), 7.96-7.90 (m, 1H), 7.70 (s, 1H), 6.72-6.66 (m, 1H), 6.61-6.56 (m, 1H), 4.64-4.58 (m, 1H), 4.30 (s, 1H), 4.26-4.19 (m, 1H), 3.80-3.75 (m, 3H), 2.90-2.82 (m, 1H), 1.89-1.84 (m, 1H), 1.60-1.51 (m, 1H), 1.34-1.26 (m, 1H).

Example 73: rac-(1R,2R,4S,5R,6S)—N-(3-fluoro-5-(trifluoromethyl)phenyl)-6-hydroxy-4-(2-methoxypyridin-4-yl)-8-oxatricyclo[3.2.1.02,4]octane-2-carboxamide

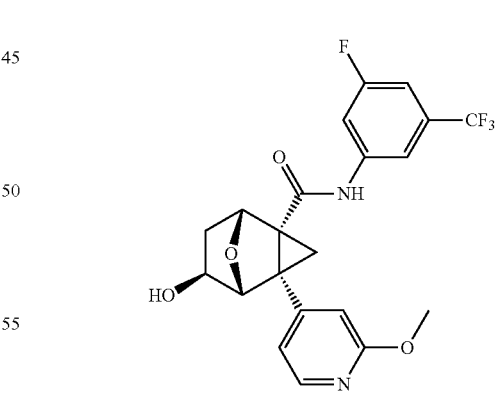

Method B: LC-MS: Rt=112 min; MS m/z [M+H]+ 439.1. 1H NMR (400 MHz, Methanol-d4) δ 8.05-7.99 (m, 1H), 7.78-7.65 (m, 2H), 7.21-7.13 (m, 1H), 6.80-6.74 (m, 1H), 6.69-6.61 (m, 1H), 4.74-4.67 (m, 1H), 4.41 (s, 1H), 4.35-4.28 (m, 1H), 3.87 (s, 3H), 3.00-2.91 (m, 1H), 1.98-1.91 (m, 1H), 1.69-1.60 (m, 1H), 1.40-1.34 (m, 1H).

Example 74: rac-(1R,2R,4S,5R,6S)—N-(3-chloro-4-(trifluoromethyl)phenyl)-6-hydroxy-4-(2-methoxy-pyridin-4-yl)-8-oxatricyclo[3.2.1.0²,⁴]octane-2-carboxamide

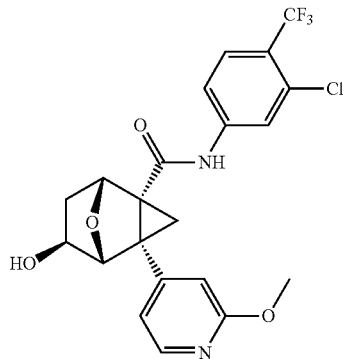 [SMILES: COc1cc([C@@]23C[C@]2(C(=O)Nc2ccc(C(F)(F)F)c(Cl)c2)[C@H]2C[C@H](O)[C@@H]3O2)ccn1]

Method B: LC-MS: Rt=1.18 min; MS m/z [M+H]⁺ 455.1. ¹H NMR (400 MHz, Chloroform-d) δ 8.18-8.13 (m, 1H), 7.61-7.54 (m, 2H), 7.23-7.16 (m, 1H), 6.79 (s, 1H), 6.75-6.66 (m, 2H), 4.77-4.72 (m, 1H), 4.45-4.36 (m, 2H), 3.96-3.91 (m, 3H), 2.99-2.90 (m, 1H), 2.10-2.04 (m, 1H), 1.82-1.71 (m, 2H), 1.14-1.09 (m, 1H).

Example 75: rac-(1R,2R,4S,5R,6S)—N-(3-fluoro-4-(trifluoromethyl)phenyl)-6-hydroxy-4-(2-methoxy-pyridin-4-yl)-8-oxatricyclo[3.2.1.0²,⁴]octane-2-carboxamide

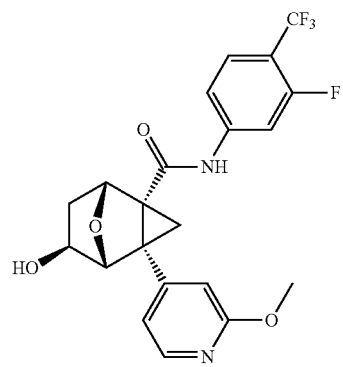 [SMILES: COc1cc([C@@]23C[C@]2(C(=O)Nc2ccc(C(F)(F)F)c(F)c2)[C@H]2C[C@H](O)[C@@H]3O2)ccn1]

Method B: LC-MS: Rt=1.12 min; MS m/z [M+H]⁺ 439.1. ¹H NMR (400 MHz, Methanol-d₄) δ 8.05-7.99 (m, 1H), 7.76-7.68 (m, 1H), 7.64-7.56 (m, 1H), 7.49-7.42 (m, 1H), 6.79-6.73 (m, 1H), 6.69-6.64 (m, 1H), 4.72-4.68 (m, 1H), 4.41 (s, 1H), 4.35-4.28 (m, 1H), 3.87 (s, 3H), 2.99-2.90 (m, 1H), 1.99-1.93 (m, 1H), 1.68-1.59 (m, 1H), 1.39-1.33 (m, 1H).

Example 76: rac-(1R,2R,4S,5R,6S)-6-hydroxy-4-(2-methoxyl)pyridin-4-yl)-N-(4-(trifluoromethyl)phenyl)-8-oxatricyclo[3.2.1.0²,⁴]octane-2-carboxamide

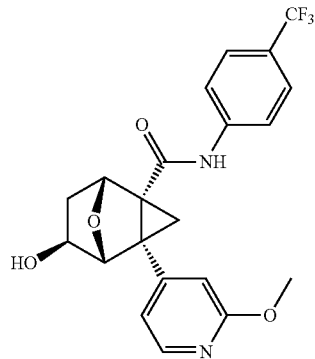 [SMILES: COc1cc([C@@]23C[C@]2(C(=O)Nc2ccc(C(F)(F)F)cc2)[C@H]2C[C@H](O)[C@@H]3O2)ccn1]

Method B: LC-MS: Rt=0.98 min; MS m/z [M+H]⁺ 421.2. ¹H NMR (400 MHz, Methanol-d₄) δ 8.04-7.98 (m, 1H), 7.77-7.70 (m, 2H), 7.64-7.57 (m, 2H), 6.80-6.73 (m, 1H), 6.70-6.66 (m, 1H), 4.73-4.68 (m, 1H), 4.42 (s, 1H), 4.36-4.29 (m, 1H), 3.87 (s, 3H), 3.01-2.92 (m, 1H), 1.99-1.92 (m, 1H), 1.69-1.60 (m, 1H), 1.41-1.34 (m, 1H).

Example 77: rac-(1R,2R,4S,5R,6S)—N-(3-cyano-5-(trifluoromethyl)phenyl)-4-(2-fluoropyridin-4-yl)-6-hydroxy-8-oxatricyclo[3.2.1.0²,⁴]octane-2-carboxamide

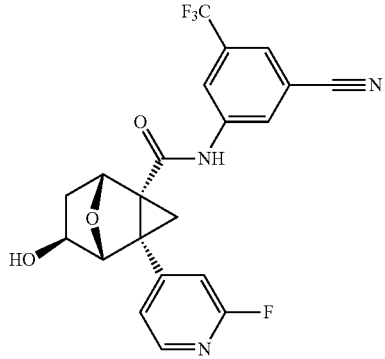 [SMILES: N#Cc1cc(NC(=O)[C@]23C[C@@]2(c2ccnc(F)c2)[C@H]2O[C@@H]3C[C@@H]2O)cc(C(F)(F)F)c1]

Method B: LC-MS: Rt=1.05 min; MS m/z [M+H]⁺ 434.1. ¹H NMR (400 MHz, Chloroform-d) δ 8.23-8.17 (m, 1H), 8.08-8.03 (m, 1H), 7.93-7.88 (m, 1H), 7.69-7.64 (m, 1H), 7.37 (s, 1H), 7.09-7.02 (m, 1H), 6.90-6.84 (m, 1H), 4.77-4.72 (m, 1H), 4.45 (s, 1H), 4.44-4.36 (m, 1H), 3.12-3.02 (m, 1H), 2.14-2.09 (m, 1H), 1.83-1.73 (m, 2H), 1.21-1.17 (m, 1H).

Example 78: rac-(1R,2R,4S,5R,6S)—N-(2-cyano-5-(trifluoromethyl)phenyl)-4-(2-fluoropyridin-4-yl)-6-hydroxy-8-oxatricyclo[3.2.1.0²,⁴]octane-2-carboxamide

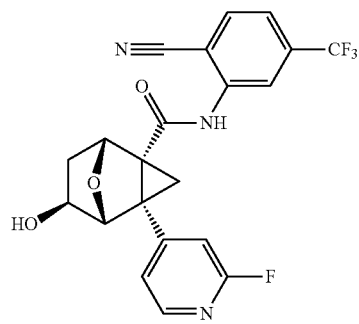 [SMILES: N#Cc1ccc(C(F)(F)F)cc1NC(=O)[C@]12C[C@@]1(c1ccnc(F)c1)[C@H]1O[C@@H]2C[C@@H]1O]

Method B: LC-MS: Rt=0.94 min; MS m/z [M+H]⁺ 434.1.
¹H NMR (400 MHz, DMSO-d6) δ 10.22 (s, 1H), 8.14-8.09 (m, 2H), 7.86-7.83 (m, 1H), 7.81-7.76 (m, 1H), 7.28-7.23 (m, 1H), 7.13-7.09 (m, 1H), 5.01-4.96 (m, 1H), 4.81-4.75 (m, 1H), 4.37 (s, 1H), 4.19-4.12 (m, 1H), 2.79-2.71 (m, 1H), 1.89-1.84 (m, 1H), 1.62-1.50 (m, 1H), 1.42-1.37 (m, 1H).

Example 79: rac-(1R,2R,4S,5R,6S)—N-(4-cyano-3-(trifluoromethyl)phenyl)-6-hydroxy-4-(3-(trifluoromethyl)phenyl)-8-oxatricyclo[3.2.1.0²,⁴]octane-2-carboxamide

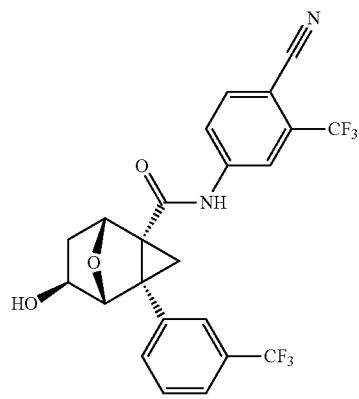 [SMILES: N#Cc1ccc(NC(=O)[C@]23C[C@@]2(c2cccc(C(F)(F)F)c2)[C@H]2O[C@@H]3C[C@@H]2O)cc1C(F)(F)F]

Method B: LC-MS: Rt=1.26 min; MS m/z [M+H]⁺ 483.0.
¹H NMR (400 MHz, Chloroform-d) δ 7.75-7.40 (m, 6H), 6.72 (s, 1H), 4.83-4.77 (m, 1H), 4.45-4.36 (m, 2H), 3.01-2.91 (m, 1H), 2.21-2.15 (m, 1H), 1.87-1.73 (m, 2H), 1.26 (s, 1H), 1.20-1.14 (m, 1H).

Example 80: rac-(1R,2R,4S,5R,6S)—N-(2-cyano-5-(trifluoromethyl)phenyl)-6-hydroxy-4-(3-(trifluoromethyl)phenyl)-8-oxatricyclo[3.2.1.0²,⁴]octane-2-carboxamide

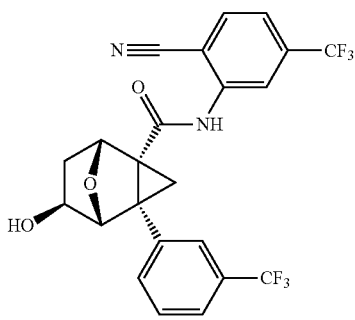 [SMILES: N#Cc1ccc(C(F)(F)F)cc1NC(=O)[C@]12C[C@@]1(c1cccc(C(F)(F)F)c1)[C@H]1O[C@@H]2C[C@@H]1O]

Method B: LC-MS: Rt=1.15 min; MS m/z [M+H]⁺ 483.1.
¹H NMR (400 MHz, Methanol-d₄) δ 7.97-7.91 (m, 1H), 7.83-7.78 (m, 1H), 7.71-7.56 (m, 4H), 7.56-7.48 (m, 1H), 4.82-4.79 (m, 1H), 4.39-4.30 (m, 2H), 3.09-3.00 (m, 1H), 2.06-2.03 (m, 1H), 1.83-1.73 (m, 1H), 1.45-1.37 (m, 1H).

Example 81: rac-(1R,2R,4S,5R,6S)—N-(2-fluoro-5-(trifluoromethyl)phenyl)-6-hydroxy-4-(3-(trifluoromethyl)phenyl)-8-oxatricyclo[3.2.1.0²,⁴]octane-2-carboxamide

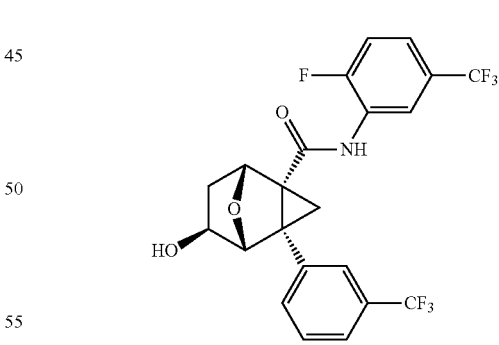

Method B: LC-MS: Rt=1.27 min; MS m/z [M+H]⁺ 476.0.
¹H NMR (400 MHz, Chloroform-d) δ 8.56-8.48 (m, 1H), 7.65-7.60 (m, 1H), 7.60-7.57 (m, 1H), 7.54-7.44 (m, 2H), 7.33-7.27 (m, 1H), 7.11-7.04 (m, 1H), 6.74-6.65 (m, 1H), 4.83-4.79 (m, 1H), 4.46-4.40 (m, 1H), 4.37 (s, 1H), 3.00-2.92 (m, 1H), 2.19-2.13 (m, 1H), 1.86-1.75 (m, 2H), 1.21-1.16 (m, 1H).

Example 82: rac-(1R,2R,4S,5R,6S)-6-hydroxy-4-(3-(trifluoromethyl)phenyl)-N-(4-(trifluoromethyl)pyridin-2-yl)-8-oxatricyclo[3.2.1.02,4]octane-2-carboxamide

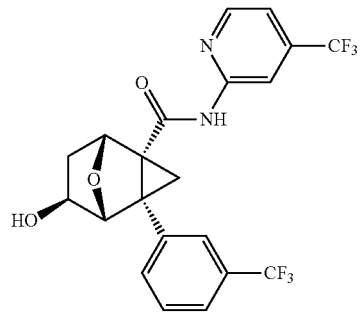 [SMILES: O=C(Nc1cc(C(F)(F)F)ccn1)[C@]12C[C@@]1(c1cccc(C(F)(F)F)c1)[C@H]1O[C@@H]2C[C@@H]1O]

Method B: LC-MS: Rt=1.24 min; MS m/z [M+H]$^+$ 459.1. $^1$H NMR (400 MHz, Chloroform-d) δ 8.45-8.38 (m, 1H), 8.35-8.29 (m, 1H), 7.63-7.52 (m, 3H), 7.52-7.40 (m, 2H), 7.25-7.20 (m, 1H), 4.82-4.76 (m, 1H), 4.43-4.34 (m, 2H), 3.07-2.97 (m, 1H), 2.17-2.09 (m, 1H), 1.90-1.78 (m, 2H), 1.30-1.21 (m, 1H).

Biological Assays

The compounds of the present invention were evaluated in the Alkaline Phosphatase (ALP) activity assay to determine the ability of the compounds to prevent chondrocyte hypertrophy in normal human articular chondrocytes (NHACs). The reagents used are listed in Table 1.

TABLE 1

| Description | Company | Catalog number | Dilution/Concentration |
|---|---|---|---|
| Hoescht 33342 | Life Technologies | H3570 | 1:1000 |
| Fast Blue RR Salt | Sigma | F0500-25G | 0.024% w/v |

TABLE 1-continued

| Description | Company | Catalog number | Dilution/Concentration |
|---|---|---|---|
| Naphthol AS-MX Phosphate Alkaline Solution | Sigma | 855-20ML | 4% v/v |

Cell Culture

Normal human articular chondrocytes (NHACs) were purchased from PromoCell (Heidelberg, Germany) and grown in Chondrocyte Growth Medium (CGM; Lonza, Walkersville, Md.).

Alkaline Phosphatase Staining and Quantitation in NHACs

NHACs were expanded in Chondrocyte Growth Medium (CGM) from Lonza until they reached a 60-80% confluency. To initiate differentiation, 7,500 cells were plated/well with indicated test compound dose in 384-well Cell Carrier Ultra plates (Perkin Elmer) with DMEM (SH30022—HyClone) containing 10% FBS (35-015-CV—Corning), 1% Pen/Strep antibiotics (SV30010—HyClone), and 1% Normocin (50 mg/mL—InvivoGen). Cells with test compounds were incubated at 37° C., 5% CO2 for 5 hours and then added human IL-1 beta (AF-200-1B—Peprotech) to each well at a final concentration of 10 ng/mL and incubated at 37° C., 5% CO2 for 12 days.

To detect the presence of hypertrophic cells, NHACs were fixed with 4% paraformaldehyde and Hoechst 33342 (Invitrogen) dye for 30 minutes, rinsed in PBS, then stained with Fast Blue RR Salt (F0500—Sigma) with Naphthol AS-MX Phosphate Alkaline Solution, 0.25% (855—Sigma-Aldrich). Once cells were observed to turn blue, after approximately 3 hours at 37° C., they were washed with PBS three times.

The staining was imaged by fluoresecent microscopy, using the 561 nm wavelength, and/or quantified by high content imaging with the ImageXpress Confocal (Molecular Devices, Sunnyvale, CA). Data analyses were performed with a customized multiwavelength cell-scoring application The activity of the compounds of the present invention in the ALP assay is summarized in Table 2.

TABLE 2

| Example No. | Chemical name | ALP in NHAC IC$_{50}$ μM (% Efficacy) |
|---|---|---|
| 1 | rac-(1R,2R,4S,5R,6S)-4-(2-fluoropyridin-4-yl)-6-hydroxy-N-(4-(trifluoromethyl)pyridin-2-yl)-8-oxatricyclo[3.2.1.02,4]octane-2-carboxamide | >30 (28) |
| 2 | rac-(1R,2R,4S,5R,6S)-N-(3-fluoro-4-(trifluoromethyl)phenyl)-4-(2-fluoropyridin-4-yl)-6-hydroxy-8-oxatricyclo[3.2.1.02,4]octane-2-carboxamide | >30 (28) |
| 3 | rac-(1R,2R,4S,5R,6S)-N-(3-chloro-4-(trifluoromethyl)phenyl)-4-(2-fluoropyridin-4-yl)-6-hydroxy-8-oxatricyclo[3.2.1.02,4]octane-2-carboxamide | 12 (71) |
| 4 | rac-(1R,2R,4S,5R,6S)-N-(6-chloro-4-(trifluoromethyl)pyridin-2-yl)-4-(2-fluoropyridin-4-yl)-6-hydroxy-8-oxatricyclo[3.2.1.02,4]octane-2-carboxamide | >30 (0) |
| 5 | rac-(1R,2R,4S,5R,6S)-N-(5-chloro-4-(trifluoromethyl)pyridin-2-yl)-4-(2-fluoropyridin-4-yl)-6-hydroxy-8-oxatricyclo[3.2.1.02,4]octane-2-carboxamide | >30 (38) |
| 6 | rac-(1R,2R,4S,5R,6S)-N-(6-cyclopropyl-4-(trifluoromethyl)pyridin-2-yl)-4-(2-fluoropyridin-4-yl)-6-hydroxy-8-oxatricyclo[3.2.1.02,4]octane-2-carboxamide | >30 (9) |
| 7 | rac-(1R,2R,4S,5R,6S)-4-(2-fluoropyridin-4-yl)-6-hydroxy-N-(6-methyl-4-(trifluoromethyl)pyridin-2-yl)-8-oxatricyclo(3.2.1.02,4)octane-2-carboxamide | >30 (0) |

TABLE 2-continued

| Example No. | Chemical name | ALP in NHAC IC$_{50}$ μM (% Efficacy) |
|---|---|---|
| 8 | rac-(1R,2R,4S,5R,6S)-N-(6-ethoxy-4-(trifluoromethyl)pyridin-2-yl)-4-(2-fluoropyridin-4-yl)-6-hydroxy-8-oxatricyclo[3.2.1.0²,⁴]octane-2-carboxamide | >30 (26) |
| 9 | rac-(1R,2R,4S,5R,6S)-4-(2-fluoropyridin-4-yl)-6-hydroxy-N-(3-(trifluoromethyl)phenyl)-8-oxatricyclo[3.2.1.0²,⁴]octane-2-carboxamide | >30 (32) |
| 10 | rac-(1R,2R,4S,5R,6S)-4-(2-fluoropyridin-4-yl)-6-hydroxy-N-(2-methyl-3-(trifluoromethyl)phenyl)-8-oxatricyclo[3.2.1.0²,⁴]octane-2-carboxamide | >30 (6) |
| 11 | rac-(1R,2R,4S,5R,6S)-4-(2-fluoropyridin-4-yl)-6-hydroxy-N-(4-methyl-3-(trifluoromethyl)phenyl)-8-oxatricyclo[3.2.1.0²,⁴]octane-2-carboxamide | >30 (0) |
| 12 | rac-(1R,2R,4S,5R,6S)-4-(2-fluoropyridin-4-yl)-6-hydroxy-N-(3-methyl-5-(trifluoromethyl)phenyl)-8-oxatricyclo[3.2.1.0²,⁴]octane-2-carboxamide | >30 (21) |
| 13 | rac-(1R,2R,4S,5R,6S)-4-(2-fluoropyridin-4-yl)-6-hydroxy-N-(2-methyl-5-(trifluoromethyl)phenyl)-8-oxatricyclo[3.2.1.0²,⁴]octane-2-carboxamide | >30 (40) |
| 14 | rac-(1R,2R,4S,5R,6S)-N-(2-fluoro-3-(trifluoromethyl)phenyl)-4-(2-fluoropyridin-4-yl)-6-hydroxy-8-oxatricyclo[3.2.1.0²,⁴]octane-2-carboxamide | >30 (8) |
| 15 | rac-(1R,2R,4S,5R,6S)-N-(4-fluoro-3-(trifluoromethyl)phenyl)-4-(2-fluoropyridin-4-yl)-6-hydroxy-8-oxatricyclo[3.2.1.0²,⁴]octane-2-carboxamide | >30 (5) |
| 16 | rac-(1R,2R,4S,5R,6S)-N-(3-fluoro-5-(trifluoromethyl)phenyl)-4-(2-fluoropyridin-4-yl)-6-hydroxy-8-oxatricyclo[3.2.1.0²,⁴]octane-2-carboxamide | >30 (34) |
| 17 | rac-(1R,2R,4S,5R,6S)-N-(2-fluoro-5-(trifluoromethyl)phenyl)-4-(2-fluoropyridin-4-yl)-6-hydroxy-8-oxatricyclo[3.2.1.0²,⁴]octane-2-carboxamide | >30 (17) |
| 18 | rac-(1R,2R,4S,5R,6S)-N-(4-chloro-3-(trifluoromethyl)phenyl)-4-(2-fluoropyridin-4-yl)-6-hydroxy-8-oxatricyclo[3.2.1.0²,⁴]octane-2-carboxamide | >30 (25) |
| 19 | rac-(1R,2R,4S,5R,6S)-N-(3-chloro-5-(trifluoromethyl)phenyl)-4-(2-fluoropyridin-4-yl)-6-hydroxy-8-oxatricyclo[3.2.1.0²,⁴]octane-2-carboxamide | >30 (0) |
| 20 | rac-(1R,2R,4S,5R,6S)-6-hydroxy-4-(2-methoxypyridin-4-yl)-N-(4-(trifluoromethyl)pyridin-2-yl)-8-oxatricyclo[3.2.1.0²,⁴]octane-2-carboxamide | >30 (24) |
| 21 | rac-(1R,2R,4S,5R,6S)-N-(6-chloro-4-(trifluoromethyl)pyridin-2-yl)-6-hydroxy-4-(2-methoxypyridin-4-yl)-8-oxatricyclo[3.2.1.0²,⁴]octane-2-carboxamide | >30 (0) |
| 22 | rac-(1R,2R,4S,5R,6S)-N-(5-chloro-4-(trifluoromethyl)pyridin-2-yl)-6-hydroxy-4-(2-methoxypyridin-4-yl)-8-oxatricyclo[3.2.1.0²,⁴]octane-2-carboxamide | >30 (27) |
| 23 | rac-(1R,2R,4S,5R,6S)-N-(6-cyclopropyl-4-(trifluoromethyl)pyridin-2-yl)-6-hydroxy-4-(2-methoxypyridin-4-yl)-8-oxatricyclo[3.2.1.0²,⁴]octane-2-carboxamide | >30 (4) |
| 24 | rac-(1R,2R,4S,5R,6S)-6-hydroxy-4-(2-methoxypyridin-4-yl)-N-(6-methyl-4-(trifluoromethyl)pyridin-2-yl)-8-oxatricyclo[3.2.1.0²,⁴]octane-2-carboxamide | >30 (25) |
| 25 | rac-(1R,2R,4S,5R,6S)-N-(6-ethoxy-4-(trifluoromethyl)pyridin-2-yl)-6-hydroxy-4-(2-methoxypyridin-4-yl)-8-oxatricyclo[3.2.1.0²,⁴]octane-2-carboxamide | >30 (0) |
| 26 | rac-(1R,2R,4S,5R,6S)-6-hydroxy-4-(2-methoxypyridin-4-yl)-N-(3-(trifluoromethyl)phenyl)-8-oxatricyclo[3.2.1.0²,⁴]octane-2-carboxamide | >30 (5) |
| 27 | rac-(1R,2R,4S,5R,6S)-6-hydroxy-4-(2-methoxypyridin-4-yl)-N-(2-methyl-3-(trifluoromethyl)phenyl)-8-oxatricyclo[3.2.1.0²,⁴]octane-2-carboxamide | >30 (0) |
| 28 | rac-(1R,2R,4S,5R,6S)-6-hydroxy-4-(2-methoxypyridin-4-yl)-N-(4-methyl-3-(trifluoromethyl)phenyl)-8-oxatricyclo[3.2.1.0²,⁴]octane-2-carboxamide | >30 (13) |
| 29 | rac-(1R,2R,4S,5R,6S)-6-hydroxy-4-(2-methoxypyridin-4-yl)-N-(3-methyl-5-(trifluoromethyl)phenyl)-8-oxatricyclo[3.2.1.0²,⁴]octane-2-carboxamide | 10 (74) |
| 30 | rac-(1R,2R,4S,5R,6S)-6-hydroxy-4-(2-methoxypyridin-4-yl)-N-(2-methyl-5-(trifluoromethyl)phenyl)-8-oxatricyclo[3.2.1.0²,⁴]octane-2-carboxamide | >30 (27) |
| 31 | rac-(1R,2R,4S,5R,6S)-N-(2-fluoro-3-(trifluoromethyl)phenyl)-6-hydroxy-4-(2-methoxypyridin-4-yl)-8-oxatricyclo[3.2.1.0²,⁴]octane-2-carboxamide | >30 (15) |
| 32 | rac-(1R,2R,4S,5R,6S)-N-(4-fluoro-3-(trifluoromethyl)phenyl)-6-hydroxy-4-(2-methoxypyridin-4-yl)-8-oxatricyclo[3.2.1.0²,⁴]octane-2-carboxamide | >30 (4) |

TABLE 2-continued

| Example No. | Chemical name | ALP in NHAC IC$_{50}$ μM (% Efficacy) |
|---|---|---|
| 33 | rac-(1R,2R,4S,5R,6S)-N-(2-fluoro-5-(trifluoromethyl)phenyl)-6-hydroxy-4-(2-methoxypyridin-4-yl)-8-oxatricyclo[3.2.1.0²,⁴]octane-2-carboxamide | >30 (12) |
| 34 | rac-(1R,2R,4S,5R,6S)-6-hydroxy-N-(4-methoxy-3-(trifluoromethyl)phenyl)-4-(2-methoxypyridin-4-yl)-8-oxatricyclo[3.2.1.0²,⁴]octane-2-carboxamide | >30 (0) |
| 35 | rac-(1R,2R,4S,5R,6S)-6-hydroxy-N-(3-methoxy-5-(trifluoromethyl)phenyl)-4-(2-methoxypyridin-4-yl)-8-oxatricyclo[3.2.1.0²,⁴]octane-2-carboxamide | >30 (0) |
| 36 | rac-(1R,2R,4S,5R,6S)-6-hydroxy-N-(2-methoxy-5-(trifluoromethyl)phenyl)-4-(2-methoxypyridin-4-yl)-8-oxatricyclo[3.2.1.0²,⁴]octane-2-carboxamide | 18 (65) |
| 37 | rac-(1R,2R,4S,5R,6S)-N-(3,5-bis(trifluoromethyl)phenyl)-6-hydroxy-4-(2-methoxypyridin-4-yl)-8-oxatricyclo[3.2.1.0²,⁴]octane-2-carboxamide | >30 (0) |
| 38 | rac-(1R,2R,4S,5R,6S)-N-(4-cyano-3-(trifluoromethyl)phenyl)-6-hydroxy-4-(2-methoxypyridin-4-yl)-8-oxatricyclo[3.2.1.0²,⁴]octane-2-carboxamide | 24 (71) |
| 39 | rac-(1R,2R,4S,5R,6S)-N-(2-cyano-5-(trifluoromethyl)phenyl)-6-hydroxy-4-(2-methoxypyridin-4-yl)-8-oxatricyclo[3.2.1.0²,⁴]octane-2-carboxamide | 0.081 (92) |
| 39a | (1R,2R,4S,5R,6S)-N-(2-cyano-5-(trifluoromethyl)phenyl)-6-hydroxy-4-(2-methoxypyridin-4-yl)-8-oxatricyclo[3.2.1.0²,⁴]octane-2-carboxamide or (1S,2S,4R,5S,6R)-N-(2-cyano-5-(trifluoromethyl)phenyl)-6-hydroxy-4-(2-methoxypyridin-4-yl)-8-oxatricyclo[3.2.1.0²,⁴]octane-2-carboxamide | 0.29 (90) |
| 39b | (1R,2R,4S,5R,6S)-N-(2-cyano-5-(trifluoromethyl)phenyl)-6-hydroxy-4-(2-methoxypyridin-4-yl)-8-oxatricyclo[3.2.1.0²,⁴]octane-2-carboxamide or (1S,2S,4R,5S,6R)-N-(2-cyano-5-(trifluoromethyl)phenyl)-6-hydroxy-4-(2-methoxypyridin-4-yl)-8-oxatricyclo[3.2.1.0²,⁴]octane-2-carboxamide | 0.25 (97) |
| 40 | rac-(1R,2R,4S,5R,6S)-N-(3-chloro-4-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide | 9.5 (91) |
| 41 | rac-(1R,2R,4S,5R,6S)-N-(3-fluoro-4-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide | 3.1 (84) |
| 42 | rac-(1R,2R,4S,5R,6S)-6-hydroxy-4-(1-methyl-3-(trifluoromethyl)-1H-pyrazol-4-yl)-N-(4-(trifluoromethyl)phenyl)-8-oxatricyclo[3.2.1.0²,⁴]octane-2-carboxamide | >30 (46) |
| 43 | rac-(1R,2R,4S,5R,6S)-6-hydroxy-4-(1-methyl-3-(trifluoromethyl)-1H-pyrazol-4-yl)-N-(4-(trifluoromethyl)pyridin-2-yl)-8-oxatricyclo[3.2.1.0²,⁴]octane-2-carboxamide | >30 (49) |
| 44 | rac-(1R,2R,4S,5R,6S)-N-(6-chloro-4-(trifluoromethyl)pyridin-2-yl)-6-hydroxy-4-(1-methyl-3-(trifluoromethyl)-1H-pyrazol-4-yl)-8-oxatricyclo[3.2.1.0²,⁴]octane-2-carboxamide | >30 (37) |
| 45 | rac-(1R,2R,4S,5R,6S)-N-(5-chloro-4-(trifluoromethyl)pyridin-2-yl)-6-hydroxy-4-(1-methyl-3-(trifluoromethyl)-1H-pyrazol-4-yl)-8-oxatricyclo[3.2.1.0²,⁴]octane-2-carboxamide | >30 (46) |
| 46 | rac-(1R,2R,4S,5R,6S)-N-(6-cyclopropyl-4-(trifluoromethyl)pyridin-2-yl)-6-hydroxy-4-(1-methyl-3-(trifluoromethyl)-1H-pyrazol-4-yl)-8-oxatricyclo[3.2.1.0²,⁴]octane-2-carboxamide | 27 (82) |
| 47 | rac-(1R,2R,4S,5R,6S)-6-hydroxy-4-(1-methyl-3-(trifluoromethyl)-1H-pyrazol-4-yl)-N-(6-methyl-4-(trifluoromethyl)pyridin-2-yl)-8-oxatricyclo[3.2.1.0²,⁴]octane-2-carboxamide | >30 (36) |
| 48 | rac-(1R,2R,4S,5R,6S)-N-(6-ethoxy-4-(trifluoromethyl)pyridin-2-yl)-6-hydroxy-4-(1-methyl-3-(trifluoromethyl)-1H-pyrazol-4-yl)-8-oxatricyclo[3.2.1.0²,⁴]octane-2-carboxamide | >30 (40) |
| 49 | rac-(1R,2R,4S,5R,6S)-6-hydroxy-4-(1-methyl-3-(trifluoromethyl)-1H-pyrazol-4-yl)-N-(3-(trifluoromethyl)phenyl)-8-oxatricyclo[3.2.1.0²,⁴]octane-2-carboxamide | >30 (35) |
| 50 | rac-(1R,2R,4S,5R,6S)-6-hydroxy-4-(1-methyl-3-(trifluoromethyl)-1H-pyrazol-4-yl)-N-(2-methyl-3-(trifluoromethyl)phenyl)-8-oxatricyclo[3.2.1.0²,⁴]octane-2-carboxamide | >30 (33) |
| 51 | rac-(1R,2R,4S,5R,6S)-6-hydroxy-4-(1-methyl-3-(trifluoromethyl)-1H-pyrazol-4-yl)-N-(4-methyl-3-(trifluoromethyl)phenyl)-8-oxatricyclo[3.2.1.0²,⁴]octane-2-carboxamide | >30 (45) |
| 52 | rac-(1R,2R,4S,5R,6S)-6-hydroxy-4-(1-methyl-3-(trifluoromethyl)-1H-pyrazol-4-yl)-N-(3-methyl-5-(trifluoromethyl)phenyl)-8-oxatricyclo[3.2.1.0²,⁴]octane-2-carboxamide | 21 (70) |
| 53 | rac-(1R,2R,4S,5R,6S)-6-hydroxy-4-(1-methyl-3-(trifluoromethyl)-1H-pyrazol-4-yl)-N-(2-methyl-5-(trifluoromethyl)phenyl)-8-oxatricyclo[3.2.1.0²,⁴]octane-2-carboxamide | >30 (23) |

TABLE 2-continued

| Example No. | Chemical name | ALP in NHAC IC$_{50}$ μM (% Efficacy) |
|---|---|---|
| 54 | rac-(1R,2R,4S,5R,6S)-N-(2-fluoro-3-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide | >30 (7) |
| 55 | rac-(1R,2R,4S,5R,6S)-N-(4-fluoro-3-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide | >30 (14) |
| 56 | rac-(1R,2R,4S,5R,6S)-N-(3-fluoro-5-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide | >30 (30) |
| 57 | rac-(1R,2R,4S,5R,6S)-N-(2-fluoro-5-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide | >30 (24) |
| 58 | rac-(1R,2R,4S,5R,6S)-N-(4-chloro-3-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide | >30 (29) |
| 59 | rac-(1R,2R,4S,5R,6S)-N-(3-chloro-5-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide | >30 (35) |
| 60 | rac-(1R,2R,4S,5R,6S)-6-hydroxy-N-(4-methoxy-3-(trifluoromethyl)phenyl)-4-(1-methyl-3-(trifluoromethyl)-1H-pyrazol-4-yl)-8-oxatricyclo[3.2.1.0²,⁴]octane-2-carboxamide | >30 (27) |
| 61 | rac-(1R,2R,4S,5R,6S)-6-hydroxy-N-(3-methoxy-5-(trifluoromethyl)phenyl)-4-(1-methyl-3-(trifluoromethyl)-1H-pyrazol-4-yl)-8-oxatricyclo[3.2.1.0²,⁴]octane-2-carboxamide | >30 (29) |
| 62 | rac-(1R,2R,4S,5R,6S)-6-hydroxy-N-(2-methoxy-5-(trifluoromethyl)phenyl)-4-(1-methyl-3-(trifluoromethyl)-1H-pyrazol-4-yl)-8-oxatricyclo[3.2.1.0²,⁴]octane-2-carboxamide | >30 (26) |
| 63 | rac-(1R,2R,4S,5R,6S)-N-(3,5-bis(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide | 29 (56) |
| 64 | rac-(1R,2R,4S,5R,6S)-6-hydroxy-4-(1-methyl-3-(trifluoromethyl)-1H-pyrazol-4-yl)-N-(4-morpholino-3-(trifluoromethyl)phenyl)-8-oxatricyclo[3.2.1.0²,⁴]octane-2-carboxamide | >30 (28) |
| 65 | rac-(1R,2R,4S,5R,6S)-N-(4-ethoxy-3-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide | 12 (84) |
| 66 | rac-(1R,2R,4S,5R,6S)-6-hydroxy-N-(3-(trifluoromethyl)phenyl)-4-(2-(trifluoromethyl)pyridin-4-yl)-8-oxatricyclo[3.2.1.0²,⁴]octane-2-carboxamide | 24 (62) |
| 67 | rac-(1R,2R,4S,5R,6S)-6-hydroxy-N,4-bis(3-(trifluoromethyl)phenyl)-8-oxatricyclo[3.2.1.0²,⁴]octane-2-carboxamide | 27 (54) |
| 68 | rac-(1R,2R,4S,5R,6S)-N-(4-cyano-3-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide | >30 (50) |
| 69 | rac-(1R,2R,4S,5R,6S)-N-(2-cyano-5-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide | 1.8 (88) |
| 70 | rac-(1R,2R,4S,5R,6S)-N-(4-chloro-3-(trifluoromethyl)phenyl)-6-hydroxy-4-(2-methoxypyridin-4-yl)-8-oxatricyclo[3.2.1.0²,⁴]octane-2-carboxamide | >30 (39) |
| 71 | rac-(1R,2R,4S,5R,6S)-N-(3-chloro-5-(trifluoromethyl)phenyl)-6-hydroxy-4-(2-methoxypyridin-4-yl)-8-oxatricyclo[3.2.1.0²,⁴]octane-2-carboxamide | >30 (9) |
| 72 | rac-(1R,2R,4S,5R,6S)-N-(3-cyano-5-(trifluoromethyl)phenyl)-6-hydroxy-4-(2-methoxypyridin-4-yl)-8-oxatricyclo(3.2.1.0²,⁴]octane-2-carboxamide | >30 (37) |
| 73 | rac-(1R,2R,4S,5R,6S)-N-(3-fluoro-5-(trifluoromethyl)phenyl)-6-hydroxy-4-(2-methoxypyridin-4-yl)-8-oxatricyclo[3.2.1.0²,⁴]octane-2-carboxamide | >30 (49) |
| 74 | rac-(1R,2R,4S,5R,6S)-N-(3-chloro-4-(trifluoromethyl)phenyl)-6-hydroxy-4-(2-methoxypyridin-4-yl)-8-oxatricyclo[3.2.1.0²,⁴]octane-2-carboxamide | 3.4 (77) |
| 75 | rac-(1R,2R,4S,5R,6S)-N-(3-fluoro-4-(trifluoromethyl)phenyl)-6-hydroxy-4-(2-methoxypyridin-4-yl)-8-oxatricyclo[3.2.1.0²,⁴]octane-2-carboxamide | >30 (26) |
| 76 | rac-(1R,2R,4S,5R,6S)-6-hydroxy-4-(2-methoxypyridin-4-yl)-N-(4-(trifluoromethyl)phenyl)-8-oxatricyclo[3.2.1.0²,⁴]octane-2-carboxamide | 15 (57) |
| 77 | rac-(1R,2R,4S,5R,6S)-N-(3-cyano-5-(trifluoromethyl)phenyl)-4-(2-fluoropyridin-4-yl)-6-hydroxy-8-oxatricyclo[3.2.1.0²,⁴]octane-2-carboxamide | >30 (29) |
| 78 | rac-(1R,2R,4S,5R,6S)-N-(2-cyano-5-(trifluoromethyl)phenyl)-4-(2-fluoropyridin-4-yl)-6-hydroxy-8-oxatricyclo[3.2.1.0²,⁴]octane-2-carboxamide | >30 (40) |

TABLE 2-continued

| Example No. | Chemical name | ALP in NHAC IC$_{50}$ µM (% Efficacy) |
|---|---|---|
| 79 | rac-(1R,2R,4S,5R,6S)-N-(4-cyano-3-(trifluoromethyl)phenyl)-6-hydroxy-4-(3-(trifluoromethyl)phenyl)-8-oxatricyclo[3.2.1.02,4]octane-2-carboxamide | 9.9 (78) |
| 80 | rac-(1R,2R,4S,5R,6S)-N-(2-cyano-5-(trifluoromethyl)phenyl)-6-hydroxy-4-(3-(trifluoromethyl)phenyl)-8-oxatricyclo[3.2.1.02,4]octane-2-carboxamide | 2.2 (76) |
| 81 | rac-(1R,2R,4S,5R,6S)-N-(2-fluoro-5-(trifluoromethyl)phenyl)-6-hydroxy-4-(3-(trifluoromethyl)phenyl)-8-oxatricyclo[3.2.1.02,4]octane-2-carboxamide | >30 (47) |
| 82 | rac-(1R,2R,4S,5R,6S)-6-hydroxy-4-(3-(trifluoromethyl)phenyl)-N-(4-(trifluoromethyl)pyridin-2-yl)-8-oxatricyclo[3.2.1.02,4]octane-2-carboxamide | >30 (36) |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

The invention claimed is:

1. A compound of Formula (1):

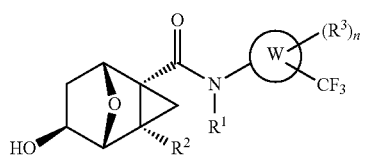

or an enantiomer, an enantiomeric mixture thereof or a pharmaceutically acceptable salt thereof; wherein W is phenyl or pyridyl;

$R^1$ is hydrogen or $C_{1-6}$alkyl;

$R^2$ is phenyl or a 5-6 membered heteroaryl having 1-2 heteroatoms selected from N, O and S; wherein $R^2$ is unsubstituted or substituted by 1-2 substituents independently selected from halo, $C_{1-6}$ alkyl, $C_{1-6}$ haloalkyl or $C_{1-6}$ alkoxy;

$R^3$ is independently selected from halo, cyano, $C_{1-6}$alkyl, $C_{1-6}$haloalkyl, $C_{1-6}$alkoxy, $C_{3-6}$ cycloalkyl and 5-6 membered heterocyclyl; or $R^3$ is hydrogen when n is 0; and n is 0-2.

2. The compound according to claim 1 or an enantiomer, an enantiomeric mixture thereof or a pharmaceutically acceptable salt thereof; wherein

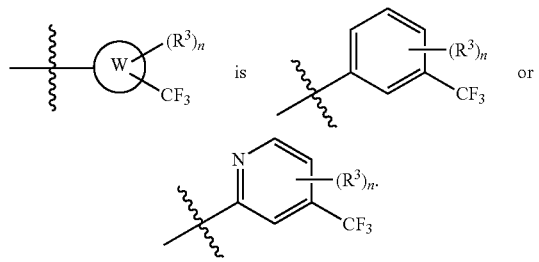

3. The compound according to claim 1 or an enantiomer, an enantiomeric mixture thereof or a pharmaceutically acceptable salt thereof; wherein

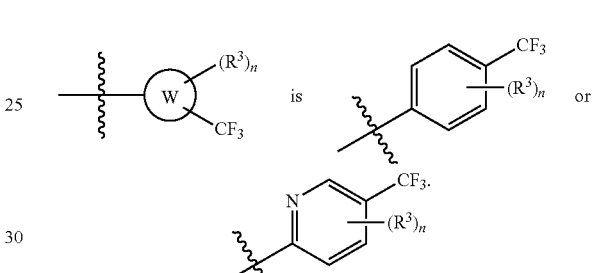

4. The compound according to claim 1 or an enantiomer, an enantiomeric mixture thereof or a pharmaceutically acceptable salt thereof; wherein

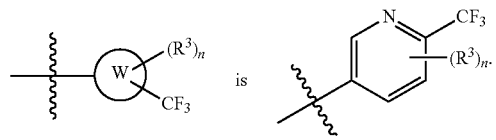

5. The compound according to claim 1, wherein said compound is of Formula (2):

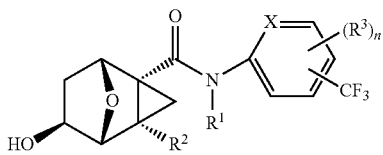

or an enantiomer, an enantiomeric mixture thereof or a pharmaceutically acceptable salt thereof; wherein X is N, CH or $CR^4$; wherein $R^4$ is halo, cyano, $C_{1-6}$alkyl, $C_{1-6}$haloalkyl or $C_{1-6}$alkoxy.

6. The compound according to claim 1 or an enantiomer, an enantiomeric mixture thereof or a pharmaceutically acceptable salt thereof; wherein $R^3$, if present, is fluoro, chloro, methyl, methoxy, ethoxy, trifluomethyl, cyano, cyclopropyl or morpholinyl.

7. The compound according to claim 1 or an enantiomer, an enantiomeric mixture thereof or a pharmaceutically acceptable salt thereof; wherein $R^3$ is hydrogen and n is 0.

8. The compound according to claim 1 or an enantiomer, an enantiomeric mixture thereof or a pharmaceutically acceptable salt thereof; wherein $R^2$ is phenyl, pyrazolyl, pyridyl or pyrimidinyl; each of which is substituted by 1-2 substituents independently selected from halo, $C_{1-6}$ alkyl, $C_{1-6}$ haloalkyl or $C_{1-6}$ alkoxy.

9. The compound according to claim 8 or an enantiomer, an enantiomeric mixture thereof or a pharmaceutically acceptable salt thereof; wherein $R^2$ is selected from:

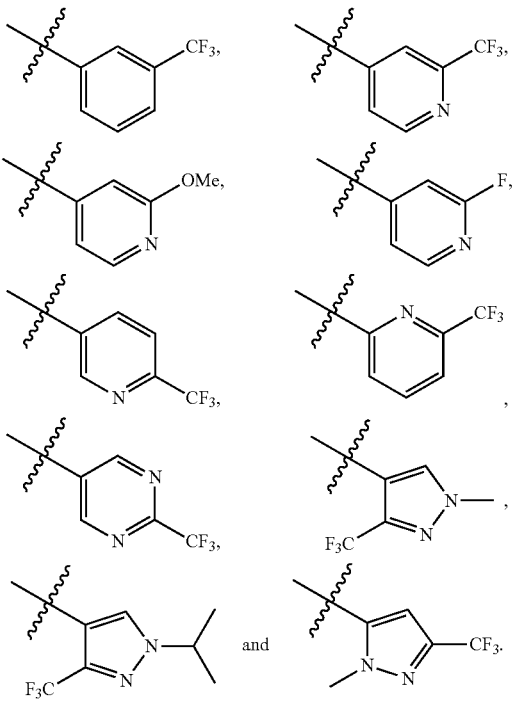

10. The compound according to claim 1 or an enantiomer, an enantiomeric mixture thereof or a pharmaceutically acceptable salt thereof; wherein $R^1$ is hydrogen.

11. The compound according to claim 1, wherein said compound is selected from:
rac-(1R,2R,4S,5R,6S)-4-(2-fluoropyridin-4-yl)-6-hydroxy-N-(4-(trifluoromethyl) pyridin-2-yl)-8-oxatricyclo[3.2.1.0²,⁴]octane-2-carboxamide;
rac-(1R,2R,4S,5R,6S)-N-(3-fluoro-4-(trifluoromethyl)phenyl)-4-(2-fluoropyridin-4-yl)-6-hydroxy-8-oxatricyclo[3.2.1.0²,⁴]octane-2-carboxamide;
rac-(1R,2R,4S,5R,6S)-N-(3-chloro-4-(trifluoromethyl)phenyl)-4-(2-fluoropyridin-4-yl)-6-hydroxy-8-oxatricyclo[3.2.1.0²,⁴]octane-2-carboxamide;
rac-(1R,2R,4S,5R,6S)-N-(6-chloro-4-(trifluoromethyl)pyridin-2-yl)-4-(2-fluoropyridin-4-yl)-6-hydroxy-8-oxatricyclo[3.2. 1.0²,⁴]octane-2-carboxamide;
rac-(1R,2R,4S,5R,6S)-N-(5-chloro-4-(trifluoromethyl)pyridin-2-yl)-4-(2-fluoropyridin-4-yl)-6-hydroxy-8-oxatricyclo[3.2.1.0²,⁴]octane-2-carboxamide;
rac-(1R,2R,4S,5R,6S)-N-(6-cyclopropyl-4-(trifluoromethyl) pyridin-2-yl)-4-(2-fluoropyridin-4-yl)-6-hydroxy-8-oxatricyclo[3.2.1.0²,⁴]octane-2-carboxamide;
rac-(1R,2R,4S,5R,6S)-4-(2-fluoropyridin-4-yl)-6-hydroxy-N-(6-methyl-4-(trifluoromethyl) pyridin-2-yl)-8-oxatricyclo[3.2.1.0²,⁴]octane-2-carboxamide;
rac-(1R,2R,4S,5R,6S)-N-(6-ethoxy-4-(trifluoromethyl)pyridin-2-yl)-4-(2-fluoropyridin-4-yl)-6-hydroxy-8-oxatricyclo[3.2.1.0²,⁴]octane-2-carboxamide;
rac-(1R,2R,4S,5R,6S)-4-(2-fluoropyridin-4-yl)-6-hydroxy-N-(3-(trifluoromethyl)phenyl)-8-oxatricyclo[3.2.1.0²,⁴]octane-2-carboxamide;
rac-(1R,2R,4S,5R,6S)-4-(2-fluoropyridin-4-yl)-6-hydroxy-N-(2-methyl-3-(trifluoromethyl)phenyl)-8-oxatricyclo[3.2.1.0²,⁴]octane-2-carboxamide;
rac-(1R,2R,4S,5R,6S)-4-(2-fluoropyridin-4-yl)-6-hydroxy-N-(4-methyl-3-(trifluoromethyl)phenyl)-8-oxatricyclo[3.2.1.0²,⁴]octane-2-carboxamide;
rac-(1R,2R,4S,5R,6S)-4-(2-fluoropyridin-4-yl)-6-hydroxy-N-(3-methyl-5-(trifluoromethyl)phenyl)-8-oxatricyclo[3.2.1.0²,⁴]octane-2-carboxamide;
rac-(1R,2R,4S,5R,6S)-4-(2-fluoropyridin-4-yl)-6-hydroxy-N-(2-methyl-5-(trifluoromethyl)phenyl)-8-oxatricyclo[3.2.1.0²,⁴]octane-2-carboxamide;
rac-(1R,2R,4S,5R,6S)-N-(2-fluoro-3-(trifluoromethyl)phenyl)-4-(2-fluoropyridin-4-yl)-6-hydroxy-8-oxatricyclo[3.2.1.0²,⁴]octane-2-carboxamide;
rac-(1R,2R,4S,5R,6S)-N-(4-fluoro-3-(trifluoromethyl)phenyl)-4-(2-fluoropyridin-4-yl)-6-hydroxy-8-oxatricyclo[3.2.1.0²,⁴]octane-2-carboxamide;
rac-(1R,2R,4S,5R,6S)-N-(3-fluoro-5-(trifluoromethyl)phenyl)-4-(2-fluoropyridin-4-yl)-6-hydroxy-8-oxatricyclo[3.2.1.0²,⁴]octane-2-carboxamide;
rac-(1R,2R,4S,5R,6S)-N-(2-fluoro-5-(trifluoromethyl)phenyl)-4-(2-fluoropyridin-4-yl)-6-hydroxy-8-oxatricyclo[3.2.1.0²,⁴]octane-2-carboxamide;
rac-(1R,2R,4S,5R,6S)-N-(4-chloro-3-(trifluoromethyl)phenyl)-4-(2-fluoropyridin-4-yl)-6-hydroxy-8-oxatricyclo[3.2.1.0²,⁴]octane-2-carboxamide;
rac-(1R,2R,4S,5R,6S)-N-(3-chloro-5-(trifluoromethyl)phenyl)-4-(2-fluoropyridin-4-yl)-6-hydroxy-8-oxatricyclo[3.2.1.0²,⁴]octane-2-carboxamide;
rac-(1R,2R,4S,5R,6S)-6-hydroxy-4-(2-methoxypyridin-4-yl)-N-(4-(trifluoromethyl)pyridin-2-yl)-8-oxatricyclo[3.2.1.0²,⁴]octane-2-carboxamide;
rac-(1R,2R,4S,5R,6S)-N-(6-chloro-4-(trifluoromethyl)pyridin-2-yl)-6-hydroxy-4-(2-methoxypyridin-4-yl)-8-oxatricyclo[3.2.1.0²,⁴]octane-2-carboxamide;
rac-(1R,2R,4S,5R,6S)-N-(5-chloro-4-(trifluoromethyl)pyridin-2-yl)-6-hydroxy-4-(2-methoxypyridin-4-yl)-8-oxatricyclo[3.2.1.0²,⁴]octane-2-carboxamide;
rac-(1R,2R,4S,5R,6S)-N-(6-cyclopropyl-4-(trifluoromethyl)pyridin-2-yl)-6-hydroxy-4-(2-methoxypyridin-4-yl)-8-oxatricyclo[3.2.1.0²,⁴]octane-2-carboxamide;
rac-(1R,2R,4S,5R,6S)-6-hydroxy-4-(2-methoxypyridin-4-yl)-N-(6-methyl-4-(trifluoromethyl)pyridin-2-yl)-8-oxatricyclo[3.2.1.0²,⁴]octane-2-carboxamide;
rac-(1R,2R,4S,5R,6S)-N-(6-ethoxy-4-(trifluoromethyl)pyridin-2-yl)-6-hydroxy-4-(2-methoxypyridin-4-yl)-8-oxatricyclo[3.2.1.0²,⁴]octane-2-carboxamide;
rac-(1R,2R,4S,5R,6S)-6-hydroxy-4-(2-methoxypyridin-4-yl)-N-(3-(trifluoromethyl)phenyl)-8-oxatricyclo[3.2.1.0²,⁴]octane-2-carboxamide;
rac-(1R,2R,4S,5R,6S)-6-hydroxy-4-(2-methoxypyridin-4-yl)-N-(2-methyl-3-(trifluoromethyl)phenyl)-8-oxatricyclo[3.2.1.0²,⁴]octane-2-carboxamide;
rac-(1R,2R,4S,5R,6S)-6-hydroxy-4-(2-methoxypyridin-4-yl)-N-(4-methyl-3-(trifluoromethyl)phenyl)-8-oxatricyclo[3.2.1.0²,⁴]octane-2-carboxamide;
rac-(1R,2R,4S,5R,6S)-6-hydroxy-4-(2-methoxypyridin-4-yl)-N-(3-methyl-5-(trifluoromethyl)phenyl)-8-oxatricyclo[3.2.1.0²,⁴]octane-2-carboxamide;

rac-(1R,2R,4S,5R,6S)-6-hydroxy-4-(2-methoxypyridin-4-yl)-N-(2-methyl-5-(trifluoromethyl)phenyl)-8-oxatricyclo[3.2.1.0²,⁴]octane-2-carboxamide;

rac-(1R,2R,4S,5R,6S)-N-(2-fluoro-3-(trifluoromethyl)phenyl)-6-hydroxy-4-(2-methoxypyridin-4-yl)-8-oxatricyclo [3.2.1.0²,⁴]octane-2-carboxamide;

rac-(1R,2R,4S,5R,6S)-N-(4-fluoro-3-(trifluoromethyl)phenyl)-6-hydroxy-4-(2-methoxypyridin-4-yl)-8-oxatricyclo[3.2.1.0²,⁴]octane-2-carboxamide;

rac-(1R,2R,4S,5R,6S)-N-(2-fluoro-5-(trifluoromethyl)phenyl)-6-hydroxy-4-(2-methoxypyridin-4-yl)-8-oxatricyclo[3.2.1.0²,⁴]octane-2-carboxamide;

rac-(1R,2R,4S,5R,6S)-6-hydroxy-N-(4-methoxy-3-(trifluoromethyl)phenyl)-4-(2-methoxypyridin-4-yl)-8-oxatricyclo[3.2.1.0²,⁴]octane-2-carboxamide;

rac-(1R,2R,4S,5R,6S)-6-hydroxy-N-(3-methoxy-5-(trifluoromethyl)phenyl)-4-(2-methoxypyridin-4-yl)-8-oxatricyclo[3.2.1.0²,⁴]octane-2-carboxamide;

rac-(1R,2R,4S,5R,6S)-6-hydroxy-N-(2-methoxy-5-(trifluoromethyl)phenyl)-4-(2-methoxypyridin-4-yl)-8-oxatricyclo[3.2.1.0²,⁴]octane-2-carboxamide;

rac-(1R,2R,4S,5R,6S)-N-(3,5-bis(trifluoromethyl)phenyl)-6-hydroxy-4-(2-methoxypyridin-4-yl)-8-oxatricyclo[3.2.1.0²,⁴]octane-2-carboxamide;

rac-(1R,2R,4S,5R,6S)-N-(4-cyano-3-(trifluoromethyl)phenyl)-6-hydroxy-4-(2-methoxypyridin-4-yl)-8-oxatricyclo[3.2.1.0²,⁴]octane-2-carboxamide;

rac-(1R,2R,4S,5R,6S)-N-(2-cyano-5-(trifluoromethyl)phenyl)-6-hydroxy-4-(2-methoxypyridin-4-yl)-8-oxatricyclo[3.2.1.0²,⁴]octane-2-carboxamide;

(1R,2R,4S,5R,6S)-N-(2-cyano-5-(trifluoromethyl)phenyl)-6-hydroxy-4-(2-methoxypyridin-4-yl)-8-oxatricyclo[3.2.1.0²,⁴]octane-2-carboxamide;

(1S,2S,4R,5S,6R)-N-(2-cyano-5-(trifluoromethyl)phenyl)-6-hydroxy-4-(2-methoxypyridin-4-yl)-8-oxatricyclo[3.2.1.0²,⁴]octane-2-carboxamide;

rac-(1R,2R,4S,5R,6S)-N-(3-chloro-4-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide;

rac-(1R,2R,4S,5R,6S)-N-(3-fluoro-4-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide;

rac-(1R,2R,4S,5R,6S)-6-hydroxy-4-(1-methyl-3-(trifluoromethyl)-1H-pyrazol-4-yl)-N-(4-(trifluoromethyl)phenyl)-8-oxatricyclo[3.2.1.0²,⁴]octane-2-carboxamide;

rac-(1R,2R,4S,5R,6S)-6-hydroxy-4-(1-methyl-3-(trifluoromethyl)-1H-pyrazol-4-yl)-N-(4-(trifluoromethyl)pyridin-2-yl)-8-oxatricyclo[3.2.1.0²,⁴]octane-2-carboxamide;

rac-(1R,2R,4S,5R,6S)-N-(6-chloro-4-(trifluoromethyl)pyridin-2-yl)-6-hydroxy-4-(1-methyl-3-(trifluoromethyl)-1H-pyrazol-4-yl)-8-oxatricyclo[3.2.1.0²,⁴]octane-2-carboxamide;

rac-(1R,2R,4S,5R,6S)-N-(5-chloro-4-(trifluoromethyl)pyridin-2-yl)-6-hydroxy-4-(1-methyl-3-(trifluoromethyl)-1H-pyrazol-4-yl)-8-oxatricyclo[3.2.1.0²,⁴]octane-2-carboxamide;

rac-(1R,2R,4S,5R,6S)-N-(6-cyclopropyl-4-(trifluoromethyl)pyridin-2-yl)-6-hydroxy-4-(1-methyl-3-(trifluoromethyl)-1H-pyrazol-4-yl)-8-oxatricyclo[3.2.1.0²,⁴]octane-2-carboxamide;

rac-(1R,2R,4S,5R,6S)-6-hydroxy-4-(1-methyl-3-(trifluoromethyl)-1H-pyrazol-4-yl)-N-(6-methyl-4-(trifluoromethyl)pyridin-2-yl)-8-oxatricyclo[3.2.1.0²,⁴]octane-2-carboxamide;

rac-(1R,2R,4S,5R,6S)-N-(6-ethoxy-4-(trifluoromethyl)pyridin-2-yl)-6-hydroxy-4-(1-methyl-3-(trifluoromethyl)-1H-pyrazol-4-yl)-8-oxatricyclo[3.2.1.0²,⁴]octane-2-carboxamide;

rac-(1R,2R,4S,5R,6S)-6-hydroxy-4-(1-methyl-3-(trifluoromethyl)-1H-pyrazol-4-yl)-N-(3-(trifluoromethyl)phenyl)-8-oxatricyclo[3.2.1.0²,⁴]octane-2-carboxamide;

rac-(1R,2R,4S,5R,6S)-6-hydroxy-4-(1-methyl-3-(trifluoromethyl)-1H-pyrazol-4-yl)-N-(2-methyl-3-(trifluoromethyl)phenyl)-8-oxatricyclo[3.2.1.0²,⁴]octane-2-carboxamide;

rac-(1R,2R,4S,5R,6S)-6-hydroxy-4-(1-methyl-3-(trifluoromethyl)-1H-pyrazol-4-yl)-N-(4-methyl-3-(trifluoromethyl)phenyl)-8-oxatricyclo[3.2.1.0²,⁴]octane-2-carboxamide;

rac-(1R,2R,4S,5R,6S)-6-hydroxy-4-(1-methyl-3-(trifluoromethyl)-1H-pyrazol-4-yl)-N-(3-methyl-5-(trifluoromethyl)phenyl)-8-oxatricyclo[3.2.1.0²,⁴]octane-2-carboxamide;

rac-(1R,2R,4S,5R,6S)-6-hydroxy-4-(1-methyl-3-(trifluoromethyl)-1H-pyrazol-4-yl)-N-(2-methyl-5-(trifluoromethyl)phenyl)-8-oxatricyclo[3.2.1.0²,⁴]octane-2-carboxamide;

rac-(1R,2R,4S,5R,6S)-N-(2-fluoro-3-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide;

rac-(1R,2R,4S,5R,6S)-N-(4-fluoro-3-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide;

rac-(1R,2R,4S,5R,6S)-N-(3-fluoro-5-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide;

rac-(1R,2R,4S,5R,6S)-N-(2-fluoro-5-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide;

rac-(1R,2R,4S,5R,6S)-N-(4-chloro-3-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide;

rac-(1R,2R,4S,5R,6S)-N-(3-chloro-5-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide;

rac-(1R,2R,4S,5R,6S)-6-hydroxy-N-(4-methoxy-3-(trifluoromethyl)phenyl)-4-(1-methyl-3-(trifluoromethyl)-1H-pyrazol-4-yl)-8-oxatricyclo[3.2.1.0²,⁴]octane-2-carboxamide;

rac-(1R,2R,4S,5R,6S)-6-hydroxy-N-(3-methoxy-5-(trifluoromethyl)phenyl)-4-(1-methyl-3-(trifluoromethyl)-1H-pyrazol-4-yl)-8-oxatricyclo[3.2.1.0²,⁴]octane-2-carboxamide;

rac-(1R,2R,4S,5R,6S)-6-hydroxy-N-(2-methoxy-5-(trifluoromethyl)phenyl)-4-(1-methyl-3-(trifluoromethyl)-1H-pyrazol-4-yl)-8-oxatricyclo[3.2.1.0²,⁴]octane-2-carboxamide;

rac-(1R,2R,4S,5R,6S)-N-(3,5-bis(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide;

rac-(1R,2R,4S,5R,6S)-6-hydroxy-4-(1-methyl-3-(trifluoromethyl)-1H-pyrazol-4-yl)-N-(4-morpholino-3-(trifluoromethyl)phenyl)-8-oxatricyclo[3.2.1.0²,⁴]octane-2-carboxamide;

rac-(1R,2R,4S,5R,6S)-N-(4-ethoxy-3-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide;

rac-(1R,2R,4S,5R,6S)-6-hydroxy-N-(3-(trifluoromethyl)phenyl)-4-(2-(trifluoromethyl)pyridin-4-yl)-8-oxatricyclo[3.2.1.0²,⁴]octane-2-carboxamide;

rac-(1R,2R,4S,5R,6S)-6-hydroxy-N,4-bis(3-(trifluoromethyl)phenyl)-8-oxatricyclo[3.2.1.0²,⁴]octane-2-carboxamide;

rac-(1R,2R,4S,5R,6S)-N-(4-cyano-3-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide;

rac-(1R,2R,4S,5R,6S)-N-(2-cyano-5-(trifluoromethyl)phenyl)-6-hydroxy-4-(1-methyl-3-(trifluoromethyl)-1H-pyrazol-4-yl)-8-oxatricyclo[3.2.1.0²,⁴]octane-2-carboxamide;

rac-(1R,2R,4S,5R,6S)-N-(4-chloro-3-(trifluoromethyl)phenyl)-6-hydroxy-4-(2-methoxypyridin-4-yl)-8-oxatricyclo[3.2.1.0²,⁴]octane-2-carboxamide;

rac-(1R,2R,4S,5R,6S)-N-(3-chloro-5-(trifluoromethyl)phenyl)-6-hydroxy-4-(2-methoxypyridin-4-yl)-8-oxatricyclo[3.2.1.0²,⁴]octane-2-carboxamide;

rac-(1R,2R,4S,5R,6S)-N-(3-cyano-5-(trifluoromethyl)phenyl)-6-hydroxy-4-(2-methoxypyridin-4-yl)-8-oxatricyclo[3.2.1.0²,⁴]octane-2-carboxamide;

rac-(1R,2R,4S,5R,6S)-N-(3-fluoro-5-(trifluoromethyl)phenyl)-6-hydroxy-4-(2-methoxypyridin-4-yl)-8-oxatricyclo[3.2.1.0²,⁴]octane-2-carboxamide;

rac-(1R,2R,4S,5R,6S)-N-(3-chloro-4-(trifluoromethyl)phenyl)-6-hydroxy-4-(2-methoxypyridin-4-yl)-8-oxatricyclo[3.2.1.0²,⁴]octane-2-carboxamide;

rac-(1R,2R,4S,5R,6S)-N-(3-fluoro-4-(trifluoromethyl)phenyl)-6-hydroxy-4-(2-methoxypyridin-4-yl)-8-oxatricyclo[3.2.1.0²,⁴]octane-2-carboxamide;

rac-(1R,2R,4S,5R,6S)-6-hydroxy-4-(2-methoxypyridin-4-yl)-N-(4-(trifluoromethyl)phenyl)-8-oxatricyclo[3.2.1.0²,⁴]octane-2-carboxamide;

rac-(1R,2R,4S,5R,6S)-N-(3-cyano-5-(trifluoromethyl)phenyl)-4-(2-fluoropyridin-4-yl)-6-hydroxy-8-oxatricyclo[3.2.1.0²,⁴]octane-2-carboxamide;

rac-(1R,2R,4S,5R,6S)-N-(2-cyano-5-(trifluoromethyl)phenyl)-4-(2-fluoropyridin-4-yl)-6-hydroxy-8-oxatricyclo[3.2.1.0²,⁴]octane-2-carboxamide;

rac-(1R,2R,4S,5R,6S)-N-(4-cyano-3-(trifluoromethyl)phenyl)-6-hydroxy-4-(3-(trifluoromethyl)phenyl)-8-oxatricyclo[3.2.1.0²,⁴]octane-2-carboxamide;

rac-(1R,2R,4S,5R,6S)-N-(2-cyano-5-(trifluoromethyl)phenyl)-6-hydroxy-4-(3-(trifluoromethyl) phenyl)-8-oxatricyclo[3.2.1.0²,⁴]octane-2-carboxamide;

rac-(1R,2R,4S,5R,6S)-N-(2-fluoro-5-(trifluoromethyl)phenyl)-6-hydroxy-4-(3-(trifluoromethyl)phenyl)-8-oxatricyclo[3.2.1.0²,⁴]octane-2-carboxamide; and rac-(1R,2R,4S,5R,6S)-6-hydroxy-4-(3-(trifluoromethyl)phenyl)-N-(4-(trifluoromethyl)pyridin-2-yl)-8-oxatricyclo[3.2.1.0²,⁴]octane-2-carboxamide;

or an enantiomer, an enantiomeric mixture thereof or a pharmaceutically acceptable salt thereof.

12. The compound according to claim 1 or a pharmaceutically acceptable salt thereof, wherein said compound has an enantiomeric excess of at least 50% of the (1R,2R,4S,5R,6S) enantiomer.

13. The compound according to claim 1 or a pharmaceutically acceptable salt thereof, wherein said compound has an enantiomeric excess of at least 75% of the (1R,2R,4S,5R,6S) enantiomer.

14. The compound according to claim 1 or a pharmaceutically acceptable salt thereof, wherein said compound has an enantiomeric excess of at least 85% of the (1R,2R,4S,5R,6S) enantiomer.

15. The compound according to claim 1 or a pharmaceutically acceptable salt thereof, wherein said compound has an enantiomeric excess of at least 95% of the (1R,2R,4S,5R,6S) enantiomer.

16. A pharmaceutical composition comprising a compound according to claim 1 and one or more pharmaceutically acceptable carriers.

17. A combination comprising a compound according to claim 1 and one or more therapeutically active agents.

18. A method for treating, ameliorating or preventing arthritis or joint injury due to increased alkaline phosphatase or chondrocyte hypertrophy, or for cartilage repair in a subject in need thereof, comprising administering a therapeutically effective amount of a compound according to claim 1 and optionally in combination with a second therapeutic agent; thereby treating, ameliorating or preventing arthritis or said joint injury, or repairing cartilage, in said subject.

19. The method of claim 18, wherein said compound is administered orally.

20. A method of inducing hyaline cartilage production comprising contacting chondrogenic progenitor cells with a therapeutically effective amount of a compound according to claim 1, optionally in combination with a second therapeutic agent;

thereby inducing hyaline cartilage production.

21. The method of claim 20, wherein said contacting step is performed in vitro or in vivo in a mammal; and when in vivo, the chrondrogenic progenitor cells are present in the mammal.

22. The method of claim 20, wherein said contacting step occurs in an extracellular matrix or biocompatible scaffold.

23. The method according to claim 20, further comprising inducing differentiation of chondrocyte progenitor cells into mature chondrocytes.

24. The method of claim 18, wherein said arthritis is osteoarthritis.

* * * * *